US005750373A

United States Patent [19]
Garrard et al.

[11] Patent Number: 5,750,373
[45] Date of Patent: May 12, 1998

[54] ENRICHMENT METHOD FOR VARIANT PROTEINS HAVING ALTERED BINDING PROPERTIES, M13 PHAGEMIDS, AND GROWTH HORMONE VARIANTS

[75] Inventors: Lisa J. Garrard, Burlingame; Dennis J. Henner, Pacifica; Steven Bass, Redwood City, all of Calif.; Ronald Greene, Durham, N.C.; Henry B. Lowman, Hercules, Calif.; James A. Wells, Burlingame, Calif.; David J. Matthews, San Francisco, Calif.

[73] Assignee: Genentech, Inc., South San Francisco, Calif.

[21] Appl. No.: 50,058

[22] PCT Filed: Dec. 3, 1991

[86] PCT No.: PCT/US91/09133

§ 371 Date: Apr. 30, 1993

§ 102(e) Date: Apr. 30, 1993

[51] Int. Cl.$^6$ .......................... C12P 21/06; C12N 15/63; C07K 14/61
[52] U.S. Cl. .................. 435/69.4; 435/320.1; 530/399
[58] Field of Search ............................ 435/69.4, 69.7, 435/7.1, 320.1; 530/399

[56] References Cited

U.S. PATENT DOCUMENTS 4,593,002  6/1986  Dulbecco ........................ 435/172.3

FOREIGN PATENT DOCUMENTS

WO 90/02809  3/1990  WIPO.
WO 90/04788  5/1990  WIPO.
WO 92/01047  1/1992  WIPO.

OTHER PUBLICATIONS

Vieira et al 1987 Meth. Enzymol 153:3-11.
Cunningham et al 1989 Science 244: 1081-1085.
Armstrong, et al., "Domain Structure of Bacteriophage fd Adsorption Protein" *FEBS Letters* 135(1):167-172 (Nov. 1981).
Bowie, et al., "Deciphering the Message in Protein Sequences: Tolerance to Amino Acid Substitutions" *Science* 247:1306-1310 (Mar. 1990).
Crissman and Smith, "Gene-III Protein of Filamentos Phages: Evidence for a Carboxyl-Terminal Domain with a Role in Morphogenesis" *Virology* 132:445-455 (1984).
Cunningham, et al., "Engineering Human Prolactin to Bind to the Human Growth Hormone Receptor" *Science* 24:1461-1465 (Mar. 1990).
Cwirla, et al., "Peptides on phage: A vast library of peptides for identifying ligands" *Proc. Natl. Acad. Sci. USA* 87:6378-6382 (Aug. 1990).
de la Cruz, et al., "Immunogencitiy and Epitope Mapping of Foreign Sequences via Genetically Engineered Filamentous Phage" *J. of Biol. Chem.* 263:4318-4322 (Mar. (1988).

Delvin, et al., "Random Peptide Libraries: A Source of Specific Protein Binding Molecules" *Science* 249:404-406 (Jul. 1990).
Fuh et al., "The Human Growth Hormone Receptor" *J. of Biol. Chem.* 265(6):3111-3115 (Feb. 1990).
Geysen, et al., "A Priori Delineation of a Peptide which Mimics a Discontinuous Antigenic Determinant" *Mol. Immunology* 23(7):709-715 (1986).
Geysen, et al., "Antigen-antibody interactions at the molecular level: adventures in peptide synthesis" *Immunology Today* 6(12):364-369 (1985).
Gussow, et al., "Generating Binding Activities from *Escherichia coli* by Expression of a Repertoire of Immunoglobulin Variable Domains" *Cold Springs Harbor Symposia on Quantitatve Biology* vol. LIV.:265-272 (1989).
McFarland, et al., "Lutropin-Choriogonadotropin Receptor: An Unusual Member of the G Protein-Coupled Receptor Family" *Science* 245:494-499 (Aug. 1989).
Parmley and Smith, "Antibody-selectable filamentous fd phage vectors:affinity purification of target genes" *Gene* 73:305-318 (1988).
Rasched and Oberer "Ff Coliphages: Structures and Functional Relationships" *Microbiological Reviews* 50(4):401-427 (Dec. 1986).
Rutter et al., "Redesigning Proteins via Genetic Engineering" *Protein Engineering* Oxender & Fox, eds., A.R. Liss, Inc., New York pp. 103-108 (1985).
Scott and Smith "Searching for Peptide Ligands with an Epitope Library" *Science* 249:386-390 (Jul. 1990).
Shortle, "Genetic Strategies for Analyzing Proteins" *Protein Engineering* Oxender & Fox eds., A.R. Liss, Inc., New York pp. 103-108 (1987).
Smith, "Filamentous Fusion Phage: Novel Expression Vectors That Display Cloned Antigens on the Virion Surface" *Science* 228:1315-1317 (Jun. 1985).
Wells, et al., "Cassette mutagenesis: an efficient methods for generation of multiple mutations at defined sites" *Gene* 34:315-323 (1985).

*Primary Examiner*—Vasu S. Jagannathan
*Assistant Examiner*—K. Cochrane Carlson
*Attorney, Agent, or Firm*—Daryl B. Winter; Walter H. Dreger

[57] ABSTRACT

A method for selecting novel proteins such as growth hormone and antibody fragment variants having altered binding properties for their respective receptor molecules is provided. The method comprises fusing a gene encoding a protein of interest to the carboxy terminal domain of the gene III coat protein of the filamentous phage M13. The gene fusion is mutated to form a library of structurally related fusion proteins that are expressed in low quantity on the surface of a phagemid particle. Biological selection and screening are employed to identify novel ligands useful as drug candidates. Disclosed are preferred phagemid expression vectors and selected human growth hormone variants.

50 Claims, 20 Drawing Sheets

Starting Library:
NNS codons at hGH residues
172, 174, 176, 178

↓ 3.9 x 10⁷ transformants

Glycine elution

↓

Glycine elution

↓

KELR    +      += L163P
KDIN
REGK
RNGP
CNGK
SKLS
QRPG    ++     ++= K168R
LLLV

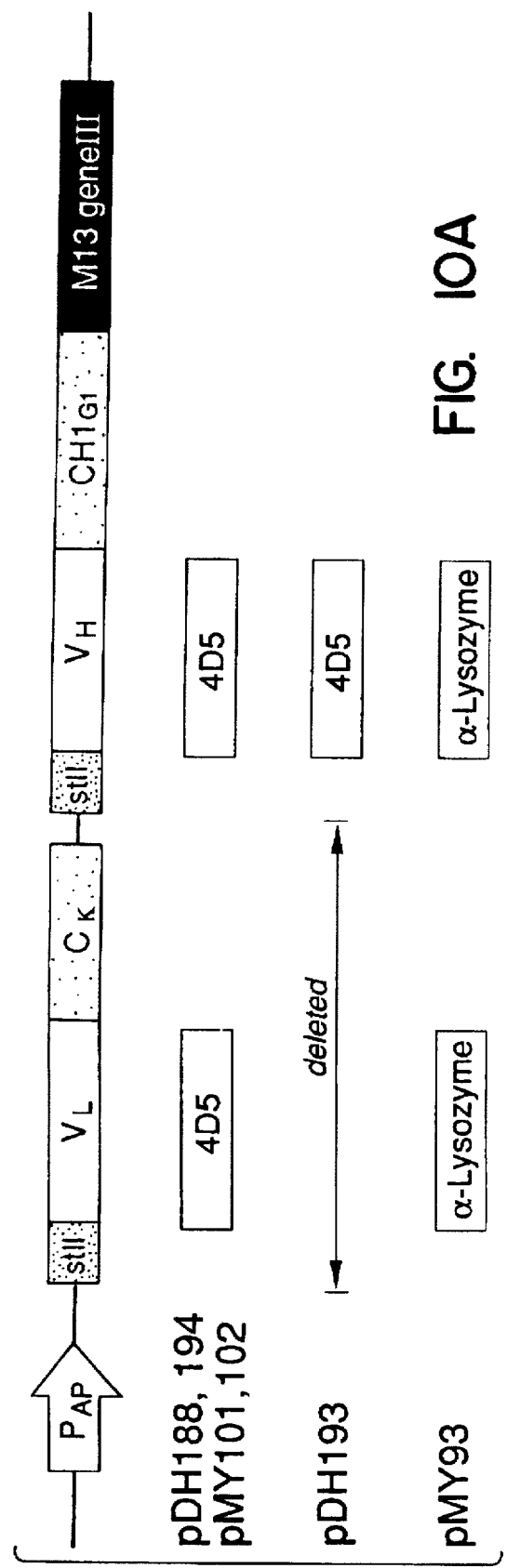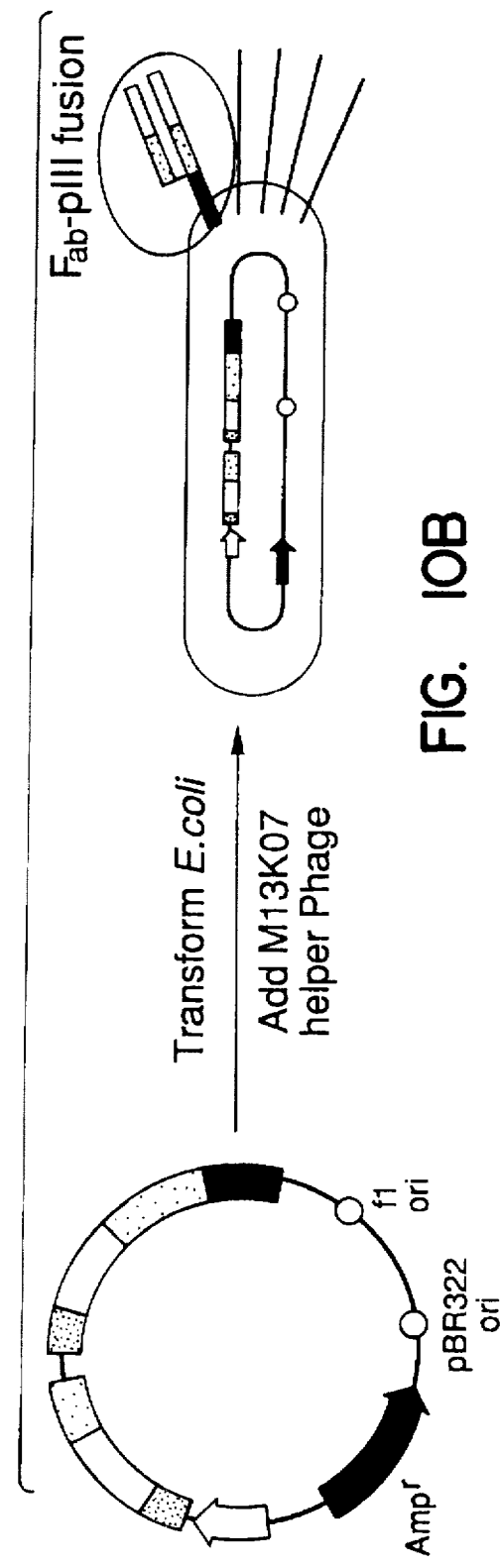
FIG. 10A
FIG. 10B

FIG. 11A

```
ATG AAA AAG AAT ATC GCA TTT CTT CTT GCA TCT ATG  36
Met Lys Lys Asn Ile Ala Phe Leu Leu Ala Ser Met
 1                   5                      10

TTC GTT TTT TCT ATT GCT ACA AAC GCG TAC GCT GAT ATC  75
Phe Val Phe Ser Ile Ala Thr Asn Ala Tyr Ala Asp Ile
         15                      20              25

CAG ATG ACC CAG TCC CCG AGC TCC CTG TCC GCC TCT GTG  114
Gln Met Thr Gln Ser Pro Ser Ser Leu Ser Ala Ser Val
             30                      35

GGC GAT AGG GTC ACC ATC ACC TGC CGT GCC AGT CAG GAT  153
Gly Asp Arg Val Thr Ile Thr Cys Arg Ala Ser Gln Asp
 40                      45                      50

GTG AAT ACT GCT GTA GCC TGG TAT CAA CAG AAA CCA GGA  192
Val Asn Thr Ala Val Ala Trp Tyr Gln Gln Lys Pro Gly
             55                      60

AAA GCT CCG AAA CTA CTG ATT TAC TCG GCA TCC TTC CTC  231
Lys Ala Pro Lys Leu Leu Ile Tyr Ser Ala Ser Phe Leu
 65                      70                      75

TAC TCT GGA GTC CCT TCT CGC TTC TCT GGA TCC AGA TCT  270
Tyr Ser Gly Val Pro Ser Arg Phe Ser Gly Ser Arg Ser
             80                      85              90
```

FIG. 11B

```
GGG ACG GAT TTC ACT CTG ACC ATC AGC AGT CTG CAG CCG  309
Gly Thr Asp Phe Thr Leu Thr Ile Ser Ser Leu Gln Pro
             95                 100

GAA GAC TTC GCA ACT TAT TAC TGT CAG CAA CAT TAT ACT  348
Glu Asp Phe Ala Thr Tyr Tyr Cys Gln Gln His Tyr Thr
105                     110                 115

ACT CCT CCC ACG TTC GGA CAG GGT ACC AAG GTG GAG ATC  387
Thr Pro Pro Thr Phe Gly Gln Gly Thr Lys Val Glu Ile
        120                 125

AAA CGA ACT GTG GCT GCA CCA TCT GTC TTC ATC TTC CCG  426
Lys Arg Thr Val Ala Ala Pro Ser Val Phe Ile Phe Pro
130                 135                 140

CCA TCT GAT GAG CAG TTG AAA TCT GGA ACT GCC TCT GTT  465
Pro Ser Asp Glu Gln Leu Lys Ser Gly Thr Ala Ser Val
            145                 150                 155

GTG TGC CTG CTG AAT AAC TTC TAT CCC AGA GAG GCC AAA  504
Val Cys Leu Leu Asn Asn Phe Tyr Pro Arg Glu Ala Lys
                160                 165

GTA CAG TGG AAG GTG GAT AAC GCC CTC CAA TCG GGT AAC  543
Val Gln Trp Lys Val Asp Asn Ala Leu Gln Ser Gly Asn
170                 175                 180
```

FIG. 11C

```
TCC CAG GAG AGT GTC ACA GAG CAG GAC AGC AAG GAC AGC 582
Ser Gln Glu Ser Val Thr Glu Gln Asp Ser Lys Asp Ser
            185                 190

ACC TAC AGC CTC AGC AGC ACC CTG ACG CTG AGC AAA GCA 621
Thr Tyr Ser Leu Ser Ser Thr Leu Thr Leu Ser Lys Ala
195                 200                 205

GAC TAC GAG AAA CAC AAA GTC TAC GCC TGC GAA GTC ACC 660
Asp Tyr Glu Lys His Lys Val Tyr Ala Cys Glu Val Thr
    210                 215                 220

CAT CAG GGC CTG AGC TCG CCC GTC ACA AAG AGC TTC AAC 699
His Gln Gly Leu Ser Ser Pro Val Thr Lys Ser Phe Asn
                225                 230

AGG GGA GAG TGT TAAGCTGAT CCTCTACGCC GGACGCATCG 740
Arg Gly Glu Cys
    235     237

TGGCCCTAGT ACGCAAGTTC ACGTAAAAAG GGTATCTAGA GGTTGAGGTG 790

ATTTT    ATG AAA AAG AAT ATC GCA TTT CTT CTT GCA TCT 828
         Met Lys Lys Asn Ile Ala Phe Leu Leu Ala Ser
         238                 240                 245
```

FIG. 11D

```
ATG TTC GTT TTT TCT ATT GCT ACA AAC GCG TAC GCT GAG 867
Met Phe Val Phe Ser Ile Ala Thr Asn Ala Tyr Ala Glu
    250                 255                 260

GTT CAG CTG GTG GAG TCT GGC GGT GGC CTG GTG CAG CCA 906
Val Gln Leu Val Glu Ser Gly Gly Gly Leu Val Gln Pro
            265                 270

GGG GGC TCA CTC CGT TTG TCC TGT GCA GCT TCT GGC TTC 945
Gly Gly Ser Leu Arg Leu Ser Cys Ala Ala Ser Gly Phe
275                 280                 285

AAC ATT AAA GAC ACC TAT ATA CAC TGG GTG CGT CAG GCC 984
Asn Ile Lys Asp Thr Tyr Ile His Trp Val Arg Gln Ala
        290                 295                 300

CCG GGT AAG GGC CTG GAA TGG GTT GCA AGG ATT TAT CCT 1023
Pro Gly Lys Gly Leu Glu Trp Val Ala Arg Ile Tyr Pro
                305                 310

ACG AAT GGT TAT ACT AGA TAT GCC GAT AGC GTC AAG GGC 1062
Thr Asn Gly Tyr Thr Arg Tyr Ala Asp Ser Val Lys Gly
315                 320                 325

CGT TTC ACT ATA AGC GCA GAC ACA TCC AAA AAC ACA GCC 1101
Arg Phe Thr Ile Ser Ala Asp Thr Ser Lys Asn Thr Ala
        330                 335
```

FIG. 11E

TAC CTG CAG ATG AAC AGC CTG CGT GCT GAG GAC ACT GCC 1140
Tyr Leu Gln Met Asn Ser Leu Arg Ala Glu Asp Thr Ala
340                 345                 350

GTC TAT TAT TGT TCT AGA TGG GGA GGG GAC GGC TTC TAT 1179
Val Tyr Tyr Cys Ser Arg Trp Gly Gly Asp Gly Phe Tyr
        355                 360                 365

GCT ATG GAC TAC TGG GGT CAA GGA ACC CTG GTC ACC GTC 1218
Ala Met Asp Tyr Trp Gly Gln Gly Thr Leu Val Thr Val
            370                 375

TCC TCG GCC TCC ACC AAG GGC CCA TCG GTC TTC CCC CTG 1257
Ser Ser Ala Ser Thr Lys Gly Pro Ser Val Phe Pro Leu
380                 385                 390

GCA CCC TCC TCC AAG AGC ACC TCT GGG GGC ACA GCG GCC 1296
Ala Pro Ser Ser Lys Ser Thr Ser Gly Gly Thr Ala Ala
                395                 400

CTG GGC TGC CTG GTC AAG GAC TAC TTC CCC GAA CCG GTG 1335
Leu Gly Cys Leu Val Lys Asp Tyr Phe Pro Glu Pro Val
405                 410                 415

ACG GTG TCG TGG AAC TCA GGC GCC CTG ACC AGC GGC GTG 1374
Thr Val Ser Trp Asn Ser Gly Ala Leu Thr Ser Gly Val
            420                 425                 430

```
CAC ACC TTC CCG GCT GTC CTA CAG TCC TCA GGA CTC TAC  1413
His Thr Phe Pro Ala Val Leu Gln Ser Ser Gly Leu Tyr
            435                 440

TCC CTC AGC AGC GTG GTG ACT GTG CCC TCT AGC AGC TTG  1452
Ser Leu Ser Ser Val Val Thr Val Pro Ser Ser Ser Leu
    445                 450                 455

GGC ACC CAG ACC TAC ATC TGC AAC GTG AAT CAC AAG CCC  1491
Gly Thr Gln Thr Tyr Ile Cys Asn Val Asn His Lys Pro
        460                 465                 480

AGC AAC ACC AAG GTG GAC AAG AAA GTT GAG CCC AAA TCT  1530
Ser Asn Thr Lys Val Asp Lys Lys Val Glu Pro Lys Ser
470                 475                 480

TGT GAC AAA ACT CAC ACA GGG CCC TTC GTT TGT GAA TAT  1569
Cys Asp Lys Thr His Thr Gly Pro Phe Val Cys Glu Tyr
            485                 490                 495

CAA GGC CAA TCG TCT GAC CTG CCT CAA CCT GTC AAT  1608
Gln Gly Gln Ser Ser Asp Leu Pro Gln Pro Val Asn
        500                 505

GCT GGC GGC GGT GGC TCT GGT GGT GGT TCT GGC GGC TCT  1647
Ala Gly Gly Gly Gly Ser Gly Gly Gly Gly Ser Gly Gly Ser
510                 515                 520
```

FIG. 11F

FIG. IIG

| | | | | | | | | |
|---|---|---|---|---|---|---|---|---|
| GAG | GGT | GGT | GGC | TCT | GAG | GGT | TCT | GAG GGT GGC 1686 |
| Glu | Gly | Gly | Gly | Ser | Glu | Gly | Ser | Glu Gly Gly |
| | | 525 | | | 530 | | | |

| GGC | TCT | GAG | GGA | GGC | GGT | TCC | GGT | GGC TCT GGT TCC 1725 |
|---|---|---|---|---|---|---|---|---|
| Gly | Ser | Glu | Gly | Gly | Gly | Ser | Gly | Gly Ser Gly Ser |
| 535 | | | 540 | | | 545 | | |

| GGT | GAT | TTT | GAT | TAT | GAA | AAG | ATG | GCA AAC GCT AAT AAG 1764 |
|---|---|---|---|---|---|---|---|---|
| Gly | Asp | Phe | Asp | Tyr | Glu | Lys | Met | Ala Asn Ala Asn Lys |
| | 550 | | | | 555 | | | 560 |

| GGG | GCT | ATG | ACC | GAA | AAT | GCC | GAT | GAA AAC GCG CTA CAG 1803 |
|---|---|---|---|---|---|---|---|---|
| Gly | Ala | Met | Thr | Glu | Asn | Ala | Asp | Glu Asn Ala Leu Gln |
| | | 565 | | | | 570 | | |

| TCT | GAC | GCT | AAA | GGC | AAA | CTT | GAT | TCT GTC GCT ACT GAT 1842 |
|---|---|---|---|---|---|---|---|---|
| Ser | Asp | Ala | Lys | Gly | Lys | Leu | Asp | Ser Val Ala Thr Asp |
| 575 | | | | | 580 | | | 585 |

| TAC | GGT | GCT | GCT | ATC | GAT | GGT | TTC | ATT GGT GAC GTT TCC 1881 |
|---|---|---|---|---|---|---|---|---|
| Tyr | Gly | Ala | Ala | Ile | Asp | Gly | Phe | Ile Gly Asp Val Ser |
| | | | 590 | | | | 595 | |

| GGC | CTT | GCT | AAT | GGT | GCT | ACT | GGT | GAT TTT GCT 1920 |
|---|---|---|---|---|---|---|---|---|
| Gly | Leu | Ala | Asn | Gly | Ala | Thr | Gly | Asp Phe Ala |
| 600 | | | | 605 | | | | 610 |

FIG. 11H

```
GGC TCT AAT TCC CAA ATG GCT CAA GTC GGT GAC GGT GAT 1959
Gly Ser Asn Ser Gln Met Ala Gln Val Gly Asp Gly Asp
        615                 620                 625

AAT TCA CCT TTA ATG AAT AAT TTC CGT CAA TAT TTA CCT 1998
Asn Ser Pro Leu Met Asn Asn Phe Arg Gln Tyr Leu Pro
        630                 635

TCC CTC CCT CAA TCG GTT GAA TGT CGC CCT TTT GTC TTT 2037
Ser Leu Pro Gln Ser Val Glu Cys Arg Pro Phe Val Phe
        640                 645                 650

AGC GCT GGT AAA CCA TAT GAA TTT TCT ATT GAT TGT GAC 2076
Ser Ala Gly Lys Pro Tyr Glu Phe Ser Ile Asp Cys Asp
        655                 660

AAA ATA AAC TTA TTC CGT GGT GTC TTT GCG TTT CTT TTA 2115
Lys Ile Asn Leu Phe Arg Gly Val Phe Ala Phe Leu Leu
        665                 670                 675

TAT GTT GCC ACC TTT ATG TAT GTA TTT TCT ACG TTT GCT 2154
Tyr Val Ala Thr Phe Met Tyr Val Phe Ser Thr Phe Ala
        680                 685                 690

AAC ATA CTG CGT AAT AAG GAG TCT 2178
Asn Ile Leu Arg Asn Lys Glu Ser
        695         698
```

ENRICHMENT METHOD FOR VARIANT PROTEINS HAVING ALTERED BINDING PROPERTIES, M13 PHAGEMIDS, AND GROWTH HORMONE VARIANTS

FIELD OF THE INVENTION

This invention relates to the preparation and systematic selection of novel binding proteins having altered binding properties for a target molecule. Specifically, this invention relates to methods for producing foreign polypeptides mimicking the binding activity of naturally occurring binding partners. In preferred embodiments, the invention is directed to the preparation of therapeutic or diagnostic compounds that mimic proteins or nonpeptidyl molecules such as hormones, drugs and other small molecules, particularly biologically active molecules such as growth hormone.

BACKGROUND OF THE INVENTION

Binding partners are substances that specifically bind to one another, usually through noncovalent interactions. Examples of binding partners include ligand-receptor, antibody-antigen, drug-target, and enzyme-substrate interactions. Binding partners are extremely useful in both therapeutic and diagnostic fields.

Binding partners have been produced in the past by a variety of methods including; harvesting them from nature (e.g., antibody-antigen, and ligand-receptor pairings) and by adventitious identification (e.g. traditional drug development employing random screening of candidate molecules). In some instances these two approaches have been combined. For example, variants of proteins or polypeptides, such as polypeptide fragments, have been made that contain key functional residues that participate in binding. These polypeptide fragments, in turn, have been derivatized by methods akin to traditional drug development. An example of such derivitization would include strategies such as cyclization to conformationally constrain a polypeptide fragment to produce a novel candidate binding partner.

The problem with prior art methods is that naturally occurring ligands may not have proper characteristics for all therapeutic applications. Additionally, polypeptide ligands may not even be available for some target substances. Furthermore, methods for making non-naturally occurring synthetic binding partners are often expensive and difficult, usually requiring complex synthetic methods to produce each candidate. The inability to characterize the structure of the resulting candidate so that rational drug design methods can be applied for further optimization of candidate molecules further hampers these methods.

In an attempt to overcome these problems, Geysen (Geysen, Immun. Today 6:364–369 [1985]); and (Geysen et al., Mol. Immun., 23:709–715 [1986])has proposed the use of polypeptide synthesis to provide a framework for systematic iterative binding partner identification and preparation. According to Geysen et al., Ibid, short polypeptides, such as dipeptides, are first screened for the ability to bind to a target molecule. The most active dipeptides are then selected for an additional round of testing comprising linking, to the starting dipeptide, an additional residue (or by internally modifying the components of the original starting dipeptide) and then screening this set of candidates for the desired activity. This process is reiterated until the binding partner having the desired properties is identified.

The Geysen et al. method suffers from the disadvantage that the chemistry upon which it is based, peptide synthesis, produces molecules with ill-defined or variable secondary and tertiary structure. As rounds of iterative selection progress, random interactions accelerate among the various substituent groups of the polypeptide so that a true random population of interactive molecules having reproducible higher order structure becomes less and less attainable. For example, interactions between side chains of amino acids, which are sequentially widely separated but which are spatially neighbors, freely occur. Furthermore, sequences that do not facilitate conformationally stable secondary structures provide complex peptide-sidechain interactions which may prevent sidechain interactions of a given amino acid with the target molecule. Such complex interactions are facilitated by the flexibility of the polyamide backbone of the polypeptide candidates. Additionally, candidates may exist in numerous conformations making it difficult to identify the conformer that interacts or binds to the target with greatest affinity or specificity complicating rational drug design.

A final problem with the iterative polypeptide method of Geysen is that, at present, there are no practical methods with which a great diversity of different peptides can be produced, screened and analyzed. By using the twenty naturally occurring amino acids, the total number of all combinations of hexapeptides that must be synthesized is 64,000,000. Even having prepared such a diversity of peptides, there are no methods available with which mixtures of such a diversity of peptides can be rapidly screened to select those peptides having a high affinity for the target molecule. At present, each "adherent" peptide must be recovered in amounts large enough to carry out protein sequencing.

To overcome many of the problems inherent in the Geysen approach, biological selection and screening was chosen as an alternative. Biological selections and screens are powerful tools to probe protein function and to isolate variant proteins with desirable properties (Shortle, Protein Engineering, Oxender and Fox, eds., A. R. Liss, Inc., N.Y., pp. 103–106 [1988]) and Bowie et al., Science, 247:1306–1310 [1990)]. However, a given selection or screen is applicable to only one or a small number of related proteins.

Recently, Smith and coworkers (Smith, Science, 228:1315–1317 [1985]) and Parmley and Smith, Gene, 73:305–318 [1985] have demonstrated that small protein fragments (10–50 amino acids) can be "displayed" efficiently on the surface of filamentous phage by inserting short gene fragments into gene III of the fd phage ("fusion phage"). The gene III minor coat protein (present in about 5 copies at one end of the virion) is important for proper phage assembly and for infection by attachment to the pili of E. coli (see Rasched et al., Microbiol. Rev., 50:401–427 [1986]). Recently, "fusion phage" have been shown to be useful for displaying short mutated peptide sequences for identifying peptides that may react with antibodies (Scott et al., Science 249:386–390, [1990]) and Cwirla et al., Proc. Natl. Acad. U.S.A. 87:6378–6382, [1990]) or a foreign protein (Devlin et al., Science, 249:404–406 [1990]).

There are, however, several important limitations in using such "fusion phage" to identify altered peptides or proteins with new or enhanced binding properties. First, it has been shown (Parmley et al., Gene, 73:305–318, [1988]) that fusion phage are useful only for displaying proteins of less than 100 and preferably less than 50 amino acid residues, because large inserts presumably disrupt the function of gene III and therefore phage assembly and infectivity. Second, prior art methods have been unable to select peptides from a library having the highest binding affinity for a target molecule. For example, after exhaustive panning of a random peptide library with an anti-β endorphin monoclonal antibody, Cwirla and co-workers could not separate moderate affinity peptides ($K_d$~10 μM) from higher affinity peptides ($K_d$~0.4 μM) fused to phage. Moreover, the parent β-endorphin peptide sequence which has very high affinity ($K_d$~7 nM), was not panned from the epitope library.

Ladner WO 90/02802 discloses a method for selecting novel binding proteins displayed on the outer surface of cells and viral particles where it is contemplated that the heterologous proteins may have up to 164 amino acid residues. The method contemplates isolating and amplifying the displayed proteins to engineer a new family of binding proteins having desired affinity for a target molecule. More specifically, Ladner discloses a "fusion phage" displaying proteins having "initial protein binding domains" ranging from 46 residues (crambin) to 164 residues (T4 lysozyme) fused to the M13 gene III coat protein. Ladner teaches the use of proteins "no larger than necessary" because it is easier to arrange restriction sites in smaller amino acid sequences and prefers the 58 amino acid residue bovine pancreatic trypsin inhibitor (BPTI). Small fusion proteins, such as BPTI, are preferred when the target is a protein or macromolecule, while larger fusion proteins, such as T4 lysozyme, are preferred for small target molecules such as steroids because such large proteins have clefts and grooves into which small molecules can fit. The preferred protein, BPTI, is proposed to be fused to gene III at the site disclosed by Smith et al. or de la Cruz et al., *J. Biol. Chem.* 263:4318–4322 [1988], or to one of the terminii, along with a second synthetic copy of gene III so that "some" unaltered gene III protein will be present. Ladner does not adress the problem of successfully panning high affinity peptides from the random peptide library which plagues the biological selection and screening methods of the prior art.

Human growth hormone (hGH) participates in much of the regulation of normal human growth and development. This 22,000 dalton pituitary hormone exhibits a multitude of biological effects including linear growth (somatogenesis), tactation, activation of macrophages, insulin-like and diabetogenic effects among others (Chawla, R. K. (1983) *Ann. Rev. Med.* 34, 519; Edwards, C. K. et al. (1988) *Science* 239, 769; Thorner, M. O., et al. (1988) *J. Clin. Invest.* 81, 745). Growth hormone dificiency in children leads to dwarfism which has been successfully treated for more than a decade by exogenous administration of hGH. hGH is a member of a family of homologous hormones that include placental lactogens, prolactins, and other genetic and species variants or growth hormone (Nicoll, C. S., et al., (1986) *Endocrine Reviews* 7, 169). hGH is unusual among these in that it exhibits broad species specificity and binds to either the cloned somatogenic (Leung, D. W., et al., [1987] *Nature* 330, 537) or prolactin receptor (Boutin, J. M., et al., [1988] Ce:53, 69). The cloned gene for hGH has been expressed in a secreted form in *Escherichia coli* (Chang, C. N., et al., [1987] *Gene* 55, 189) and its DNA and amino acid sequence has been reported (Goeddel, et al., [1979] *Nature* 281, 544; Gray, et al., [1985] *Gene* 39, 247). The three-dimensional structure of hGH is not available. However, the three-dimensional folding pattern for porcine growth hormone (pGH) has been reported at moderate resolution and refinement (Abdel-Meguid, S. S., et al., [1987] *Proc. Natl. Acad. Sci. USA* 84, 6434). Human growth hormone's receptor and antibody epitopes have been identified by homolog-scanning mutagenesis (Cunningham et al., *Science* 243: 1330, 1989). The structure of novel amino terminal methionyl bovine growth hormone containing a spliced-in sequence of human growth hormone including histidine 18 and histidine 21 has been shown (U.S. Pat. No. 4,880,910).

Human growth hormone (hGH) causes a variety of physiological and metabolic effects in various animal models including linear bone growth, lactation, activation of macrophages, insulin-like and diabetogenic effects and others (R. K. Chawla et al., *Annu. Rev. Med.* 34, 519 (1983); O. G. P. Isaksson et al., *Annu. Rev. Physiol.* 47, 483 (1985); C. K. Edwards et al., *Science* 239, 769 (1988); M. O. Thorner and M. L. Vance, *J. Clin. Invest.* 82, 745 (1988); J. P. Hughes and H. G. Friesen, *Ann. Rev. Physiol.* 47, 469 (1985)). These biological effects derive from the interaction between hGH and specific cellular receptors.

Accordingly, it is an object of this invention to provide a rapid and effective method for the systematic preparation of candidate binding substances.

It is another object of this invention to prepare candidate binding substances displayed on surface of a phagemid particle that are conformationally stable.

It is another object of this invention to prepare candidate binding substances comprising fusion proteins of a phage coat protein and a heterologous polypeptide where the polypeptide is greater than 100 amino acids in length and may be more than one subunit and is displayed on a phagemid particle where the polypeptide is encoded by the phagemid genome.

It is a further object of this invention to provide a method for the preparation and selection of binding substances that is sufficiently versatile to present, or display, all peptidyl moieties that could potentially participate in a noncovalent binding interaction, and to present these moieties in a fashion that is sterically confined.

Still another object of the invention is the production of growth hormone variants that exhibit stronger affinity for growth hormone receptor and binding protein.

It is yet another object of this invention to produce expression vector phagemids that contain a suppressible termination codon functionally located between the heterologous polypeptide and the phage coat protein such that detectable fusion protein is produced in a host suppressor cell and only the heterologous polypeptide is produced in a non-suppressor host cell.

Finally, it is an object of this invention to produce a phagemid particle that rarely displays more than one copy of candidate binding proteins on the outer surface of the phagemid particle so that efficient selection of high affinity binding proteins can be achieved.

These and other objects of this invention will be apparent from consideration of the invention as a whole.

SUMMARY OF THE INVENTION

These objectives have been achieved by providing a method for selecting novel binding polypeptides comprising: (a) constructing a replicable expression vector comprising a first gene encoding a polypeptide, a second gene encoding at least a portion of a natural or wild-type phage coat protein wherein the first and second genes are heterologous, and a transcription regulatory element operably linked to the first and second genes, thereby forming a gene fusion encoding a fusion protein; (b) mutating the vector at one or more selected positions within the first gene thereby forming a family of related plasmids; (c) transforming suitable host cells with the plasmids; (d) infecting the transformed host cells with a helper phage having a gene encoding the phage coat protein; (e) culturing the transformed infected host cells under conditions suitable for forming recombinant phagemid particles containing at least a portion of the plasmid and capable of transforming the host, the conditions adjusted so that no more than a minor amount of phagemid particles display more than one copy of the fusion protein on the surface of the particle; (f) contacting the phagemid particles with a target molecule so that at least a portion of the phagemid particles bind to the target molecule; and (g) separating the phagemid particles that bind from those that do not. Preferably, the method further comprises transforming suitable host cells with recombinant phagemid particles that bind to the target molecule and repeating steps (d) through (g) one or more times.

Additionally, the method for selecting novel binding proteins where the proteins are composed of more than one subunit is achieved by selecting novel binding peptides comprising constructing a replicable expression vector comprising a transcription regulatory element operably linked to DNA encoding a protein of interest containing one or more subunits, wherein the DNA encoding at least one of the subunits is fused to the DNA encoding at least a portion of a phage coating protein-mutating the DNA encoding the protein of interest at one or more selected positions thereby forming a family of related vectors; transforming suitable host cells with the vectors; infecting the transformed host cells with a helper phage having a gene encoding the phage coat protein; culturing the transformed infected host cells under conditions suitable for forming recombinant phagemid particles containing at least a portion of the plasmid and capable of transforming the host, the conditions adjusted so that no more than a minor amount of phagemid particles display more than one copy of the fusion protein on the surface of the particle; containing the phagemid particles with a target molecule so that at least a portion of the phagemid particles bind to the target molecule; and separating the phagemid particles that bind from those that do not.

Preferably in the method of this invention the plasmid is under tight control of the transcription regulatory element, and the culturing conditions are adjusted so that the amount or number of phagemid particles displaying more than one copy of the fusion protein on the surface of the particle is less than about 1%. Also preferably, amount of phagemid particles displaying more than one copy of the fusion protein is less than 10% the amount of phagemid particles displaying a single copy of the fusion protein. Most preferably the amount is less than 20%.

Typically, in the method of this invention, the expression vector will further contain a secretory signal sequences fused to the DNA encoding each subunit of the polypeptide, and the transcription regulatory element will be a promoter system. Preferred promoter systems are selected from; Lac Z, $\lambda_{PL}$, TAC, T7 polymerase, tryptophan, and alkaline phosphatase promoters and combinations thereof.

Also typically, the first gene will encode a mammalian protein, preferably the protein will be selected from; human growth hormone (hGH), N-methionyl human growth hormone, bovine growth hormone, parathyroid hormone, thyroxine, insulin A-chain, insulin B-chain, proinsulin, relaxin A-chain, relaxin B-chain, prorelaxin, glycoprotein hormones such as follicle stimulating hormone (FSH), thyroid stimulating hormone (TSH), and leutinizing hormone (LH), glycoprotein hormone receptors, calcitonin, glucagon, factor VIII, an antibody, lung surfactant, urokinase, streptokinase, human tissue-type plasminogen activator (t-PA), bombesin, factor IX, thrombin, hemopoietic growth factor, tumor necrosis factor-alpha and -beta, enkephalinase, human serum albumin, mullerian-inhibiting substance, mouse gonadotropin-associated peptide, a microbial protein, such as betalactamase, tissue factor protein, inhibin, activin, vascular endothelial growth factor, receptors for hormones or growth factors; integrin, thrombopoietin, protein A or D, rheumatoid factors, nerve growth factors such as NGF-β, platelet-growth factor, transforming growth factors (TGF) such as TGF-alpha and TGF-beta, insulin-like growth factor-I and -II, insulin-like growth factor binding proteins, CD-4, DNase, latency associated peptide, erythropoietin, osteoinductive factors, interferons such as interferon-alpha, -beta, and -gamma, colony stimulating factors (CSFs) such as M-CSF, GM-CSF, and G-CSF, interleukins (ILs) such as IL-1, IL-2, IL-3, IL-4, superoxide dismutase; decay accelerating factor, viral antigen, HIV envelope proteins such as GP120, GP140, atrial natriuretic peptides A, B or C, immunoglobulins, and fragments of any of the above-listed proteins.

Preferably the first gene will encode a polypeptide of one or more subunits containing more than about 100 amino acid residues and will be folded to form a plurality of rigid secondary structures displaying a plurality of amino acids capable of interacting with the target. Preferably the first gene will be mutated at codons corresponding to only the amino acids capable of interacting with the target so that the integrity of the rigid secondary structures will be preserved.

Normally, the method of this invention will employ a helper phage selected from; M13KO7, M13R408, M13-VCS, and Phi X 174. The preferred helper phage is M13KO7, and the preferred coat protein is the M13 Phage gene III coat protein. The preferred host is *E. coli*, and protease deficient strains of *E. coli*. Novel hGH variants selected by the method of the present invention have been detected. Phagemid expression vectors were constructed that contain a suppressible termination codon functionally located between the nucleic acids encoding the polypeptide and the phage coat protein.

BRIEF DESCRIPTION OF THE FIGURES

FIG. 8. Sequences from phage selected on blank beads. The notation is as described in FIG. 5. After three rounds of selection with glycine elution, no siblings were observed and a background level of non-functional sequences remained.

FIGS. 10A and 10B. A. Diagram of plasmid pDH188 insert containing the DNA encoding the light chain and heavy chain (variable and constant domain 1) of the $F_{ab}$ humanized antibody directed to the HER-2receptor. $V_L$ and $V_H$ are the variable regions for the light and heavy chains, respectively. $C_k$ is the constant region of the human kappa light chain. $CH1_{G1}$ is the first constant region of the human gamma 1 chain. Both coding regions start with the bacterial st II signal sequence. B. A schematic diagram of the entire plasma pDH188 containing the insert described in 5A. After transformation of the plasmid into E. coli SR101 cells and the addition of helper phage, the plasmid is packaged into phage particles. Some of these particles display the $F_{ab}$-p III fusion (where p III is the protein encoded by the M13 gene III DNA). The segments in the plasmid figure correspond to the insert shown in 5A.

FIG. 11A through 11H are collectively referred to here as FIG. 11. The nucleotide (Seq. ID No. 25) sequence of the DNA encoding the 4D5 $F_{ab}$ molecule expressed on the phagemid surface. The amino acid sequence of the light chain is also shown (Seq. ID No. 26), as is the amino acid sequence of the heavy chain p III fusion (Seq. ID No. 27).

DETAILED DESCRIPTION OF THE INVENTION

Figure 1:
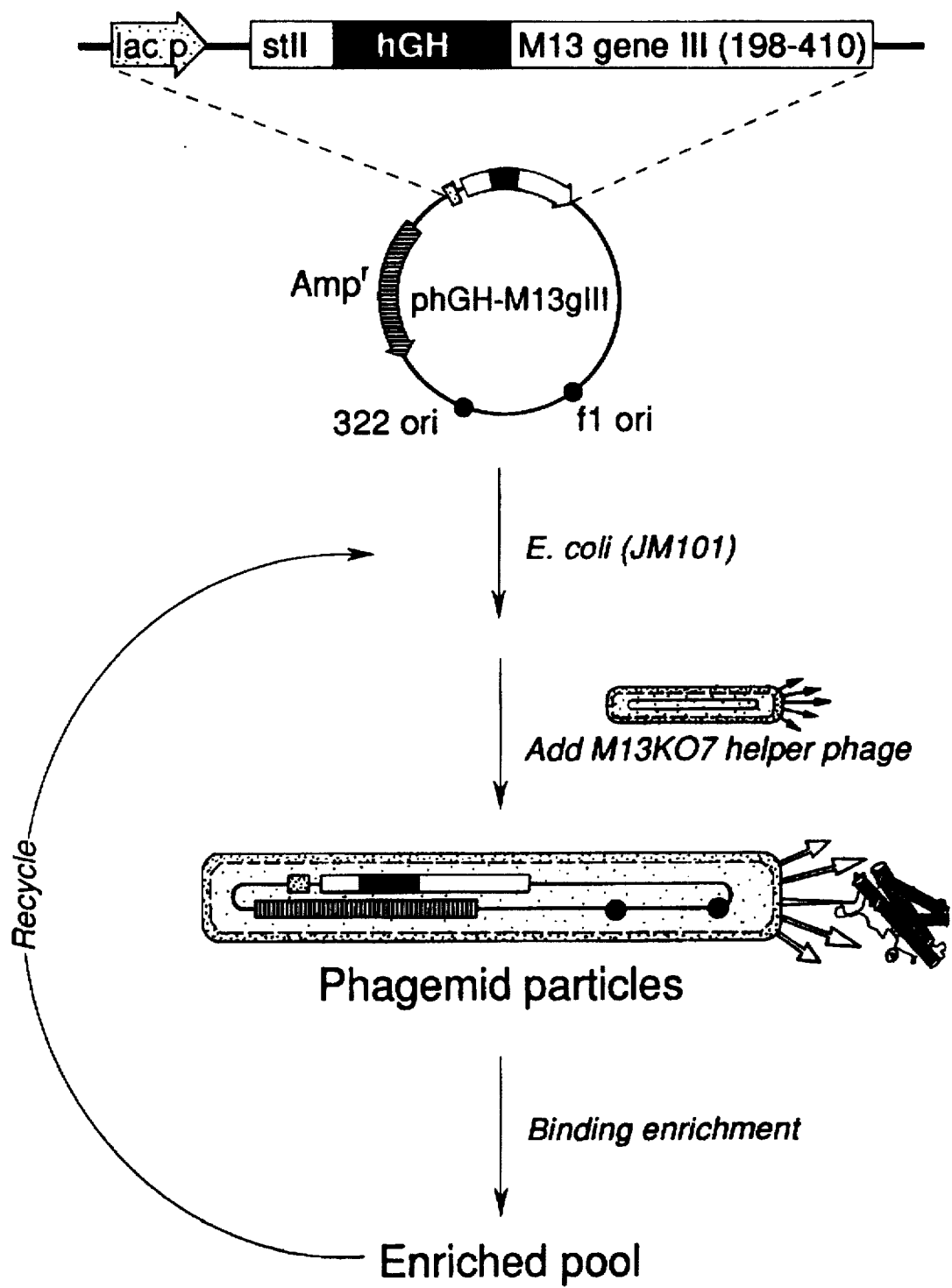
FIG. 1. Strategy for displaying large proteins on the surface of filamentous phage and enriching for altered receptor binding properties. A plasmid, phGH-M13gIII was constructed that fuses the entire coding sequence of hGH to the carboxyl terminal domain of M13 gene III. Transcription of the fusion protein is under control of the IAC promoter/operator sequence, and secretion is directed by the stII signal sequence. Phagemid particles are produced by infection with the "helper" phage, M13KO7, and particles displaying hGH can be enriched by binding to an affinity matrix containing the hGH receptor. The wild-type gene III (derived from the M13KO7 phage) is diagramed by 4-5 copies of the multiple arrows on the tip of the phage, and the fusion protein (derived from the phagemid, phGH-M13gIII) is indicated schematically by the folding diagram of hGH replacing the arrow head.

The following discussion will be best understood by referring to FIG. 1. In its simplest form, the method of the instant invention comprises a method for selecting novel binding polypeptides, such as protein ligands, having a desired, usually high, affinity for a target molecule from a library of structurally related binding polypeptides. The library of structurally related polypeptides, fused to a phage coat protein, is produced by mutagenesis and, preferably, a single copy of each related polypeptide is displayed on the surface of a phagemid particle containing DNA encoding that polypeptide. These phagemid particles are then contacted with a target molecule and those particles having the highest affinity for the target are separated from those of lower affinity. The high affinity binders are then amplified by infection of a bacterial host and the competitive binding step is repeated. This process is reiterated until polypeptides of the desired affinity are obtained.

The novel binding polypeptides or ligands produced by the method of this invention are useful per se as diagnostics or therapeutics (eg. agonists or antagonists) used in treatment of biological organisms. Structural analysis of the selected polypeptides may also be used to facilitate rational drug design.

By "binding polypeptide" as used herein is meant any polypeptide that binds with a selectable affinity to a target molecule. Preferably the polypeptide will be a protein that most preferably contains more than about 100 amino acid residues. Typically the polypeptide will be a hormone or an antibody or a fragment thereof.

By "high affinity" as used herein is meant an affinity constant ($K_d$) of $<10^{-5}M$ and preferably $<10^{-7}M$ under physiological conditions.

By "target molecule" as used herein is meant any molecule, not necessarily a protein, for which it is desirable to produce a ligand. Preferably, however, the target will be a protein and most preferably the target will be a receptor, such as a hormone receptor.

By "humanized antibody" as used herein is meant an antibody in which the complementarity-determining regions (CDRs) of a mouse or other non-human antibody are grafted onto a human antibody framework. By human antibody framework is meant the entire human antibody excluding the CDRs.

I. CHOICE OF POLYPEPTIDES FOR DISPLAY ON THE SURFACE OF A PHAGE

The first step in the method of this invention is to choose a polypeptide having rigid secondary structure exposed to the surface of the polypeptide for display on the surface of a phage.

By "polypeptide" as used herein is meant any molecule whose expression can be directed by a specific DNA sequence. The polypeptides of this invention may comprise more than one subunit, where each subunit is encoded by a separate DNA sequence.

By "rigid secondary structure" as used herein is meant any polypeptide segment exhibiting a regular repeated structure such as is found in; α-helices, $3_{10}$ helices, π-helices, parallel and antiparallel β-sheets, and reverse turns. Certain "non-ordered" structures that lack recognizable geometric order are also inclued in the definition of rigid secondary structure provided they form a domain or "patch" of amino acid residues capable of interaction with a target and that the overall shape of the structure is not destroyed by replacement of an amino acid within the structure. It is believed that some non-ordered structures are combinations of reverse turns. The geometry of these rigid secondary structures is well defined by $\phi$ and $\psi$ torsional angles about the α-carbons of the peptide "backbone".

The requirement that the secondary structure be exposed to the surface of the polypeptide is to provide a domain or "patch" amino acid residues that can be exposed to and bind with a target molecule. It is primarily these amino acid residues that are replaced by mutagenesis that form the "library" of structurally related (mutant) binding polypeptides that are displayed on the surface of the phage and from which novel polypeptide ligands are selected. Mutagenesis or replacement of amino acid residues directed toward the interior of the polypeptide is generally avoided so that the overall structure of the rigid secondary structure is preserved. Some replacement of amino acids on the interior region of the rigid secondary structures, especially with hydrophobic amino acid residues, may be tolerated since these conservative substitutions are unlikely to distort the overall structure of the polypeptide.

Repeated cycles of "polypeptide" selection are used to select for higher and higher affinity binding by the phagemid selection of multiple amino acid changes which are selected by multiple selection cycles. Following a first round of phagemid selection, involving a first region or selection of amino acids in the ligand polypeptide, additional rounds of phagemid selection in other regions or amino acids of the ligand polypeptide are conducted. The cycles of phagemid selection are repeated until the desired affinity properties of the ligand polypeptide are achieved. To illustrate this process, Example VIII phagemid selection of hGH was conducted in cycles. In the first cycle hGH amino acids 172, 174, 176 and 178 were mutated and phagemid selected. In a second cycle hGH amino acids 167, 171, 175 and 179 were phagemid selected. In a third cycle hGH amino acids 10, 14, 18 and 21 were phagemid selected. Optimum amino acid changes from a previous cycle may be incorporated into the polypeptide before the next cycle of selection. For example, hGH amino acids substitution 174 (serine) and 176 (tyrosine) were incorporated into the hGH before the phagemid selection of hGH amino acids 167, 171, 175 and 179.

Figures 2A, 2B:
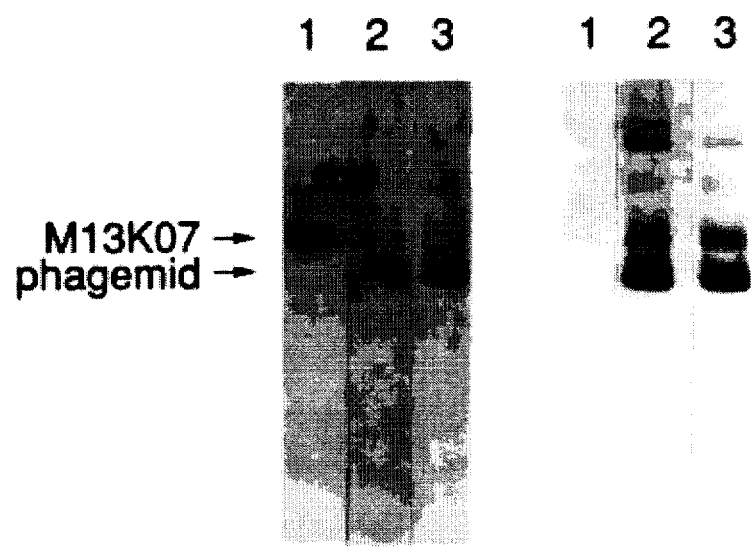
FIG. 2. Immunoblot of whole phage particles shows that hGH comigrates with phage. Phagemid particles purified in a cesium chloride gradient were loaded into duplicate wells and electrophoresed through a 1% agarose gel in 375 mM Tris, 40 mM glycine pH 9.6 buffer. The gel was soaked in transfer buffer (25 mM tris, pH 8.3, 200 mM glycine, 20% methanol) containing 2% SDS and 2% β-mercaptoethanol for 2 hours, then rinsed in transfer buffer for 6 hours. The proteins in the gel were then electroblotted onto immobilon membranes (Millipore). The membrane containing one set of samples was stained with Coomassie blue to show the position of the phase proteins (A). The duplicate membrane was immuno-stained for hGH by reacting the membrane with polyclonal rabbit anti-hGH antibodies followed by reaction with horseradish peroxidase conjugated goat anti-rabbit IgG antibodies (B). Lane 1 contains the M13KO7 parent phage and is visible only in the Coomassie blue stained membrane, since it lacks hGH. Lanes 2 and 3 contain separate preparation of the hormone phagemid particles which is visible both by Coomassie and hGH immuno-staining. The difference in migration distance between the parent M13KO7 phage and hormone phagemid particles reflects the different size genomes that are packaged within (8.7 kb vs. 5.1 kb, respectively).

From the forgoing it will be appreciated that the amino acid residues that form the binding domain of the polypeptide will not be sequentially linked and may reside on different subunits of the polypeptide. That is, the binding domain tracks with the particular secondary structure at the binding site and not the primary structure. Thus, generally, mutations will be introduced into codons encoding amino acids with a particular secondary structure at sites directed away from the interior of the polypeptide so that they will have the potential to interact with the target. By way of illustration, FIG. 2 shows the location of residues in hGH that are known to strongly modulate its binding to the hGH-binding protein (Cunningham et al., *Science* 247:1461–1465 [1990]). Thus representative sites suitable for mutagenesis would include residues 172, 174, 176, and 178 on helix-4, as well as residue 64 located in a "non-ordered" secondary structure.

There is no requirement that the polypeptide chosen as a ligand to a target normally bind to that target. Thus, for example, a glycoprotein hormone such as TSH can be chosen as a ligand for the FSH receptor and library of mutant TSH molecules are employed in the method of this invention to produce novel drug candidates.

This invention thus contemplates any polypeptide that binds to a target molecule, and includes antibodies. Preferred polypeptides are those that have pharmaceutical utility. More preferred polypeptides include; a growth hormone, including human growth hormone, des-N-methionyl human growth hormone, and bovine growth hormone; parathyroid hormone; thyroid stimulating hormone; thyroxine; insulin A-chain; insulin B-chain; proinsulin; follicle stimulating hormone; calcitonin; leutinizing hormone; glucagon; factor VIII; an antibody; lung surfactant; a plasminogen activator, such as urokinase or human tissue-type plasminogen activator (t-PA); bombesin; factor IX, thrombin; hemopoietic growth factor; tumor necrosis factor-alpha and -beta; enkephalinase; a serum albumin such as human serum albumin, mullerian-inhibiting substance; relaxin A-chain; relaxin B-chain; prorelaxin; mouse gonadotropin-associated peptide; a microbial protein, such as betalactamase; tissue factor protein; inhibin; activin; vascular endothelial growth factor; receptors for hormones or growth factors; integrin; thrombopoietin; protein A or D; rheumatoid factors; nerve growth factor such as NGF-β; platelet-derived growth factor; fibroblast growth factor such as αFGF and βFGF; epidermal growth factor; transforming growth factor (TGF) such as TGF-alpha and TGF-beta; insulin-like growth factor-I and -II; insulin-like growth factor binding proteins; CD-4; CNase; latency associated peptide; erythropoietin; osteoinductive factors; an interferon such as interferon-alpha, -beta, and -gamma; colony stimulating factors (CSFs), e.g., M-CSF, GM-CSF, and G-CSF; interleukins (ILs), e.g., IL-1, IL-2, IL-3, IL-4, etc.; superoxide dismutase; decay accelerating factor; atrial natriuretic peptides A, B or C; viral antigen such as; for example, a portion of the HIV envelope; immunoglobulins; and fragments of any of the above-listed polypeptides. In addition, one or more predetermined amino acid residues on the polypeptide may be substituted, inserted, or deleted, for example, to produce products with improved biological properties. Further, fragments of these polypeptides, especially biologically active fragments, are included. Yet more preferred polypeptides of this invention are human growth hormone, and atrial naturetic peptides A, B, and C, endotoxin, subtilisin, trypsin and other serine proteases.

Still more preferred are polypeptide hormones that can be defined as any amino acid sequence produced in a first cell that binds specifically to a receptor on the same cell type (autocrine hormones) or a second cell type (non-autocrine) and causes a physiological response characteristic of the receptor-bearing cell. Among such polypeptide hormones are cytokines, lymphokines, neurotrophic hormones and adenohypophyseal polypeptide hormones such as growth hormone, prolactin, placental lactogen, luteinizing hormone, follicle-stimulating hormone, thyrotropin, chorionic gonadotropin, corticotropin, α or β-melanocyte-stimulating hormone, β-lipotropin, γ-lipotropin and the endorphins; hypothalmic release-inhibiting hormones such as corticotropin-release factor, growth hormone release-inhibiting hormone, growth hormone-release factor; and other polypeptide hormones such as atrial natriuretic peptides A, B or C.

II. OBTAINING A FIRST GENE (GENE 1) ENCODING THE DESIRED POLYPEPTIDE

The gene encoding the desired polypeptide (i.e., a polypeptide with a rigid secondary structure) can be obtained by methods known in the art (see generally, Sambrook et al., *Molecular Biology: A laboratory Manual*, Cold Spring Harbor Press, Cold Spring Harbor, N.Y. [1989]). If the sequence of the gene is known, the DNA encoding the gene may be chemically synthesized (Merrfield, *J. Am. Chem. Soc.*, 85:2149 [1963]). If the sequence of the gene is not known, or if the gene has not previously been siolated, it may be cloned from a cDNA library (made from RNA obtained from a suitable tissue in which the desired gene is expressed) or from a suitable genomic DNA library. The gene is then isolated using an appropriate probe. For cDNA libraries, suitable probes include monoclonal or polyclonal antibodies (provided that the cDNA library is an expression library), oligonucleotides, and complementary or homologous cDNAs or fragments thereof. The probes that may be used to isolate the gene of interest from genomic DNA libraries include cDNAs or fragments there of that encode the same or a similar gene, homologous genomic DNAs or DNA fragments, and oligonucleotides. Screening the cDNA or genomic library with the selected probe is conducted using standard procedures as described in chapters 10–12 of Sambrook et al., supra.

An alternative means to isolating the gene encoding the protein of interest is to use polymerase chain reaction methodology (PCR) as described in section 14 of Sambrook et al., supra. This method requires the use of oligonucleotides that will hybridize to the gene of interest; thus, at least some of the DNA sequence for the gene must be known in order to generate the oligonucleotides.

After the gene has been isolated, it may be inserted into a suitable vector (preferably a plasmid) for amplification, as described generally in Sambrook et al., supra.

III. CONSTRUCTING REPLICABLE EXPRESSION VECTORS

While several types of vectors are available and may be used to practice this invention, plasmid vectors are the preferred vectors for use herein, as they may be constructed with relative ease, and can be readily amplified. Plasmid vectors generally contain a variety of components including promoters, signal sequences, phenotypic selection genes, origin of replication sites, and other necessary components as are known to those of ordinary skill in the art.

Promoters most commonly used in prokaryotic vectors include the lac Z promoter system, the alkaline phosphatase pho A promoter, the bacteriophage λPL promoter (a temperature senstive promoter), the tac promoter (a hybrid trp-lac promoter that is regulated by the lac repressor), the tryptophan promoter, and the bacteriophage T7 promoter. For general descriptions of promoters, see section 17 of Sambrook et al. supra. While these are the most commonly used promoters, other suitable microbial promoters may be used as well.

Preferred promoters for practicing this invention are those that can be tightly regulated such that expression of the fusion gene can be controlled. It is believed that the problem that went unrecognized in the prior art was that display of multiple copies of the fusion protein on the surface of the phagemid particle lead to multipoint attachment of the phagemid with the target. It is believed this effect, referred to as the "chelate effect", results in selection of false "high affinity" polypeptides when multiple copies of the fusion protein are displayed on the phagemid particle in close proximity to one another so that the target was "chelated". When multipoint attachment occurs, the effective or apparent Kd may be as high as the product of the individual Kds for each copy of the displayed fusion protein. This effect may be the reason Cwirla and coworkers supra were unable to separate moderate affinity peptides from higher affinity peptides.

It has been discovered that by tightly regulating expression of the fuson protein so that no more than a minor amount, i.e. fewer than about 1%, of the phagemid particles contain multiple copies of the fusion protein the "chelate effect" is overcome allowing proper selection of high affinity polypeptides. Thus, depending on the promoter, culturing conditions of the host are adjusted to maximize the number of phagemid particles containing a single copy of the fusion protein and minimize the number of phagemid particles containing multiple copies of the fusion protein.

Preferred promoters used to practice this invention are the lac Z promoter and the pho A promoter. The lac Z promoter is regulated by the lac repressor protein lac i, and thus transcription of the fusion gene can be controlled by manipulation of the level of the lac repressor protein. By way of illustration, the phagemid containing the lac Z promoter is grown in a cell strain that contains a copy of the lac i repressor gene, a repressor for the lac Z promoter. Exemplary cell strains containing the lac i gene include JM 101 and XL1-blue. In the alternative, the host cell can be contransfected with a plasmid containing both the repressor lac i and the lac Z promoter. Occasionally both of the above techniques are used simultaneously, that is, phagemide particles containing the lac Z promoter are grown in cell strains containing the lac i gene and the cell strains are contransfected with a plasmid containing both the lac Z and lac i genes. Normally when one wishes to express a gene, to the transfected host above one would add an inducer such as isopropylthiogalactoside (IPTG). In the present invention however, this step is omitted to (a) minimize the expression of the gene III fusion protein thereby minimizing the copy number (i.e. the number of gene III fusions per phagemid number) and to (b) prevent poor or improper packaging of the phagemid caused by inducers such as IPTG even at low concentrations. Typically, when no inducer is added, the number of fusion proteins per phagemid particle is about 0.1 (number of bulk fusion proteins/number of phagemid particles). The most preferred promoter used to practice this invention is pho A. This promoter is believed to be regulated by the level of inorganic phosphate in the cell where the phosphate acts to down-regulate the activity of the promoter. Thus, by depleting cells of phosphate, the activity of the promoter can be increased. The desired result is achieved by growing cells in a phosphate enriched medium such as 2YT or LB thereby controlling the expression of the gene III fusion.

One other useful component of vectors used to practice this invention is a signal sequence. This sequence is typically located immediately 5' to the gene encoding the fusion protein, and will thus be transcribed at the amino terminus of the fusion protein. However, in certain cases, the signal sequence has been demonostrated to be located at positions other 5' to the gene encoding the protein to be secreted. This sequence targets the protein to which it is attached across the inner membrane of the bacterial cell. The DNA encoding the signal sequence may be obtained as a restriction endonuclease fragment from any gene encoding a protein that has a signal sequence. Suitable prokaryotic signal sequences may be obtained from genes encoding, for example, LamB or OmpF (Wong et al., Gene, 68:193 [1983]), MalE, PhoA and other genes. A preferred prokaryotic signal sequence for practicing this invention is the E. coli heat-stable enterotoxin II (STII) signal sequence asdescribed by Chang et al., Gene 55:189 [1987].

Another useful component of the vectors used to practice this invention is phenotypic selection genes. Typical phenotypic selection genes are those encoding proteins that confer antibiotic resistance upon the host cell. By way of illustration, the ampicillin resistance gene (amp), and the tetracycline resistance gene (tet) are readily employed for this purpose.

Construction of suitable vectors comprising the aforementioned components as well as the gene encoding the desired polypeptide (gene 1) are prepared using standard recombinant DNA procedures as described in Sambrook et al. supra. Isolated DNA fragments to be combined to form the vector are cleaved, tailored,and ligated together in a specific order and orientation to generate the desired vector.

The DNA is cleaved using the appropriate restriction enzyme or enzymes in a suitable buffer. In general, about 0.2–1 μg of plasmid or DNA fragments is used with about 1–2 units of the appropriate restriction enzyme in about 20 μl of buffer solution. Appropriate buffers, DNA concentrations, and incubation times and temperatures are specified by the manufacturers of the restriction enzymes. Generally, incubation times of about one or two hours at 37° C. are adequate, although several enzymes require higher temperatures. After incubation, the enzymes and other contaminants are removed by extraction of the digestion solution with a mixture of phenol and chloroform, and the DNA is recovered from the aqueous fraction by precipitation with ethanol.

To ligate the DNA fragments together to form a functional vector, the ends of the DNA fragments must be compatible with each other. In some cases, the ends will be directly compatible after endonuclease digestion. However, it may be necessary to first convert the sticky ends commonly produced by endonuclease digestion to blunt ends to make them compatible for ligation. To blunt the ends, the DNA is treated in a suitable buffer for at least 15 minutes at 15° C. with 10 units of of the Klenow fragment of DNA polymerase I (Klenow) in the presence of the four deoxynucleotide triphosphates. The DNA is then purified by phenol-chloroform extraction and ethanol precipitation.

The cleaved DNA fragments may be size-separated and selected using DNA gel electrophoresis. The DNA may be electrophoresed through either an agarose or a polyacrylamide matrix. The selection of the matrix will depend on the size of the DNA fragments to be separated. After electrophoresis, the DNA is extracted from the matrix by electroelution, or, if low-melting agarose has been used as the matrix, by melting the agarose and extracting the DNA from it, as described in sections 6.30–6.33 of Sambrook et al., supra.

The DNA fragments that are to be ligated together (previously digested with the appropriate restriction enzymes such that the ends of each fragment to be ligated are compatible) are put in solution in about equimolar amounts. The solution will also contain ATP, ligase buffer and a ligase such as T4 DNA ligase at about 10 units per 0.5 μg of DNA. If the DNA fragment is to be ligated into a vector, the vector is at first linearized by cutting with the appropriate restriction endonuclease(s). The linearized vector is then treated with alkaline phosphatase or calf intestinal phosphatase. The phosphatasing prevents self-ligation of the vector during the ligation step.

After ligation, the vector with the foreign gene now inserted is transformed into a suitable host cell. Prokaryotes are the preferred host cells for this invention. Suitable prokaryotic host cells include E coli strain JM101, E. coli K12 strain 294 (ATCC number 31,466), E. coli strain W3110 (ATCC number 27,325), E. coli X1776 (ATCC number 31,537), E. coli XL-1Blue (stratagene), and E. coli B; however many other strains of E. coli, such as HB101, NM522, NM538, NM539, and many other species and genera of prokaryotes may be used as well. In addition to the E. coli strains listed above, bacilli such as Bacillus subtilis, other enterobacteriaceae such as Salmonella trphimurium or Serratia marcesans, and various Pseudomonas species may all be used as hosts.

Transformation of prokaryotic cells is readily accomplished using the calcium chloride method as described in section 1.82 of Sambrook et al., supra. Alternatively, electroporation (Neumann et al., EMBO J., 1:841 [1982]) may be used to transform these cells. The transformed cells are selected by growth on an antibiotic, commonly tetracycline (tet) or ampicillin (amp), to which they are rendered resistant due to the presence of tet and/or amp resistance genes on the vector.

After selection of the transformed cells, these cells are grown in culture and the plasmid DNA (or other vector with the foreign gene inserted) is then isolated. Plasmid DNA can be isolated using methods known in the art. Two suitable methods are the small scale preparation of DNA and the large-scale preparation of DNA as described in sections 1.25–1.33 of Sambrook et al., supra. The isolated DNA can be purified by methods known in the art such as that described in section 1.40 of Sambrook et al., supra. This purified plasmid DNA is then analyzed by restriction mapping and/or DNA sequencing. DNA sequencing is generally performed by either the method of Messing et al. Nucleic Acids Res., 9:309 [1981] or by the method of Maxam et al. Meth. Enzymol., 65:499 [1980].

IV. GENE FUSION

This invention contemplates fusing the gene enclosing the desired polypeptide (gene 1) to a second gene (gene 2) such that a fusion protein is generated during transcription. Gene 2 is typically a coat protein gene of a phage, and preferably it is the phage M13 gene III coat protein, or a fragment thereof. Fusion of genes 1 and 2 may be accomplished by inserting gene 2 into a particular site on a plasmid that contains gene 1, or by inserting gene 1 into a particular site on a plasmid that contains gene 2.

Insertion of a gene into a plasmid requires that the plasmid be cut at the precise location that the gene is to be inserted. Thus, there must be a restriction endonuclease site at this location (preferably a unique site such that the plasmid will only be cut at a single location during restriction endonuclease digestion). The plasemid is digested, phosphatased, and purified as described above. The gene is then inserted into this linearized plasmid by ligating the two DNAs together. Ligation can be accomplished if the ends of the plasmid are compatible with the ends of the gene to be inserted. If the restriction enzymes are used to cut the plasmid and isolate the gene to be inserted create blunt ends or compatible sticky ends, the DNAs can be ligated together directly using a ligase such as bacteriophage T4 DNA ligase and incubating the mixture at 16° C. for 1–4 hours in the presence of ATP and ligase buffer as described in section 1.68 of Sambrook et al., supra. If the ends are not compatible, they must first be made blunt by using the Klenow fragment of DNA polymerase I or bacteriophage T4 DNA polymerase, both of which require the four deoxyribonucleotide triphosphates to fill-in overhanging single-stranded ends of the digested DNA. Alternatively, the ends may be blunted using a nuclease such as nuclease S1 or mung-bean nuclease, both of which function by cutting back the overhanging single strands of DNA. The DNA is then religated using a ligase as described above. In some cases, it may not be possible to blunt the ends of the gene to be inserted, as the reading frame of the coding region will be altered. To overcome this problem, oligonucleotide linkers may be used. The linkers serve as a bridge to connect the plasmid to the gene to be inserted. These linkers can be made synthetically as double stranded or single stranded DNA using standard methods. The linkers have one end that is compatible with the ends of the gene to be inserted; the linkers are first ligated to this gene using ligation methods described above. The other end of the linkers is designed to be compatible with the plasmid for ligation. In designing the linkers, care must be taken to not destroy the reading frame of the gene to be inserted or the reading frame of the gene contained on the plasmid. In some cases, it may be necessary to design the linkers such that they code for part of an amino acid, or such that they code for one or more amino acids.

Between gene 1 and gene 2, DNA encoding a termination codon may be inserted, such termination codons are UAG (amber), UAA (ocher) and UGA (opel). (Microbiology, Davis et al. Harper & Row, New York, 1980, pages 237, 245–47 and 274). The termination codon expressed in a wild type host cell results in the synthesis of the gene 1 protein product without the gene 2 protein attached. However, growth in a suppressor host cell results in the synthesis of detectable quantities of fused protein. Such suppressor host cells contain a tRNA modified to insert an amino acid in the termination codon position of the mRNA thereby resulting in production of detectible amounts of the fusion protein. Such suppressor host cells are well known and described, such as E. coli suppressor strain (Bullock et al., Bio Techniques 5, 376–379 [1987]). Any acceptable method may be used to place such a termination codon into the mRNA encoding the fusion polypeptide.

The suppressible codon may be inserted between the first gene encoding a polypeptide, and a second gene encoding at least a portion of a phage coat protein. Alternatively, the suppressible termination codon may be inserted adjacent to the fusion site by replacing the last amino acid triplet in the polypeptide or the first amino acid in the phage coat protein.

When the phagemid containing the suppressible codon is grown in a suppressor host cell, it results in the detectable production of a fusion polypeptide containing the polypeptide and the coat protein. When the phagemid is grown in a non-suppressor host cell, the polypeptide is synthesized substantially without fusion to the phage coat protein due to termination at the inserted suppressible triplet encoding UAG, UAA, or UGA. In the non-suppressor cell the polypeptide is synthesized and secreted from the host cell due to the absence of the fused phage coat protein which otherwise anchored it to the host cell.

V. ALTERATION(MUTATION) OF GENE 1 AT SELECTED POSITIONS

Gene 1, encoding the desired polypeptide, may be altered at one or more selected codons. An alteration is defined as a substitution, deletion, or insertion of one or more codons in the gene encoding the polypeptide that results in a change in the amino acid sequence of the polypeptide as compared with the unaltered or native sequence of the same polypeptide. Preferably, the alterations will be by substitution of at least one amino acid with any other amino acid in one or more regions of the molecule. The alterations may be produced by a variety of methods known in the art. These methods include but are not limited to oligonucleotide-mediated mutagenesis and cassette mutagenesis.

A. Oligonucleotide-Mediated Mutagenesis

Oligonucleotide-mediated mutagenesis is preferred method for preparing substitution, deletion, and insertion variants of gene 1. This technique is well known in the art as described by Zoller et al. Nucleic Acids Res. 10:6487–6504 [1987]. Briefly, gene 1 is altered by hybridizing an oligonucleotide encoding the desired mutation to a DNA template, where the template is the single-stranded form of the plasmid containing the unaltered or native DNA sequence of gene 1. After hybridization, a DNA polymerase is used to synthesize an entire second complementary strand of the template will thus incorporate the oligonucleotide primer, and will code for the selected alteration in gene 1.

Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al. *Proc. Nat'l. Acad. Sci. USA* 75:5765 [1978].

The DNA template can only be generated by those vectors that are either derived from bacteriophage M13 vectors (the commercially available M13mp18 and M13mp19 vectors are suitable), or those vectors that contain a single-stranded phage origin of replication as described by Viera et al. *Meth. Enzymol.*, 153:3 [1987]. Thus, the DNA that is to be mutated must be inserted into one of these vectors in order to generate single-stranded template. Production of the single-stranded template is described in sections 4.21–4.41 of Sambrook et al., supra.

To alter the native DNA sequence, the oligonucleotide is hybridized to the single stranded template under suitable hybridization conditions. A DNA polymerizing enzyme, usually the Klenow fragment of DNA polymerase I, is then added to synthesize the complementary strand of the template using the oligonucleotide as a primer for synthesis. A heteroduplex molecule is thus formed such that one strand of DNA encodes the mutated form of gene 1, and the other strand (the original template) encodes the native, unaltered sequence of gene 1. This heteroduplex molecule is then transformed into a suitable host cell, usually a prokaryote such as *E. Coli* JM101. After growing the cells, they are plated onto agarose plates and screened using the oligonucleotide primer radiolabelled with 32-Phosphate to identify the bacterial colonies that contain the mutated DNA.

The method described immediately above may be modified such that a homoduplex molecule is created wherein both strands of the plasmid contain the mutation(s). The modifications are as follows: The single-stranded oligonucleotide is annealed to the single-stranded template as described above. A mixture of three deoxyribonucleotides, deoxyriboadenosine (dATP), deoxyriboguanosine (dGTP), and deoxyribothymidine (dTTP), is combined with a modified thio-deoxyribocytosine called dCTP-(aS) (which can be obtained from Amersham). This mixture is added to the template-oligonucleotide complex. Upon addition of DNA polymerase to this mixture, a strand of DNA identical to the template except for the mutated bases is generated. In addition, this new strand of DNA will contain dCTP-(aS) instead of dCTP, which serves to protect it from restriction endonuclease digestion. After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell such as *E. coli* JM101, as described above.

Mutants with more than one amino acid to be substituted may be generated in one of several ways. If the amino acids are located close together in the polypeptide chain, they may be mutated simultaneously using one oligonucleotide that codes for all of the desired amino acid substitutions. If, however, the amino acids are located some distance from each other (separated by more than about ten amino acids), it is more difficult to generate a single oligonucleotide that encodes all of the desired changes. Instead, one of two alternative methods may be employed.

In the first method, a separate oligonucleotide is generated for each amino acid to be substituted. The oligonucleotides are then annealed to the single-stranded template DNA simultaneously, and the second strand of DNA that is synthesized from the template will encode all of the desired amino acid substitutions. The alternative method involves two or more rounds of mutagenesis to produce the desired mutant. The first round is as described for the single mutants: wild-type DNA is used for the template, an oligonucleotide encoding the first desired amino acid substitution(s) is annealed to this template, and the heteroduplex DNA molecule is then generated. The second round of mutagenesis utilizes the mutated DNA produced in the first round of mutagenesis as the template. Thus, this template already contains one or more mutations. The oligonucleotide encoding the additional desired amino acid substitution(s) is then annealed to this template, and the resulting strand of DNA now encodes mutations from both the first and second rounds of mutagenesis. This resultant DNa can be used as a template in a third round of mutagenesis, and so on.

B. Cassette Mutagenesis

This method is also a preferred method for preparing substitution, deletion, and insertion variants of gene 1. The method is based on that described by Wells et al. *Gene*, 34:315 [1985]. The starting material is the plasmid (or other vector) comprising gene 1, the gene to be mutated. The codon(s) in gene 1 to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in gene 1. After the restriction sites have been introduced into the plasmid, the plasmid is cut at these sites to linearize it. A double-stranded oligonucleotide encoding the sequence of the DNA between the restriction sites but containing the desired mutation(s) is synthesized using standard procedures. The two strands are synthesized separately and then hybridized together using standard techniques. This double-stranded oligonucleotide is referred to as the cassette. This cassette is designed to have 3' and 5' ends that are compatible with the ends of the linearized plasmid, such that it can be directly ligated to the plasmid. This plasmid now contains the mutated DNA sequence of Gene 1.

VI OBTAINING DNA ENCODING THE DESIRED PROTEIN

In an alternative embodiment, this invention contemplates production of variants of a desired protein containing one or more subunits. Each subunit is typically encoded by separate gene. Each gene encoding each subunit can be obtained by methods known in the art (see, for example, Section II). In some instances, it may be necessary to obtain the gene encoding the various subunits using separate techniques selected from any of the methods described in Section II.

When constructing a replicable expression vector where the protein of interest contains more than one subunit, all subunits can be regulated by the same promoter, typically located 5' to the DNA encoding the subunits, or each may be regulated by separate promoter suitably oriented in the vector so that each promoter is operably linked to the DNA it is intended to regulate. Selection of promoters is carried out as described in Section III above.

In constructing a replicable expression vector containing DNA encoding the protein of interest having multiple subunits, the reader is referred to FIG. 10 where, by way of illustration, a vector is diagrammed showing DNA encoding each subunit of an antibody fragment. This figure shows that, generally, one of the subunits of the protein of interest will be fused to a phage coat protein such as M13 gene III. This gene fusion generally will contain its own signal sequence. A separate gene encodes the other subunit or subunits, and it is apparent that each subunit generally has its own signal sequence. FIG. 10 also shows that a single promoter can regulate the expression of both subunits. Alternatively, each subunit may be independently regulated by a different promoter. The protein of interest subunit-phage coat protein fusion construct can be made as described in Section IV above.

When constructing a family of variants of the desired multi-subunit protein, DNA encoding each subunit in the vector may mutated in one or more positions in each subunit. When multi-subunit antibody variants are constructed, preferred sites of mutagenesis correspond to codons encoding amino acid residues located in the complementarity-determining regions (CDR) of either the light chain, the heavy chain, or both chains. The CDRs are commonly referred to as the hypervariable regions. Methods for mutagenizing DNA encoding each subunit of the protein of interest are conducted essentially as described in Section V above.

VII PREPARING A TARGET MOLECULE AND BINDING WITH PHAGEMID

Target proteins, such as receptors, may be isolated from natural sources or prepared by recombinant methods by procedures known in the art. By way of illustration, glycoprotein hormone receptors may be prepared by the technique described by McFarland et al., *Science* 245:494–499 [1989], nonglycosylated forms expressed in *E. coli* are described by Fuh et al., *J. Biol. Chem* 265:3111–3115 [1990]. Other receptors can be prepared by standard methods.

The purified target protein may be attached to a suitable matrix such as agarose beads, acrylamide beads, glass beads, cellulose, various acrylic copolymers, hydroxyalkyl methacrylate gels, polyacrylic and polymethacrylic copolymers, nylon, neutral and ionic carriers, and the like. Attachment of the target protein to the matrix may be accomplished by methods described in *Methods in Enzymology*, 44 [1976], or by other means known in the art.

After attachment of the target protein to the matrix, the immobilized target is contacted with the library of phagemid particles under conditions suitable for binding of at least a portion of the phagemid particles with the immobilized target. Normally, the conditions, including pH, ionic strength, temperature and the like will mimic physiological conditions.

Bound phagemid particles ("binders") having high affinity for the immobilized target are separated from those having a low affinity (and thus do not bind to the target) by washing. Binders may be dissociated from the immobilized target by a variety of methods. These methods include competitive dissociation using the wild-type ligand, altering pH and/or ionic strength, and methods known in the art.

Suitable host cells are infected with the binders and helper phage, and the host cells are cultured under conditions suitable for amplification of the phagemid particles. The phagemid particles are then collected and the selection process is repeated one or more times until binders having the desired affinity for the target molecule are selected.

Optionally the library of phagemid particles may be sequentially contacted with more than one immobilized target to improve selectivity for a particular target. For example, it is often the case that a ligand such as hGH has more than one natural receptor. In the case of hGH, both the growth hormone receptor and the prolactin receptor bind the hGH ligand. It may be desirable to improve the selectivity of hGH for the growth hormone receptor over the prolactin receptor. This can be achieved by first contacting the library of phagemid particles with immobilized prolactin receptor, eluting those with a low affinity (i.e. lower than wild type hGH) for the prolactin receptor and then contacting the low affinity prolactin "binders" or non-binders with the immobilized growth hormone receptor, and selecting for high affinity growth hormone receptor binders. In thi s case an hGH mutant having a lower affinity for the prolactin receptor would have therapeutic utility even if the affinity for the growth hormone receptor were somewhat lower than that of wild type hGH. This same strategy may be employed to improve selectivity of a particular hormone or protein for its primary function receptor over its clearance receptor.

In another embodiment of this invention, an improved substrate amino acid sequence can be obtained. These may be useful for making better "cut sites" for protein linkers, or for better protease substrates/inhibitors. In this embodiment, an immobilizable molecule (e.g. hGH-receptor, biotin-avidin, or one capable of covalent linkage with a matrix) is fused to gene III through a linker. The linker will preferably be from 3 to 10 amino acids in length and will act as a substrate for a protease. A phagemid will be constructed as described above where the DNA encoding the linker region is randomly mutated to produce a randomized library of phagemid particles with different amino acid sequences at the linking site. The library of phagemid particles are then immobilized on a matrix and exposed to a desired protease. Phagemid particles having preferred or better substrate amino acid sequences in the liner region for the desired protease will be eluted, first producing an enriched pool of phagemid particles encoding preferred linkers. These phagemid particles are then cycled several more times to produce an enriched pool of particles encoding consense sequences(s) (see examples XIII and XIV).

VIII. GROWTH HORMONE VARIANTS AND METHODS OF USE

The cloned gene for hGH has been expressed in a secreted form in *Eschericha cola* (Chang, C. N>, et al., [1987] *Gene* 55, 189) and its DNA and amino acid sequence has been reported (Goeddel, et al. [1979] *Nature* 281, 544; Grey et al., [1985] *Gene* 39, 247). The present invention describes novel hGH variants produced using the phagemid selection methods. Human growth hormone variants containing substitutions at positions 10, 14, 18, 21, 167, 171, 172, 174, 175, 176, 178 and 179 have been described. Those having higher binding affinities are described in Tables VII, XIII and XIV. The amino acid nomenclature for describing the variants is shown below. Growth hormone variants may be administered and formulated in the same manner as regular growth hormone. The growth hormone variants of the present invention may be expressed in any recombinant system which is capable of expressing native or met hGH.

Therapeutic formulations of hGH for therapeutic administration are prepared for storage by mixing hGH having the desired degree of purity with optional physiologically acceptable carriers, excipients, or stabilizers (*Remington's Pharmaceutical Sciences*, 16th edition, Osol, A., Ed., (1980)., in the form of lyophilized cake or aqueous solutions. Acceptable carriers, excipients or stabilizers are nontoxic to recipients at the dosages and concentrations employed, and include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine, or lysine; monosaccharides, disaccharides, and other carbohydrates including glucose, mannose, or dextrins; chelating agents such as EDTA; divalent metal ions such as zinc, cobalt or copper; sugar alcohols such as mannitol or sorbitol; salt-forming counterions such as sodium; and/or nonionic surfactants such as Tween, Pluronics or polyethylene glycol (PEG). Formulations of the present invention may additionally contain a pharmaceutically acceptable buffer, amino acid, bulking agent and/or non-ionic surfactant. These include, for example, buffers, chelating agents, antioxidants, preservatives, cosolvents, and the like; specific examples of these could include, trimethylamine salts ("Tris buffer"), and disodium edetate. The phagemids of the present invention may be used to produce quantities of the hGH variants free of the phage protein. To express hGH variants free of the gene III portion of the fusion, pS0643 and derivatives can simply be grown in a non-suppressor strain such as 16C9. In this case, the amber codon (TAG) leads to termination of translation, which yields free hormone, without the need for an independent DNA construction. The hGH variant is secreted from the host and may be isolated from the culture medium.

One or more of the eight hGH amino acids F10, M14, H18, H21, R167, D171, T175 and I179 may be reped by any amino acid other than the one found in that position in naturally occurring hGH as indicated. Therefore, 1, 2, 3, 4, 5, 6, 7 or all 8 of the indicated amino acids, F10, M14, H18, H21, R167, D171, T175 and I179, may be replaced by any of the other 19 amino acids out of the 20 amino acids listed below. In a preferred embodiment, all eight listed amino acids are replaced by another amino acid. The most preferred eight amino acids to be substituted are indicated in Table XIV in Example XII.

AMINO ACID NOMENCLATURE

Ala (A)
Arg (R)
Asn (N)
Asp (D)
Cys (C)
Gln (Q)
Glu (E)
Gly (G)
His (H)
Ile (I)
Leu (L)
Lys (K)
Met (M)
Phe (F)
Pro (P)
Ser (S)
Thr (T)
Trp (W)
Tyr (Y)
Val (V)

The one letter hGH variant nomenclature first gives the hGH amino acid deleted, for example glutamate 179; then the amino acid inserted; for example, serine; resulting in (E179S).

EXAMPLES

Without further description, it is believed that one of ordinary skill in the art can, using the preceding description and illustrative examples, make and utilize the present invention to the fullest extent. The following working examples therefore specifically point out preferred embodiments of the preset invention, and are not to be construed as limiting in any way of the remainder of the disclosure.

Example 1
Plasmid Constructions and Preparation of hGH-phagemid Particles

The plasmid phGH-M13GIII (FIG. 1), was constructed from M13KO7 and the hGH producing plasmid, pBO473 (Cunningham, B. C., et al., *Science*, 243:1330–1336, [1989]). A synthetic oligonucleotide 5'-AGC-TGT-GGC-TTC-GGG-CCC-TTA-GCA-TTT-AAT-GCG-GTA-3' (SEQ ID NO:2) was used to introduce a unique ApaI restriction site (underlined) into pBO473 after the final Phe191 codon of hGH. The oligonucleotide 5'-TTC-ACA-AAC-GAA-GGG-CCC-CTA-ATT-AAA-GCC-AGA-3' (SEQ ID NO:3) was used to introduce a unique ApaI restriction site (underlined), and a Glu197-to-amber stop codon (bold lettering) into M13KO7 gene III. The oligonucleotide 5' - C A A - T A A - T A A - C G G -

GCT-AGC-CAA-AAG-AAC-TGG-3' (SEQ ID NO:4) introduces a unique NheI site (underlined) after the 3' end of the gene III coding sequence. The resulting 650 base pair (bp) ApaI-NheI fragment from the doubly mutated M13KO7 gene III was cloned into the large ApaI-NheI fragment of pBO473 to create the plasmid, pSO132. This fuses the carboxyl terminus of hGH (Phe191) to the Pro198 residue of the gene III protein with the insertion of a glycine residue encoded from the ApaI site and places the fusion protein under control of the *E. coli* alkaline phosphatase (phoA) promoter and stII secretion signal sequence (Chang, C. N., et al., *Gene*, 55:189–196, [1987]). For inducible expression of the fusion protein in rich media, we replaced the phoA promoter with the lac promoter and operator. A 138 bp EcoRI-XbaI fragment containing the lac promoter, operator, and Cap binding site was produced by PCR of plasmid pUC119 using the oligonucleotides 5'-CACGACA GAATTCCCGACTGGAAA-3' (SEQ ID NO:5) and 5'-CTGTT TCTAGAGTGAAATTGTTA-3' (SEQ ID NO:6) that flank the desired lac sequences and introduce the EcoRI and XbaI restriction sites (underlined). This lac fragment was gel purified and ligated into the large EcoRI-XbaI fragment of pSO132 to create the plasmid, phGH-M13gIII. The sequences of all tailored DNA junctions were verified by the dideoxy sequence method (Sanger, F., et al. *Proc. Natl. Acad. Sci. U.S.A.* 74:5463–5467, [1977]). The R64A variant hGH phagemid was constructed as follows: the NsiI-BGIII mutated fragment of hGH (Cunningham et al. supra) encoding the Arg64 to Ala substitution (R64A) (Cunningham, B.C., Wells, J. A., *Science*, 244:1081–1085, [1989]) was cloned between the corresponding restriction sites in the phGH-M13gIII plasmid (FIG. 1) to replace the wild-type hGH sequence. The R64A hGH phagemid particles were propagated and titered as described below for the wild-type hGH-phagemid.

Plasmids were transformed into a male strain of *E. coli* (JM101) and selected on carbenicillin plates. A single transformant was grown in 2 ml 2YT medium for 4 h at 37° C. and infected with 50 μl of M13KO7 helper phage. The infected culture was diluted into 30 ml 2YT, grown overnight, and phagemid particles were harvested by precipitation with polyethylene glycol (Vierra, J., Messing, J. *Methods in Enzymology*, 153:3–11, [1987]). Typical phagemid particle titers ranged from 2 to 5×10$^{11}$ cfu/ml. The particles were purified to homogeneity by CsCl density centrifugation (Day, L.A. *J. Mol. Biol.*, 39:265–277, [1969]) to remove any fusion protein not attached to virions.

Example II
Immunochemical Analyses of hGH on the Fusion Phage

Rabbit polyclonal antibodies to hGH were pufied with protein A, and coated onto microtiter plates (Nunc) at a concentration of 2 μg/ml in 50 mM sodium carbonate buffer (pH 10) at 4° C. for 16–20 hours. After washing in PBS containing 0.05% Tween 20, hGH or hGH-phagemid particles were serially diluted from 2.0–0.002 nM in buffer A (50 mM tris (pH 7.5), 50 mM NaCl, 2 mM EDTA, 5 mg/ml bovine serum albumin, and 0.05% Tween 20). After 2 hours at room temperature (rt), the plates were washed well and the indicated Mab (Cummingham et al. supra) was added at 1 μg/ml in buffer A for 2 hours at rt. Following washing, horseradish peroxidase conjugated goat anti-mouse IgG antibody was bound at rt for 1 hour. After a final wash, the peroxidase activity was assayed with the substrate, o-phenylenediamine.

Example III
Coupling of the hGH Binding Protein to Polyacrylamide Beads and Binding Enrichments Oxirane polyacrylamide beads (Sigma) were conjugated to the purified extracellular domain of the hGH receptor (hGHbp) (Fuh, G., et al., *J. Biol. Chem.*, 265:3111–3115 [1990]) containing an extra cysteine residue introduced by site-directed mutagenesis at position 237 that does not affect binding of hGH (J. Wells, unpublished). The hGHbp was conjugated as recommended by the supplier to a level of 1.7 pmol hGHbp/mg dry oxirane bead, as measured by binding of [$^{125}$I] hGH to the resin. Subsequently, any unreacted oxirane groups were blocked with BSA and Tris. As a control for non-specific binding of phagemid particles, BSA was similarly coupled to the beads. Buffer for adsorption and washing contained 10 mM Tris-HCl (pH 7.5), 1 mM EDTA, 50 mM NaCl, 1 mg/ml BSA, and 0.02% Tween 20. Elution buffers contained wash buffer plus 200 nM hGH or 0.2M glycine (pH 2.1). Parental phage M13KO7 was mixed with hGH phagemid particles at a ratio of nearly 3000:1 (original mixture) and tumbled for 8–12 h with a 5 μl aliquot (0.2 mg of acrylamide beads) of either absorbent in a 50 μl volume at room temperature. The beads were pelleted by centrifugation and the supernate carefully removed. The beads were resuspended in 200 μl wash buffer and tumbled at room temperature for 4 hours (wash 1). After a second wash (wash 2), the beads were eluted twice with 200 nM hGH for 6–10 hours each (eluate 1, eluate 2). The final elution was with a glycine buffer (pH 2.1) for 4 hours to remove remaining hGH phagemid particles (eluate 3). Each fraction was diluted appropriately in 2YT media, mixed with fresh JM101, incubated at 37° C. for 5 minutes, and plated with 3 ml of 2YT soft agar on LB or LB carbenicillin plates.

Example IV
Construction of hGH-phagemid Particles with a Mixture of Gene III Products The gene III protein is composed of 410 residues dividied into two domains that are separated by a flexible linker sequence (Armstrong, J., et al., *FEBS Lett.*, 135:167–172, [1981]). The amino-terminal domain is required for attachment to the pili of *E. coli*, while the carboxyl-terminal domain is imbedded in the phage coat and required for proper phage assembly (Crissman, J. W., Smith, G. P., *Virology*, 132:445–455, [1984]). The signal sequence and amino-terminal domain of gene III was replaced with the stII signal and entire hGH gene (Chang et al. supra) by fusion to residue 198 in the carboxyl-terminal domain of gene III (FIG. 1). The hGH-gene III fusion was placed under control of the lac promoter/operator in a plasmid (phGH-M13gIII; FIG. 1) containing the pBR322 β-lactamase gene and ColE1 replication origin, and the phage f1 intergenic region. The vector can be easily maintained as a small plasmid vector by selection on carbenicillin, which avoids relying on a functional gene III fusion for propagation. Alternatively, the plasmid can be efficiently packaged into virions (called phagemid particles) by infection with helper phage such as M13KO7 (Viera et al., supra) which avoids problems of phage assembly. Phagemid infectivity titers based upon transduction to carbenicillin resistance in this system varied from 2–5×10$^{11}$ colony forming units (cfu)/ml. The titer of the M13KO7 helper phage in these phagemid stocks is ~10$^{10}$ plaque forming units (pfu)/ml.

With this system we confirmed previous studies (Parmley, Smith supra) that homogeneous expression of large proteins fused to gene III is deleterious to phage production (data not shown). For example, induction of the lac promoter in phGH-M13gIII by addition of IPTG produced low phagemid titers. Moreover, phagemid particles produced by co-infection with M13KO7 containing an amber mutation in gene III gave very low phagemid titers (<$10^{10}$ cfu/ml). We believed that multiple copies of the gene III fusion attached to the phagemid surface could lead to multiple point attachment (the "chelate effect") of the fusion phage to the immobilized target protein. Therefore to control the fusion protein copy number we limited transcription of the hGH-gene III fusion by culturing the plasmid in *E. coli* JM101 (lacI$^Q$) which contains a constitutively high level of the lac repressor protein. The *E. coli* JM 101 cultures containing phGH-M13gIII were best propagated and infected with M13KO7 in the absence of the lac operon inducer (IPTG); however, this system in flexible so that co-expression of other gene III fusion proteins can be balanced. We estimate that about 10% of the phagemid particles contain one copy of the hGH gene III fusion protein from the ratio of the amount of hGH per virion (based on hGH immuno-reactive material in CsCl gradient purified phagemid). Therefore, the titer of fusion phage displaying the hGH gene III fusion is about 2–5×$10^{10}$/ml. This number is much greater than the titer of *E. coli* (~$10^8$ to $10^9$/ml) in the culture from which they are derived. Thus, on average every *E. coli* cell produces 10–100 copies of phage decorated with an hGH gene III fusion protein.

Example V

Structural Integrity of the hGH-gene III Fusion

Immunoblot analysis (FIG. 2) of the hGH-gene III phagemid show that hGH cross-reactive material comigrates with phagemid particles in agarose gels. This indicates that the hGH is tightly associated with phagemid particles. The hGH-gene III fusion protein from the phagemid particles runs as a single immuno-stained band showing that there is little degradation of the hGH when it is attached to gene III. Wild-type gene III protein is clearly present because about 25% of the phagemid particles are infectious. This is comparable to specific infectivity estimates made for wild-type M13 phage that are similarly purified (by CsCl density gradients) and concentrations estimated by UV absorbance (Smith, G. P. supra and Parmley, Smith supra). Thus, both wild-type gene III and the hGH-gene III fusion proteins are displayed in the phage pool.

It was important to confirm that the tertiary structure of the displayed hGH was maintained in order to have confidence that results from binding selections will translate to the native protein. We used monoclonal antibodies (Mabs) to hGH to evaluate the structural integrity of the displayed hGH gene III fusion protein (Table I).

TABLE I

Binding of Eight Different Monoclonal Antibodies (Mab's) to hGH and hGH Phagemid Particles*

| Mab | IC$_{50}$ (nM) hGH | IC$_{50}$ (nM) hGH-phagemid |
|---|---|---|
| 1 | 0.4 | 0.4 |
| 2 | 0.04 | 0.04 |
| 3 | 0.2 | 0.2 |
| 4 | 0.1 | 0.1 |
| 5 | 0.2 | >2.0 |
| 6 | 0.07 | 0.2 |
| 7 | 0.1 | 0.1 |
| 8 | 0.1 | 0.1 |

*Values given represent the concentration (nM) of hGH or hGH-phagemid particles to give half-maximal binding to the particular Mab. Standard errors in these measurements are typically at or below ±30% of the reported value. See Materials and Methods for further details.

The epitopes on hGH for these Mabs have been mapped (Cunningham et al., supra) and binding for 7 of 8 Mabs requires that hGH be properly folded. The IC$_{50}$ values for all Mabs were equivalent to wild-type hGH except for Mab 5 and 6. Both Mabs 5 and 6 are known to have binding determinants near the carboxyl-terminus of hGH which is blocked in the gene III fusion protein. The relative IC$_{50}$ value for Mab1 which reacts with both native and denatured hGH is unchanged compared to the conformationally sensitive Mabs 2–5, 7 and 8. Thus, Mab1 serves as a good internal control for any errors in matching the concentration of the hGH standard to that of the hGH-gene III fusion.

Example VI

Binding Enrichments on Receptor Affinity Beads

Previous workers (Parmley, Smith supra; Scott, Smith supra; Cwirla et al. supra; and Devlin et al. supra) have fractionated phage by panning with streptavidin coated polystyrene petri dishes or microtiter plates. However, chromatographic systems would allow more efficient fractionation of phagemid particles displaying mutant proteins with different binding affinities. We chose non-porous oxirane beads (Sigma) to avoid trapping of phagemid particles in the chromatographic resin. Furthermore, these beads have a small particle size (1 μm) to maximize the surface area to mass ratio. The extracellular domain of the hGH receptor (hGHbp) (Fuh et al., supra) containing a free cysteino residue was efficiently coupled to these beads and phagemid particles showed very low non-specific binding to beads coupled only to bovine serum albumin (Table II).

TABLE II

Specific Binding of Hormone Phage to hGHbp-coated Beads Provides an Enrichment for hGH-phage over M13KO7 Phage*

| Sample | Absorbent‡ | Total pfu | Toal cfu | Ratio (cfu/pfu) | Enrichment§ |
|---|---|---|---|---|---|
| Original mixture† | | 8.3 × $10^{11}$ | 2.9 × $10^8$ | 3.5 × $10^{-4}$ | (1) |
| Supernatant | BSA | 7.4 × $10^{11}$ | 2.8 × $10^8$ | 3.8 × $10^{-4}$ | 1.1 |
| | hGHbp | 7.6 × $10^{11}$ | 3.3 × $10^8$ | 4.3 × $10^{-4}$ | 1.2 |
| Wash 1 | BSA | 1.1 × $10^{10}$ | 6.0 × $10^6$ | 5.5 × $10^4$ | 1.6 |
| | hGHbp | 1.9 × $10^{10}$ | 1.7 × $10^7$ | 8.9 × $10^{-4}$ | 2.5 |
| Wash 2 | BSA | 5.9 × $10^7$ | 2.8 × $10^4$ | 4.7 × $10^{-4}$ | 1.3 |
| | hGHbp | 4.9 × $10^7$ | 2.7 × $10^6$ | 5.5 × $10^{-2}$ | 1.6 × $10^2$ |
| Eluate 1 (hGH) | BSA | 1.1 × $10^6$ | 1.9 × $10^3$ | 1.7 × $10^{-3}$ | 4.9 |
| | hGHbp | 1.2 × $10^6$ | 2.1 × $10^6$ | 1.8 | 5.1 × $10^3$ |

TABLE II-continued

Specific Binding of Hormone Phage to hGHbp-coated
Beads Provides an Enrichment for hGH-phage over M13KO7 Phage*

| Sample | Absorbent‡ | Total pfu | Toal cfu | Ratio (cfu/pfu) | Enrichment§ |
|---|---|---|---|---|---|
| Eluate 2 (hGH) | BSA | $5.9 \times 10^5$ | $1.2 \times 10^3$ | $2.0 \times 10^{-3}$ | 5.7 |
| | hGHbp | $5.5 \times 10^5$ | $1.3 \times 10^6$ | 2.4 | $6.9 \times 10^3$ |
| Eluate 3 (pH 2.1) | BSA | $4.6 \times 10^5$ | $2.0 \times 10^3$ | $4.3 \times 10^{-3}$ | 12.3 |
| | hGHbp | $3.8 \times 10^5$ | $4.0 \times 10^6$ | 10.5 | $3.0 \times 10^4$ |

*The titers of M13KO7 and hGH-phagemid particles in each fraction was determined by multiplying the number of plaque forming units (pfu) or carbenicillin resistant colony forming units (cfu) by the dilution factor, respectively. See Example IV for details.
†The ratio of M13KO7 to hGH-phagemid particels was adjusted to 3000:1 in the original mixture.
‡Absorbents were conjugated with BSA or hGHbp.
§Enrichments are calculated by dividing the cfu/pfu ratio after each step by cfu/pfu ratio in the original mixture.

In a typical enrichment experiment (Table II), one part of hGH phagemid was mixed with >3,000 parts M13KO7 phage. After one cycle of binding and elution, $10^6$ phage were recovered and the ratio of phagemid to M13KO7 phage was 2 to 1. Thus, a single binding selection step gave >500-fold enrichment. Additional elutions with free hGH or acid treatment to remove remaining phagemids produced even greater enrichments. The enrichments are comparable to those obtained by Smith and coworkers using batch elution from coated polystyrene plates (Smith, G. P. supra and Parmely, Smith supra) however much smaller volumes are used on the beads (200 µl vs. 6 ml). There was almost no enrichment for the hGH phagemid over M13KO7 when we used beads linked only to BSA. The slight enrichment observed for control beads (~10-fold for pH 2.1 elution; Table 2) may result from trace contaminants of bovine growth hormone binding protein present in the BSA linked to the bead. Nevertheless these data show the enrichments for the hGH phase depend upon the presence of the hGHbp on the bead suggesting binding occurs by specific interaction between hGH and the hGHbp.

We evaluated the enrichment for wild-type hGH over a weaker binding variant of the hGH on fusion phagemids to further demonstrate enrichment specificity, and to link the reduction in binding affinity for the purified hormones to enrichment factors after panning fusion phagemids. A fusion phagemid was constructed with an hGH mutant in which Arg64 was substituted with Ala (R64A). The R64A variant hormone is about 20-fold reduced in receptor binding affinity compared to hGH (Kd values of 7.1 nM and 0.34 nM, respectively [Cunningham, Wells, supra]). The titers of the R64A hGH-gene III fusion phagemid were comparable to those of wild-type hGH phagemid. After one round of binding and elution (Table III) the wild-type hGH phagemid was enriched from a mixture of the two phagemids plus M13KO7 by 8-fold relative to the phagemid R64A, and ~$10^4$ relative to M13KO7 helper phage.

TABLE III hGHbp-coated Beads Select for hGH Phagemids
Over a Weaker Binding hGH Variant Phagemid

| | Control beads | | hGHbp beads | |
|---|---|---|---|---|
| Sample | WT phagemid total phagemid | enrichment for WT/R64A | WT phagemid total phagemid | enrichment for WT/R64A |
| Original mixture | 8/20 | (1) | 8/20 | (1) |
| Supernatant | ND | — | 4/10 | 1.0 |
| Elution 1 (hGH) | 7/20 | 0.8 | 17/20 | 8.5‡ |
| Elution 2 (pH 2.1) | 11/20 | 1.8 | 21/27 | 5.2 |

*The parent M13KO7 phage, wild-type hGH phagemid and R64A phagemid particles were mixed at a ratio of $10^4$:0.4:0.6. Binding selections were carried out using beads linked with BSA (control beads) or with the hGHbp (hGHbp beads) as described in Table II and the Materials and Methods After each step, plasmid DNA was isolated (Birnboim, H. C., Doly, J., Nucleic Acids Res., 7:1513–1523, [1979]) from carbenicillin resistant colonies and analyzed by restriction analysis to determine if it contained the wild-type hGH or the R64A hGH gene III fusion.
†The enrichment for wild-type hGH phagemid over R64A mutant was calculated from the ratio of hGH phagemid present after each step to that present in the original mixture (8/20), divided by the corresponding ratio for R64A phagemids. WT = wild-type; ND = not determined.
‡The enrichment for phagemid over total M13KO7 parental phage was ~$10^4$ after this step.

Conclusions

By displaying a mixture of wild-type gene III and the gene III fusion protein on phagemid particles one can assemble and propagate virions that display a large and proper folded protein as a fusion to gene III. The copy number of the gene III fusion protein can be effectively controlled to avoid "chelate effects" yet maintained at high enough levels in the phagemid pool to permit panning of large epitope libraries (>$10^{10}$). We have shown that hGH (a 22 kD protein) can be displayed in its native folded form. Binding selections performed on receptor affinity beads eluted with free hGH, efficiently enriched for wild-type hGH phagemids over a mutant hGH phagemid shown to have reduced receptor binding affinity. Thus, it is possible to sort phagemid particles whose binding constants are down in the nanomolar range.

Protein-protein and antibody-antigen interactions are dominated by discontinuous epitopes (Janin, J., et al., *J. Mol. Biol.*, 204:155–164, [1988]; Argos, P., *Prot. Eng.*, 2:101–113, [1988]; Barlow, D. J., et al., *Nature*, 322:747–748, [1987]; and Davies, D. R., et al., *J. Biol. Chem.*, 263:10541–10544, [1988]); that is the residues directly involved in binding are close in tertiary structure but separated by residues not involved in binding. The screening system presented here should allow one to analyze more conveniently protein-receptor interactions and isolate discontinuous epitopes in proteins with new and high affinity binding properties.

Example VII
Selection of hGH Mutants from a Library Randomized at hGH Codons 172, 174, 176, 178.

Construction of template

A mutant of the hGH-gene III fusion protein was constructed using the method of Kunkel., et al. *Meth. Enzymol*, 154, 367–382 [1987]. Template DNA was prepared by growing the plasmid pS0132 (containing the natural hGH gene fused to the carboxy-terminal half of M13 gene III, under control of the alkaline phosphatase promoter) in CJ236 cells with M13-KO7 phage added as helper. Single-stranded, uracil-containing DNA was prepared for mutagenesis to introduce (1) a mutation in hGH which would greatly reduce beinding to the hGH binding protein (hGHbp); and (2) a unique restriction site (KpnI) which could be used for assaying for—and selecting against—parental background phage. Oligonucleotide-directed mutagenesis was carried out using T7 DNA polymerase and the following oligodeoxy-nucleotide:

```
                              Gly Thr          (SEQ ID NO: 7)
hGH codon:                    178 179
           5'-G ACA TTC CTG GGT ACC GTG CAG T-3'
                            <KpnI>
```

This oligo introduces the KpnI site as shown, along with mutations (R178G, I179T) in hGH. These mutations are predicted to reduce binding of hGH to hGHbp by more than 30-fold. Clones from the mutagenesis were screened by KpnI digestion and confirmed by dideoxy DNA sequencing. The resulting construct, to be used as a template for random mutagenesis, was designated pH0415.

Random mutagenesis within helix-4 of hGH

Codons 172, 174, 176, 178 were targeted for random mutagenesis in hGH, again using the method of Kunkel. Single-stranded template from pH0415 was prepared as above and mutagenesis was carried out using the following pool of oligos (SEQ ID NO:8)

```
hGH codon:                             172         174
       5'- GC TTC AGG AAG GAC ATG GAC NNS GTC NNS ACA- Ile
       176  178 179
      -NNS CTG NNS ATC GTG CAG TGC CGC TCT GTG G-3'
```

As shown, this oligo pool reverts codon 179 to wild-type (Ile), destroys the unique KpnI site of pH0415, and introduces random codons (NNS, where N=A,G,C, or T and S=G or C) at positions 172, 174, 176, and 178. Using this codon selection in the context of the above sequence, no additional KpnI sites can be created. The choice of the NNS degenerate sequence yields 32 possible codons (including the "step"

codon, and at least one codon for each amino acid) at 4 sites, for a total of $(32)^4 = 1,048,576$ possible nucleotide sequences (12% of which contain at least one stop codon), or $(20)^4 = 160,000$ possible polypeptide sequences plus 34,481 prematurely terminated sequences (i.e. sequences containing at least one stop codon).

Propagation of the Initial Library

The mutagenesis products were extracted twice with phenolchloroform (50:50) and ethanol precipitated with an excess of carrier tRNA to avoid adding salt that would confound the subsequent electroporation step. Approximately 50 ng (15 fmols) of DNA was electroporated into WJM101 cells ($2.8 \times 10^{10}$ cells/mL) in 45 μL total value in a 0.2 cm cuvette at a voltage setting of 2.49 kV with a single pulse (time constant=4.7 msec.)

The cells were allowed to recover 1 hour at 37° C. with shaking, then mixed with 25 mL 2YT medium, 100 μg/mL carbenicillin, and M13-K07 (multiplicity of infection=100). Plating of serial dilutions from this culture onto carbenicillin-containing media indicated that $8.2 \times 10^6$ electrotransformants were obtained. After 10' at 23° C., the culture was incubated overnight (15 hours) at 37° C. with shaking.

After overnight incubation, the cells were pelleted, and double-stranded DNA (dsDNA), designated pLIB1, was prepared by the alkaline lysis method. The supernatant was spun again to remove any remaining cells, and the phage, designated phage pool φ1, were PEG-precipitated and resuspended in 1 mL STE buffer (10 mM Tris, pH 7.6, 1 mM EDTA, 50 mM NaCl). Phage titers were measured as colony-forming units (CFU) for the recombinant phagemid containing hGH-g3p gene III fusion (hGH-$g^3$) plasmid, and plaque-forming units (PFU) for the M13-K07 helper phage.

Binding Selection Using Immobilized hGHbp

1. BINDING: An aliquot of phage pool φ1 ($6 \times 10^9$ CFU, $6 \times 10^7$ PFU) was diluted 4.5-fold in buffer A (Phosphate-buffered saline, 0.5% BSA, 0.05% Tween-20, 0.01% thimerosal) and mixed with a 5 μL suspension of oxirane-polyacrylamide beads coupled to the hGHbp containing a Ser237 Cys mutation (350 fmols) in a 1.5 mL silated polypropylene tube. As a control, an equivalent aliquot of phage were mixed in a separate tube with beads that had been coated with BSA only. The phase were allowed to bind to the beads by incubating 3 hours at room temperature (23° C.) with slow rotation (approximately 7 RPM). Subsequent steps were carried out with a constant volume of 200 μl and at room temperature.

2. WASH: The beads were spun 15 sec., and the supernatant was removed (Sup. 1). To remove phage/phagemid not specifically bound, the beads were washed twice by resuspending in buffer A, then pelleting. A final wash consisted of rotating the beads in buffer A for 2 hours.

3. hGH ELUTION: Phage/phagemid binding weakly to the beads were removed by stepwise elution with hGH. In the first step, the beads were rotated with buffer A containing 2nM hGH. After 17 hours, the beads were pelleted and resuspended in buffer A containing 20 nM hGH and rotated for 3 hours, then pelleted. In the final hGH wash, the beads were suspended in buffer A containing 200 nM hGH and rotated for 3 hours then pelleted.

4. GLYCINE ELUTION: To remove the tightest-binding phagemid (i.e. those still bound after the hGH washes), beads were suspended in Glycine buffer (1M Glycine, pH 2.0 with HCl), rotated 2 hours and pelleted. The supernatant (fraction "G"; 200 μL) was neutralized by adding 30 μL of 1M Tris base.

Fraction G eluted from the hGHbp-beads ($1 \times 10^6$ CFU, $5 \times 10^4$ PFU) was not substantially enriched for phagemid over K07 helper phage. We believe this resulted from the fact that K07 phage packaged during propagation of the recombinant phagemid display the hGH-g3p fusion.

However, when compared with fraction G eluted from the BSA-coated control beads, the hGHbp-beads yielded 14 times as many CFU's. This reflects the enrichment of tight-binding hGH-displaying phagemid over nonspecifically-binding phagemid.

5. PROPAGATION: An aliquot ($4.3 \times 10^5$ CFU) of fraction G eluted from the hGHbp-beads was used to infect log-phase WJM101 cells. Transductions were carried out by mixing 100 μL fraction G with 1 mL WJM101 cells, incubating 20 min. at 37° C., then adding K07 (multiplicity of infection=1000). Cultures (25 ml 2YT plus carbenicillin) were grown as described above and the second pool of phage (Library 1G, for first glycine elution) were prepared as described above.

Phage from library 1G (FIG. 3) were selected for binding to hGHbp beads as described above. Fraction G eluted from hGHbp beads contained 30 times as many CFU's as fraction G eluted from BSA-beads in this selection. Again, an aliquot of fraction G was propagated in WJM101 cells to yield library $1G^2$ (indicating that this library had been twice selected by glycine elution). Double-stranded DNA (pLIB $1G^2$) was also prepared from this culture.

KpnI assay and restriction-selection of dsDNA

Figure 3:
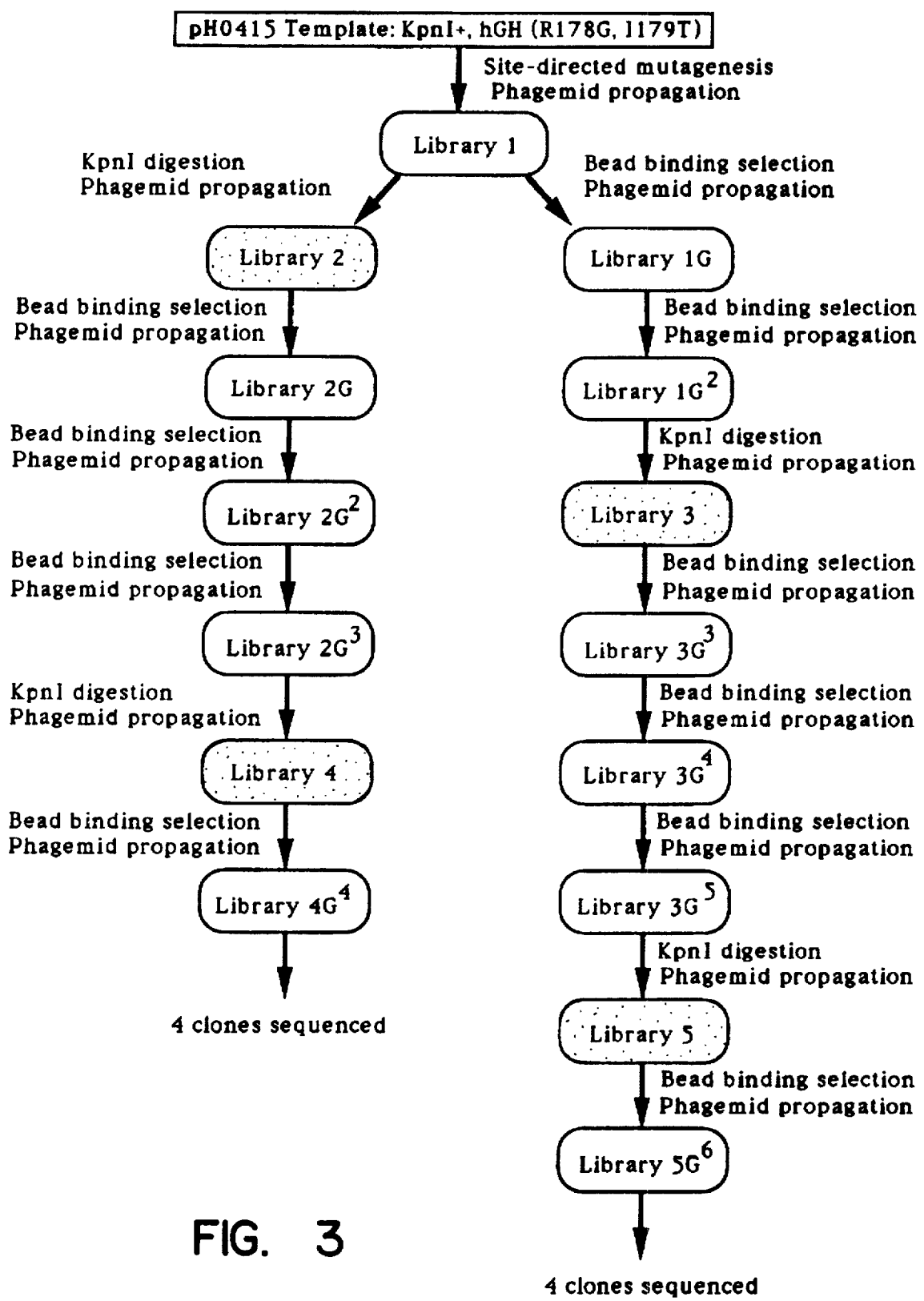
FIG. 3. Summary diagram of steps in the selection process for an hGH-phage library randomized at codons 172, 174, 176, and 178. The template molecules, pH0415, containing a unique KpnI restriction site and the hGH(R178G,I179T) gene was mutagenized as described in the text and electrotransformed into E. coli strain WJM101 to obtain the initial phagemid library, Library 1. An aliquot (approximately 2%) from Library 1 was used directly in an initial selection round as described in the text to yield Library 1G. Meanwhile, double-stranded DNA (dsDNA) was prepared from Library 1, digested with restriction enzyme KpnI to eliminate template background, and electrotransformed into WJW101 to yield Library 2. Subsequent rounds of selection (or KpnI digestion, shaded boxes) followed by phagemid propagation were carried out as indicated by the arrows, according to the procedure described in the text. Four independent clones from Library $4G^4$ and four independent clones from Library $5G^6$ were sequenced by dideoxy sequencing. All of these clones had the identical DNA sequence, corresponding to the hGH mutant (Glu 174 Ser, Phe 176 Tyr).
Figure 4:
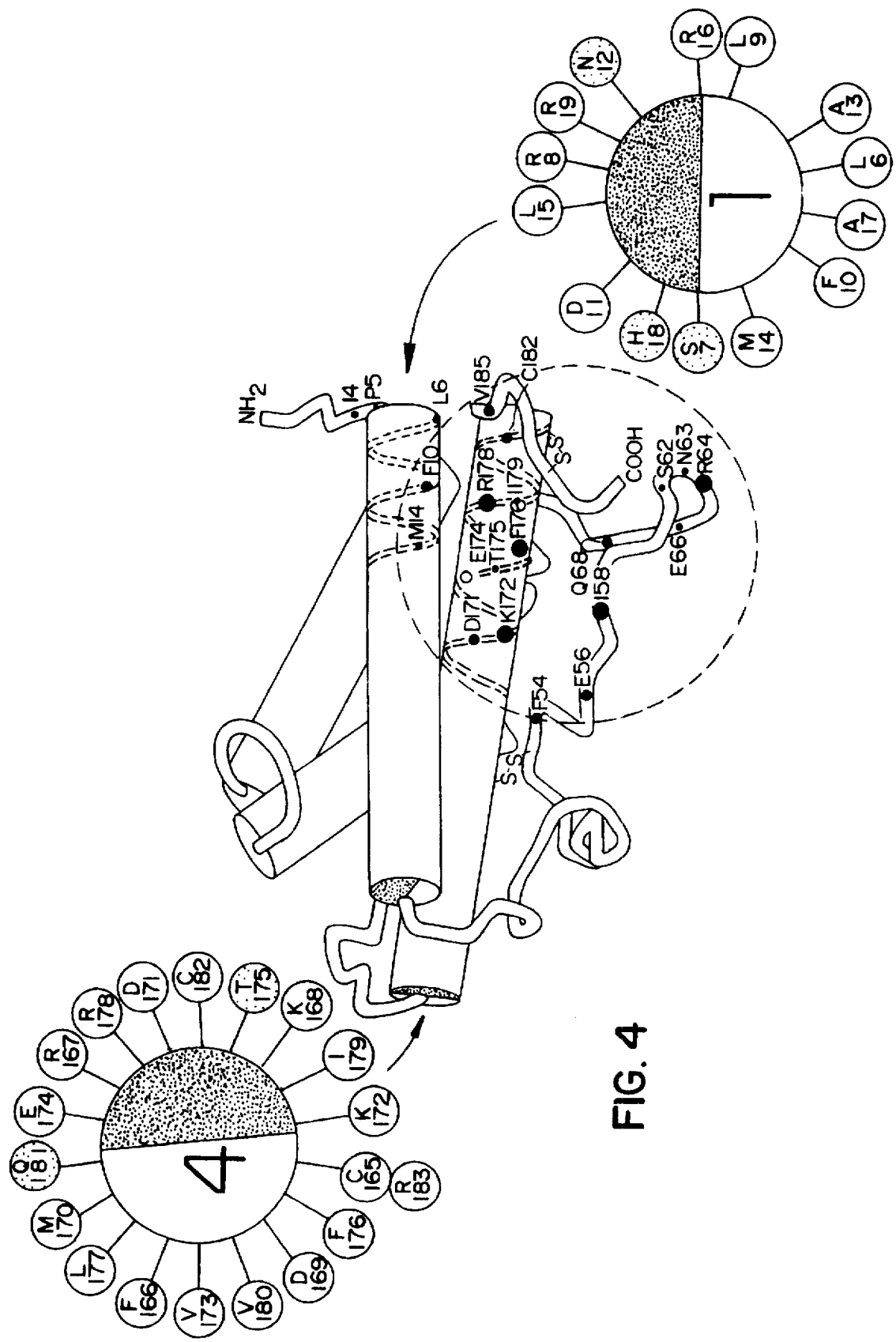
FIG. 4. Structural model of hGH derived from a 2.8 Å folding diagram of porcine growth hormone determined crystallographically. Location of residues in hGH that strongly modulate its binding to the hGH-binding protein are within the shaded circle. Alanine substitutions that cause a greater than tenfold reduction (●), a four- to tenfold reduction (●), or increase (○), or a two- to fourfold reduction (●), in binding affinity are indicated. Helical wheel projections in the regions of α-helix reveal their amphipathic quality. Blackened, shaded, or nonshaded residues are charged, polar, or nonpolar, respectively. In helix-4 the most important residues for mutation are on the hydrophilic face.
Figure 5:
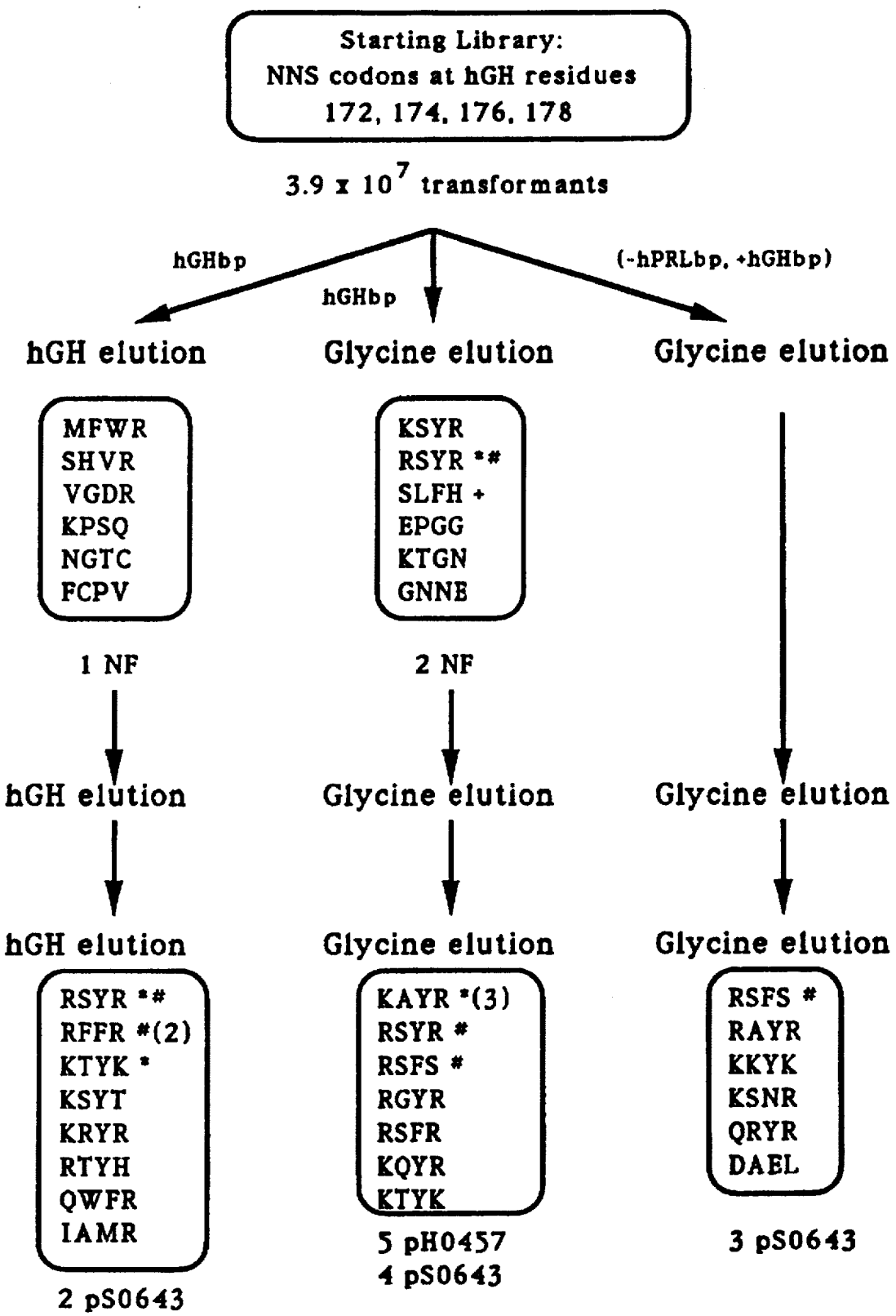
FIG. 5. Amino acid substitutions at positions 172, 174, 176 and 178 of hGH (The notation, e.g. KSYR, denotes hGH mutant 172K/174S/176Y/178R.) found after sequencing a number of clones from rounds 1 and 3 of the selection process for the pathways indicated (hGH elution; Glycine elution; or Glycine elution after pre-adsorption). Non-functional sequences (i.e. vector background, or other prematurely terminated and/or frame-shifted mutants) are shown as "NF". Functional sequences which contained a non-silent, spurious mutation (i.e. outside the set of target residues) are marked with a "+". Protein sequences which appeared more than once among all the sequenced clones, but with different DNA sequences, are marked with a "#". Protein sequences which appeared more than once among the sequenced clones and with the same DNA sequence are marked with a "***". Note that after three rounds of selection, 2 different contaminating sequences were found; these clones did not correspond to cassette mutants, but to previously constructed hormone phage. The pS0643 contaminant corresponds to wild-type hGH-phage (hGH "KEFR"). The pH0457 contaminant, which dominates the third-round glycine-selected pool of phage, corresponds to a previously identified mutant of hGH, "KSYR." The amplification of these cotaminants emphasizes the ability of the hormone-phase selection process to select for rarely occurring mutants. The convergence of sequences is also striking in all three pathways; R or K occurs most often at positions 172 and 178; Y or F occurs most often at position 176; and S, T, A, and other residues occur position 174.
Figure 6:
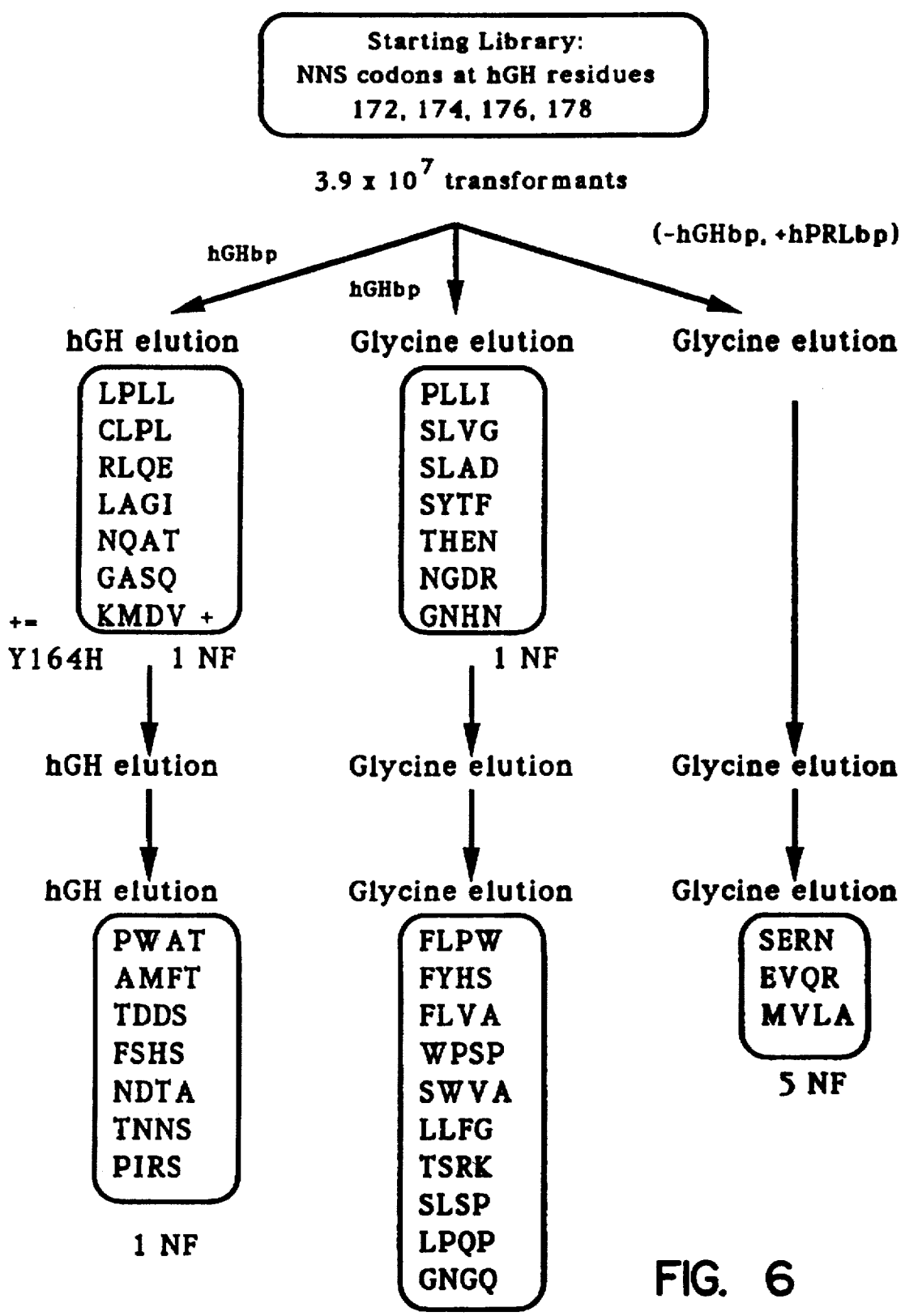
FIG. 6. Sequences from phage selected on hPRLbp-beads in the presence of zinc. The notation is as described in FIG. 5. Here, the convergence of sequences is not predictable, but there appears to be a bias towards hydrophobic sequences under the most stringent (Glycine) selection conditions; L, W and P residues are frequently found in this pool.
Figure 7:
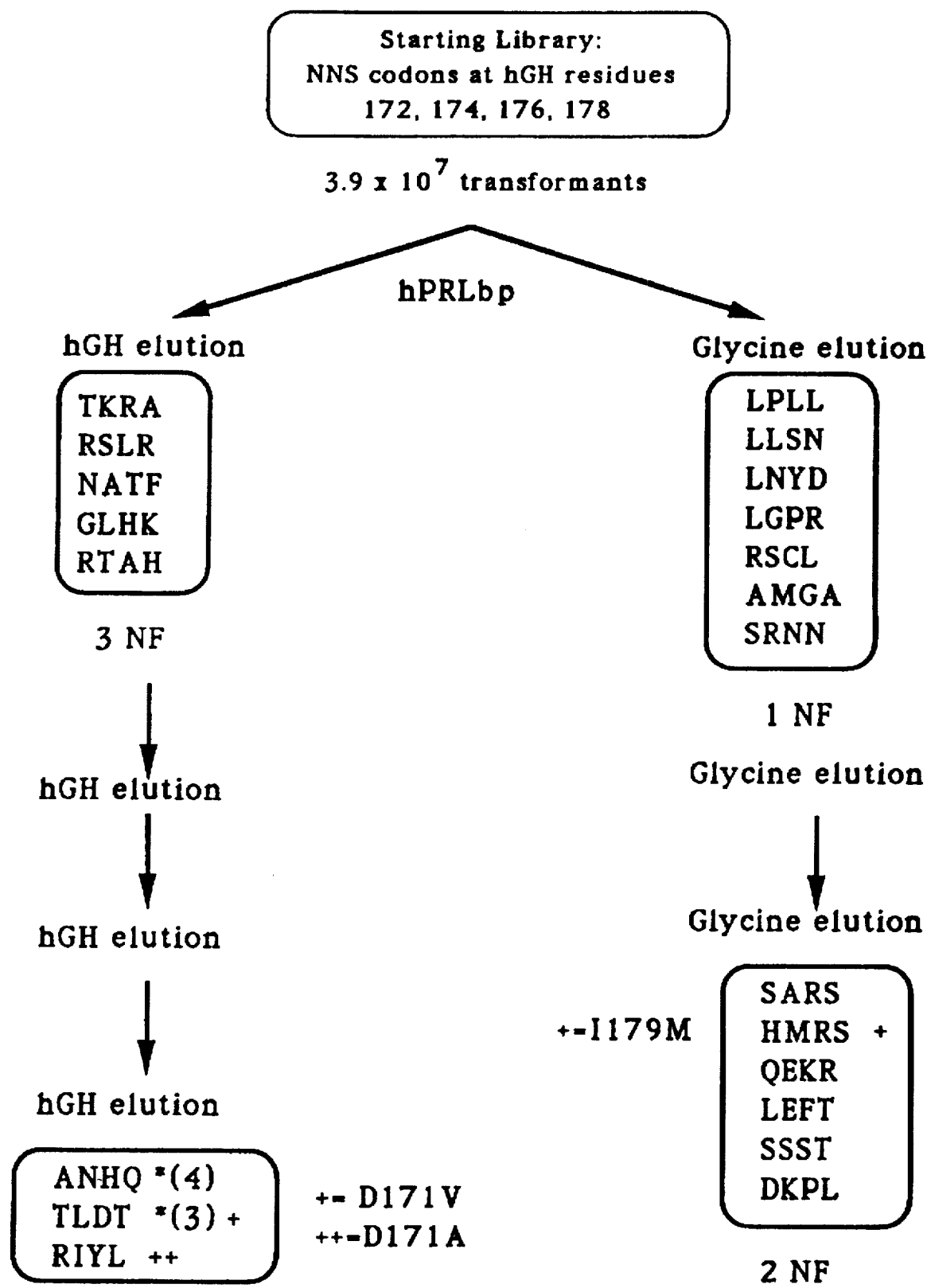
FIG. 7. Sequences from phase selected on hPRLbp-beads in the absence of zinc. The notation is as described in FIG. 5. In contrast to the sequences of FIG. 6, these sequences appear more hydrophilic. After 4 rounds of selection using hGH elution, two clones (ANHQ, and TLDT/171V) dominate the pool.

To reduce the level of background (KpnI$^+$) template, an aliquot (about 0.5 μg) of pLIB $1G^2$ was digested with KpnI and electroporated with WJM101 cells. These cells were grown in the presence of K07 (multiplicity of infection=100) as described for the initial library, and a new phage pool, pLIB 3, was prepared (FIG. 3).

In addition, an aliquot (about 0.5 μg) of dsDNA from the initial library (pLIB1) was digested with KpnI and electroporated directly into WJM101 cells. Transformants were allowed to recover as above, infected with M13-K07, and grown overnight to obtain a new library of phage, designated phage Library 2 (FIG. 3).

Successive rounds of selection

Phagemid binding, elution, and propagation were carried out in successive rounds for phagemid derived from both pLIB 2 and pLIB 3 (FIG. 3) as described above, except that (1) an excess (10-fold over CFU) of purified K07 phage (not displaying hGH) was added in the bead-binding cocktail, and (2) the hGH stepwise elutions were replaced with brief washings of buffer A alone. Also, in some cases, XL1-Blue cells were used for phagemid propagation.

An additional digestion of dsDNA with KpnI was carried out on pLIB $2G^3$ and on pLIB $3G^5$ before the final round of bead-binding selection (FIG. 3).

DNA Sequencing of Selected Phagemids

Four independently isolated clones from LIB $4G^4$ and four independently isolated clones from LIB $5G^6$ were sequenced by dideoxy sequencing. All eight of these clones had identical DNA sequences:

hGH codon:   172   174   176   178
5'-AAG GTC TCC ACA TAC CTG AGG ATC-3'

Thus, all these encode the same mutant of hGH:(E174S, F176Y). Residue 172 in these clones is Lys as in wild-type. The codon selected for 172 is also identical to wild-type hGH. This is not suprising since AAG is the only lysine-codon possible from a degenerate "NNS" codon set. Residue 178-Arg is also the same as wild-type, but here, the codon selected from the library AAG instead of CGC as is found in wild-type hGH, even though the latter codon is also possible using the "NNS" codon set.

Multiplicity of K07 Infection

The multiplicity of infection of K07 infection is an important parameter in the propagation of recombinant phagemids. The K07 multiplicity of infection must be high enough to insure that virtually all cells transformed or transfected with phagemid are able to package new phagemid particles. Furthermore, the concentration of wild-type gene III in each cell should be kept high to reduce the possibility of multiple hGH-gene III fusion molecules being displayed on each phgemid particle, thereby reducing chelate effects in binding. However, if the K07 multiplicity of infection is too high, the packaging of K07 will compete with that of recombinant phagemid. We find that acceptable phagemid yields, with only 1–10% background K07 phage, are obtained when the K07 multiplicity of infection is 100.

TABLE IV

| Phage Pool | moi (K07) | Enrichment CFU/PFU | hGHbp/ BSA beads | Fraction KpnI |
|---|---|---|---|---|
| LIB 1 | 1000 | ND | 14 | 0.44 |
| LIB 1G | 1000 | ND | 30 | 0.57 |
| LIB 3 | 100 | ND | 1.7 | 0.26 |
| LIB $3G^3$ | 10 | ND | 8.5 | 0.18 |
| LIB $3G^4$ | 100 | 460 | 220 | 0.13 |
| LIB 5 | 100 | ND | 15 | ND |
| LIB 2 | 100 | ND | 1.7 | <0.05 |
| LIB 2G | 10 | ND | 4.1 | <0.10 |
| LIB $2G^2$ | 100 | 1000 | 27 | 0.18 |
| LIB 4 | 100 | 170 | 38 | ND |

Phage pools are labelled as shown (FIG. 3). The multiplicity of infection (moi) refers to the multiplicity of K07 infection (PFU/cells) in the propagation of phagemid. The enrichment of CFU over PFU is shown in those cases where purified K07 was added in the binding step. The ratio of CFU eluting from hGHbp-beads over CFU eluting from BSA-beads is shown. The fraction of KpnI-containing template (i.e., pH0415) remaining in the pool was determined by digesting dsDNA with KpnI plus EcoRI, running the products on a 1% agarose gel, and laser-scanning a negative of the ethidium bromide-stained DNA.

Receptor-binding affinity of the hormone hGH(E174S, F176Y)

The fact that a single clone was isolated from two different pathways of selection (FIG. 3) suggested that the double mutant (E174S,F176Y) binds strongly to hGHbp. To determine the affinity of this mutant of hGH for hGHbp, we constructed this mutant of hGH by site-directed mutagenesis, using a plasmid (pB0720) which contains the wild-type hGH gene as template and the following oligonucleotide (SEQ ID NO:10) which changes codons 174 and 176:

hGH codon:   172   174   176   178
             Lys   Ser   Tyr   Arg
5'- ATG GAC AAG GTG TCG ACA TAC CTG CGC ATC GTG -3'

The resulting construct, pH0458B, was transformed into *E. coli* strain 16C9 for expression of the mutant hormone. Scatchard analysis of competitive binding of hGH(E174S, F176Y) versus $^{125}$I-hGH to hGHbp indicated that the (E174S,F176Y) mutant has a binding affinity at least 5.0-fold tighter than that of wild-type hGH.

EXAMPLE VIII

SELECTION OF hGH VARIANTS FROM A HELIX-4 RANDOM CASSETTE LIBRARY OF HORMONE-PHAGE

Figure 9:
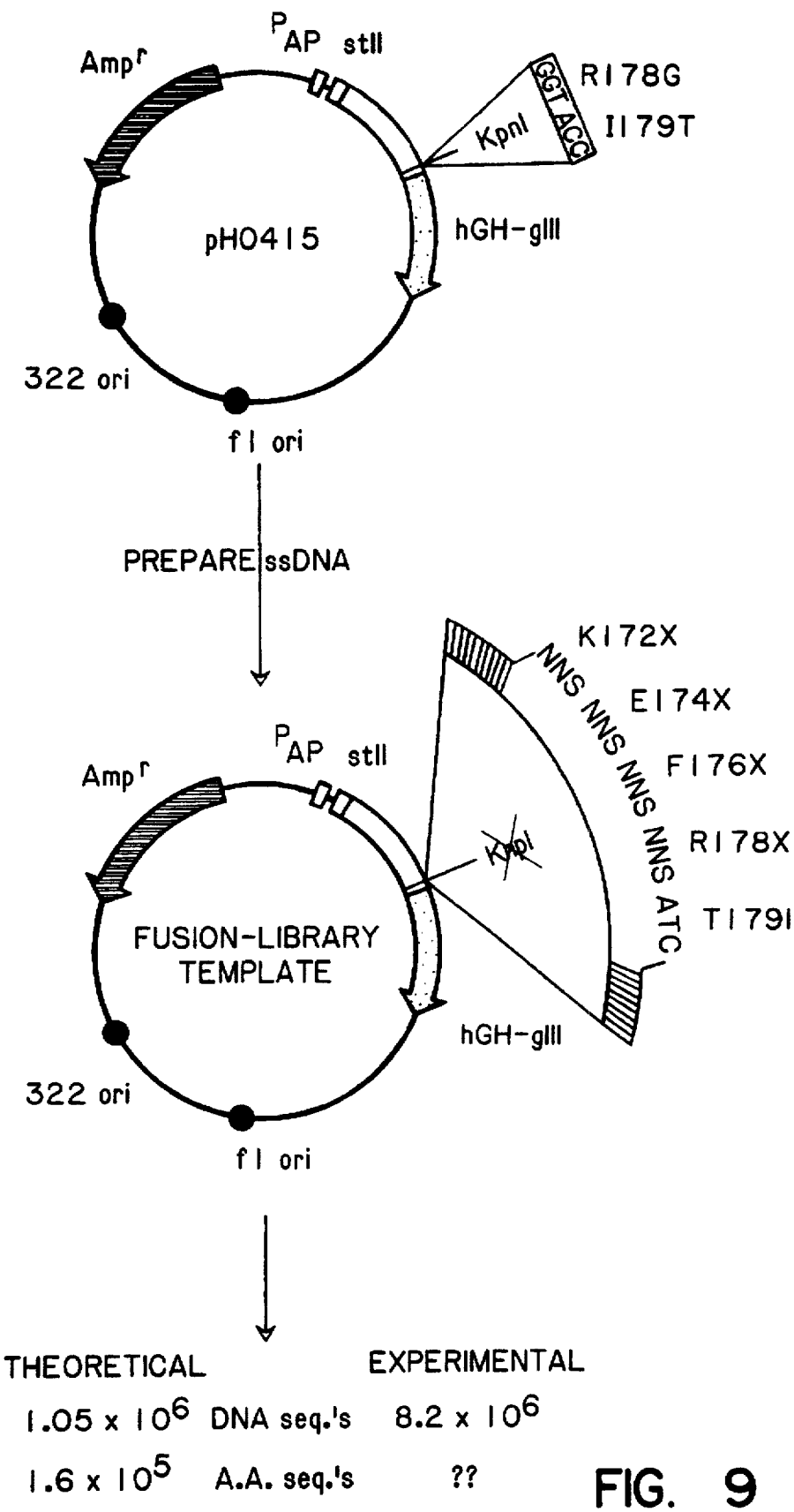
FIG. 9. Construction of phagemid fl ori from pHO415. This vector for cassette mutagenesis and expression of the hGH-gene III fusion protein was constructed as follows. Plasmid pS0643 was constructed by oligonucleotide-directed mutagenesis of pS0132, which contains pBR322 and fl origins of replication and expresses an hGH-gene III fusion protein (hGH residues 1-191, followed by a single Gly residue, fused to Pro-198 of gene III) under the control of the E. coli pho A promoter. Mutagenesis was carried out with the oligonucleotide 5'-GGC-AGC-TGT-GGC-T TC-TAG-AGT-GGC-GGC-GGC-TCT-GGT-3'(SEQ ID NO:1), which introduced a XbaI site (underlined) and an amber stop codon (TAG) following Phe-191 of hGH.
Figure 12:
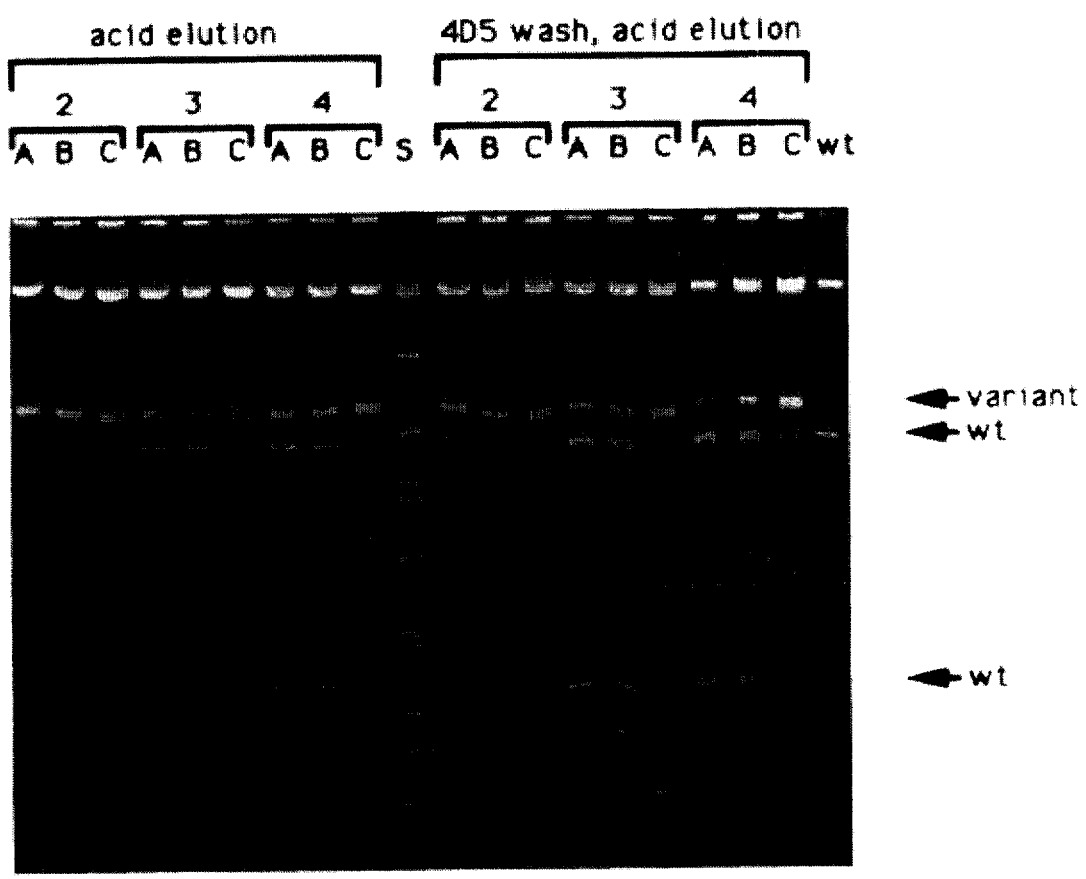
FIG. 12. Enrichment of wild-type 4D5 $F_{ab}$ phagemid from variant $F_{ab}$ phagemid. Mixtures of wild-type phagemid and variant 4D5 $F_{ab}$ phagemid in a ratio of 1:1,000 were selected on plates coated with the extra-cellular domain protein of the HER-2receptor. After each round of selection, a portion of the eluted phagemid were infected into E. coli and plasmid DNA was prepared. This plasmid DNA was then digested with Eco RV and PstI, separated on a 5% polyacrylamide gel, and stained with ethidium bromide. The bands were visualized under UV light. The bands due to the wild-type and variant plasmids and marked with arrows. The first round of selection was eluted only under acid conditions; subsequent rounds were eluted with either an acid elution (left side of Figure) or with a humanized 4D5 antibody wash step prior to acid elution (right side of Figure) using methods described in Example VIII. Three variant 4D5 $F_{ab}$ molecules were made: H91A (amino acid histidine at position 91 on the $V_L$ chain mutated to alanine; indicated as 'A' lanes in Figure) Y49A (amino acid tyrosine at position 49 on the $V_L$ chain mutated to alanine; indicated as 'B' lanes in the Figure), and Y92A (amino acid tyrosine at position 92 on the $V_L$ chain mutated to alanine; indicated as 'C' lanes in the Figure). Amino acid position numbering is according to Kabat et al., (*Sequences of proteins of immunological interest*, 4th ed., U.S. Dept of Health and Human Services, Public Health Service, Nat'l. Institute of Health, Bethesda, Md. [1987]).

Human growth hormone variants were produced by the method of the present invention using the phagemid described in FIG. 9.

Construction of a de-fusable hormone-phage vector

We designed a vector for cassette mutagenesis (Wells et al., *Gene* 34, 315–323 [1985]) and expression of the hGH-gene III fusion protein with the objectives of (1) improving the linkage between hGH and the gene III moiety to more favorably display the hGH moiety on the phage (2) limiting expression of the fusion protein to obtain essentially "monovalent display," (3) allowing for restriction nuclease selection against the starting vector, (4) eliminating expression of fusion protein from the starting vector, and (5) achieving facile expression of the corresponding free hormone from a given hGH-gene III fusion mutant.

Plasmid pS0643 was constructed by oligonucleotide-directed mutagenesis (Kunkel et al., *Methods Enzymol.* 154, 367–382 [1987]) of pS0132, which contains pBR322 and f1 origins of replication and expresses an hGH-gene III fusion protein (hGH residues 1–191, followed by a single Gly residue, fused to Pro-198 of gene III) under the control of the *E. coli* pHoA promoter (Bass et al., *Proteins* 8, 309–314 [1990]) (FIG. 9). Mutagenesis was carried out with the oligonucleotide 5'-GGC-AGC-TGT-GGC-T TC-TAG-AGT-GGC-GGC-GGC-TCT-GGT-3' (SEQ ID NO:11) which introduces a XhaI site (underlined) and an amber stop codon (TAG) following Phe-191 of hGH. In the resulting construct, pS0643, a portion of gene III was deleted, and two silent mutations (underlined) occurred, yielding the following junction between hGH and gene III:

| ——— hGH ———> | | | | | | gene III ———> | | | | | | |
|---|---|---|---|---|---|---|---|---|---|---|---|---|
| 187 | 188 | 189 | 190 | 191 | am* | 249 | 250 | 251 | 252 | 253 | 254 | |
| Gly | Ser | Cys | Gly | Phe | Glu | Ser | Gly | Gly | Gly | Ser | Gly | (SEQ ID NO:13) |
| GGC | AGC | TGT | GGA | TTC | TAG | AGT | GGC | GGT | GGC | TCT | GGT | (SEQ ID NO:12) |

This shortens the total size of the fusion protein from 401 residues in pS0132 to 350 residues in pS0643. Experiments using monoclonal antibodies against hGH have demonstrated that the hGH portion of the new fusion protein, assembled on a phage particle, is more accessible than was the previous, longer fusion.

For propagation of hormone-displaying phage, pS0643 and derivatives can be grown in a amber-suppressor strain of *E. coli*, such as JM101 or LX1-Blue (Bullock et al., *Bio-Techniques* 5, 376–379 [1987]). Shown above is substitution of Glu at the amber codon which occurs in supE suppressor strains. Suppression with other amino acids is also possible in various available strains of *E. coli* well known and publically available.

To express hGH (or mutants) free of the gene III portion of the fusion, pS0643 and derivatives can simply be grown in a non-suppressor strain such as 16C9. In this case, the amber codon (TAG) leads to termination of translation, which yields free hormone, without the need for an independent DNA construction.

To create sites for cassette mutagenesis, pS0643 was mutated with the oligonucleotides (1) 5'-CGG-ACT-GGG-C AG-ATA-TTC-AAG-CAG-ACC-3' (SEQ ID NO:14) which destroys the unique BglII site of pS0643; (2) 5'-CTC-AAG-A A C - T A C - G GG-TTA-CCC-TGA-CTG-CTT-CAG-GAA-GG-3' (SEQ ID NO:15) which inserts a unique BstEII site, a single-base frameshift, and a non-amber stop codon (TGA); and (3) 5'-CGC-ATC-GTG-CAG-TGC-AGA-TCT-GTG-GAG-GGC-3' (SEQ ID NO:16) which introduces a new BglII site, to yield the starting vector, pH0509. The addition of a frameshift along with a TGA stop codon insures that no gene III-fusion can be produced from the starting vector. The BstEII-BglIII segment is cut out of pH0509 and replaced with a DNA cassette, mutated at the codons of interest. Other restriction sites for cassette mutagenesis at other locations in hGH have also been introduced into the hormone-phage vector.

Cassette mutagenesis within helix 4 of hGH

Codons 172, 174, 176 and 178 of hGH were targeted for random mutagenesis because they all lie on or near the surface of hGH and contribute significantly to receptor-binding (Cunningham and Wells, *Science* 244, 1081–1085 [1989]); they all lie within a well-defined structure, occupying 2 "turns" on the same side of helix 4; and they are each substituted by at least one amino acid among known evolutionary variants of hGH.

We chose to substitute NNS (N=A/G/C/T; S=G/C) at each of the target residues. The choice of the NNS degenerate sequence yields 32 possible codons (including at least one codon for each amino acid) at 4 sites, for a total of $(32)^4 = 1,048,576$ possible nucleotide sequences, or $(20)^4 = 160,000$ possible polypeptide sequences. Only one stop codon, amber (TAG), is allowed by this choice of codons, and this codon is suppressible as Glu in supE strains of *E. coli*.

Two degenerate oligonucleotides, with NNS at codons 172, 174, 176, and 178, were synthesized, phosphorylated, and annealed to construct the mutagenic cassette: 5'-GT-TAC-TCT-ACT-GCT-TTC-AGG-AAG-GAC-ATG-GAC-NNS-GTC-NNS-ACA-NNS-CTG-NNS-ATC-GTG-CAG-TGC-A-3' (SEQ ID NO:17) and 5'-GA-TCT-GCA-CTG-CAC-GAT-SNN-CAG-SNN-TGT-SNN-GAC-SNN-GTC-CAT-GTC-CCT-CCT-GAA-GCA-GTA-GA-3' (SEQ ID NO:18).

The vector was prepared by digesting pH0509 with BstEII followed by BglIII. The products were run on a 1% agarose gel and the large fragment excised, phenol-extracted, and ethanol precipitated. This fragment was treated with calf intestinal phosphatase (Boehringer), then phenol:chloroform extracted, ethanol precipitated, and resuspended for ligation with the mutagenic cassette.

Propagation of the Initial library in XL1-Blue cells

Following ligation, the reaction products were again digested with BstEII, then phenol:chloroform extracted, ethanol precipitated and resuspended in water. (A BstEII recognition site (GGTNACC) is created within cassettes which contain a G at position 3 of codon 172 and an ACC (Thr) codon at 174. However, treatment with BstEII at this step should not select against any of the possible mutagenic cassettes, because virtually all cassettes will be heteroduplexes, which cannot be cleaved by the enzyme.) Approximately 150 ng (45 fmols) of DNA was electroporated into XL1-Blue cells ($1.8 \times 10^9$ cells in 0.045 mL) in a 0.2 cm cuvette at a voltage setting of 2.49 kV with a single pulse (time constant=4.7 msec.).

The cells were allowed to recover 1 hour at 37° C. in S.O.C media with shaking, then mixed with 25 mL 2YT medium, 100 mg/mL carbenicillin, and M13-K07 (moi= 100). After 10' at 23° C., the culture was incubated overnight (15 hours) at 37° C. with shaking. Plating of serial dilutions from this culture onto carbenicillin-containing media indicated that $3.9 \times 10^7$ electrotransformants were obtained.

After overnight incubation, the cells were pelleted, and double-stranded DNA (dsDNA), designated pH0529E (the initial library), was prepared by the alkaline lysis method. The supernatant was spun again to remove any remaining cells, and the phage, designated phage pool φH0529E (the initial library of phage), were PEG-precipitated and resuspended in 1 mL STE buffer (10 mM Tris, pH 7.6, 1 mM EDTA, 50 mM NaCl). Phage titers were measured as colony-forming units (CFU) for the recombinant phagemid containing hGH-G3p. Approximately $4.5 \times 10^{13}$ CFU were obtained from the starting library.

Degeneracy of the starting library

From the pool of electrotransformants, 58 clones were sequenced in the region of the BstEII-BglIII cassette. Of these, 17% corresponded to the starting vector, 17% contained at least one frame shift, and 7% contained a non-silent (non-terminating) mutation outside the four target codons. We conclude that 41% of the clones were defective by one of the above measures, leaving a total functional pool of $2.0 \times 10^7$ initial transformants. This number still exceeds the possible number of DNA sequences by nearly 20-fold. Therefore, we are confident of having all possible sequences represented in the starting library.

We examined the sequences of non-selected phage to evaluate the degree of codon bias in the mutagenesis (Table V). The results indicated that, although some codons (and amino acids) are under- or over-represented relative to the random expectation, the library is extremely diverse, with no evidence of large-scale "sibling" degeneracy (Table VI).

TABLE V

Codon distribution (per 188 codons) of non-selected hormone phage. Clones were sequenced from the starting library (ph0529E). All codons were tabulated, including those from clones which contained spurious mutations and/or frameshifts. *Note: the amber stop codon (TAG) is suppressed as Glu in XL1-Blue cells. Highlighted codons were over/under-represented by 50% or more.

| Residue | Number expected | Number found | Found/Expected |
|---|---|---|---|
| Leu | 17.6 | 18 | 1.0 |
| Ser | 17.6 | 26 | 1.5 |
| Arg | 17.6 | 10 | 0.57 |
| Pro | 11.8 | 16 | 1.4 |
| Thr | 11.8 | 14 | 1.2 |
| Ala | 11.8 | 13 | 1.1 |
| Gly | 11.8 | 16 | 1.4 |
| Val | 11.8 | 4 | 0.3 |
| Ile | 5.9 | 2 | 0.3 |
| Met | 5.9 | 1 | 0.2 |
| Tyr | 5.9 | 1 | 0.2 |
| His | 5.9 | 2 | 0.3 |
| Trp | 5.9 | 2 | 0.3 |
| Phe | 5.9 | 5 | 0.9 |
| Cys | 5.9 | 5 | 0.9 |
| Gln | 5.9 | 7 | 1.2 |
| Asn | 5.9 | 14 | 2.4 |
| Lys | 5.9 | 11 | 1.9 |
| Asp | 5.9 | 9 | 1.5 |
| Glu | 5.9 | 6 | 1.0 |
| amber* | 5.9 | 6 | 1.0 |

TABLE VI

Non-selected (pH0529E) clones with an open reading frame. The notation, e.g. TWGS, denotes the hGH mutant 172T/174W/176G/178S. Amber (TAG) codons, translated as Glu in XL1-Blue cells are shown as ε.

| | | |
|---|---|---|
| KεNT | KTEQ | CVLQ |
| TWGS | NNCR | EASL |
| PεER | FPCL | SSKE |
| LPPS | NSDF | ALLL |
| SLDP | HRPS | PSHP |
| QQSN | LSLε | SYAP |
| GSKT | NGSK | ASNG |
| TPVT | LTTE | EANN |
| RSRA | PSGG | KNAK |
| LCGL | LWFP | SRGK |
| TGRL | PAGS | GLDG |
| AKAS | GRAK | NDPI |
| GNDD | GTNG | |

Preparation of Immobilized hGHbp and hPRLbp

Immobilized hGHbp ("hGHbp-beads") was prepared as described (Bass et al., *Proteins* 8, 309–314 [1990]), except that wild-type hGHbp (Fuh et al., *J. Biol. Chem.* 265, 3111–3115 [1990]) was used. Competitive binding experiments with [$^{125}$I] hGH indicated that 58 fmols of functional hGHbp were coupled per μL of bead suspension.

Immobilized hPRLbp ("hPRLbp-beads") was prepared as above, using the 211-residue extracellular domain of the prolactin receptor (Cunningham et al., *Science* 250, 1709–1712 [1990]). Competitive binding experiments with [$^{125}$I] hGH in the presence of 50 μM zinc indicated that 2.1 fmols of functional hPRLbp were coupled per μL of bead suspension.

"Blank beads" were prepared by treating the oxirane-acrylamide beads with 0.6M ethanolamine (pH 9.2) for 15 hours at 4° C.

Binding selection using immobilized hGHbp and hPRLbp

Binding of hormone-phage to beads was carried out in one of the following buffers: Buffer A (PBS, 0.5% BSA, 0.05% Tween 20, 0.01% thimerosal) for selections using hGHbp and blank beads; Buffer B (50 mM tris pH 7.5, 10 mM MgCl$_2$, 0.5% BSA, 0.05% Tween 20, 100 mM ZnCl$_2$) for selections using hPRLbp in the presence of zinc (+Zn$^{2+}$); or Buffer C (PBS, 0.5% BSA, 0.05% Tween, 20, 0.01% thimerosal, 10 mM EDTA) for selections using hPRLbp in the absence of zinc (+EDTA). Binding selections were carried out according to each of the following paths: (1) binding to blank beads, (2) binding to hGHbp-beads, (3) binding to hPRLbp-beads (+Zn$^{2+}$), (4) binding to hPRLbp-beads (+EDTA), (5) pre-adsorbing twice with hGHbp beads then binding the non-adsorbed fraction to hPRLbp-beads ("–hGHbp, +hPRLbp" selection), or (6) pre-adsorbing twice with hPRLbp-beads then binding the non-adsorbed fraction to hGHbp-beads ("–hPRLbp, +hGHbp" selection). The latter two procedures are expected to enrich for mutants binding hPRLbp but not hGHbp, or for mutants binding hGHbp but not hPRLbp, respectively. Binding and elution of phage was carried out in each cycle as follows:

1. BINDING: An aliquot of hormone phage (typically $10^9$–$10^{10}$ CFU) was mixed with an equal amount of non-hormone phage (pCAT), diluted into the appropriate buffer (A, B, or C), and mixed with a 10 mL suspension of hGHbp, hPRLbp or blank beads in a total volume of 200 mL in a 1.5 mL polypropylene tube. The phage were allowed to bind to the beads by incubating 1 hour at room temperature (23° C.) with slow rotation (approximately 7 RPM). Subsequent steps were carried out with a constant volume of 200 μL and at room temperature.

2. WASHES: The beads were spun 15 sec., and the supernatant was removed. To reduce the number of phage not specifically bound, the beads were washed 5times by resuspending briefly in the appropriate buffer, then pelleting.
3. hGH ELUTION: Phage binding weakly to the beads were removed by elution with hGH. The beads were rotated with the appropriate buffer containing 400 nM hGH for 15–17 hours. The supernatant was saved as the "hGH elution" and the beads. The beads were washed by resuspending briefly in buffer and pelleting.
4. GLYCINE ELUTION: To remove the tightest-binding phase (i.e. those still bound after the hGH wash), beads were suspended in Glycine buffer (Buffer A plus 0.2M Glycine, pH 2.0 with HCl), rotated 1 hour and pelleted. The supernatant ("Glycine elution"; 200 µL) was neutralized by adding 30 mL of 1M Tris base and stored at 4° C.
5. PROPAGATION: Aliquots from the hGH elutions and from the Glycine elutions from each set of beads under each set of conditions were used to infect separate cultures of log-phase XL1-Blue cells. Transductions were carried out by mixing phage with 1 mL XL1-Blue cells, incubating 20 min. at 37° C., then adding K07 (moi=100) Cultures (25 mL 2YT plus carbenicillin) were grown as described above and the next pool of phage was prepared as described above.

Phage binding, elution, and propagation were carried out in successive rounds, according to the cycle described above. For example, the phage amplified from the hGH elution from hGHbp-beads were again selected on hGHbp-beads and eluted with hGH, then used to infect a new culture of LX1-Blue cells. Three to five rounds of selection and propagation were carried out for each of the selection procedures described above.

DNA Sequencing of selected phagemids

From the hGH and Glycine elution steps of each cycle, an aliquot of phage was used to inoculate LX1-Blue cells, which were plated on LB media containing carbenicillin and tetracycline to obtain independent clones from each phage pool. Single-stranded DNA was prepared from isolated colony and sequenced in the region of the mutagenic cassette. The results of DNA sequencing are summarized in terms of the deduced amino acid sequences in FIGS. 5, 6, 7, and 8.

Expression and assay of hGH mutants

To determine the binding affinity of some of the selected hGH mutants for the hGHbp, we transformed DNA from sequenced clones into E. coli strain 16C9. As described above, this is a non-suppressor strain which terminates translation of protein after the final Phe-191 residue of hGH. Single-stranded DNA was used for these transformations, but double-stranded DNA or even whole phage can be easily electroporated into a non-suppressor strain for expression of free hormone.

Mutants of hGH were prepared from osmotically shocked cells by ammonium sulfate precipitation as described for hGH (Olson et al., *Nature* 293, 408–411 [1981]), and protein concentrations were measured by laser densitometry of Coomassie-stained SDS-polyacrylamide gel electrophoresis gels, using hGH as standard (Cunningham and Wells, *Science* 244, 1081–1085 [1989]).

The binding affinity of each mutant was determined by displacement of $^{125}$I hGH as described (Spencer et al., *J. Biol. Chem.* 263, 7862–7867 [1988]; Fuh et al., *J. Biol. Chem.* 265, 3111–3115 [1990]), using an anti-receptor monoclonal antibody (Mab263).

The results for a number of hGH mutants, selected by different pathways (FIG. 6) are shown in Table VII. Many of these mutants have a tighter binding affinity for hGHbp than wild-type hGH. The most improved mutant, KSYR, has a binding affinity 5.6 times greater than that of wild-type hGH. The weakest selected mutant, among those assayed was only about 10-fold lower in binding affinity than hGH.

Binding assays may be carried out for mutants selected for hPRLbp-binding.

TABLE VII

Competitive binding to hGHbp
The selected pool in which each mutant was found is indicated as 1G (first glycine selection), 3G (third glycine selection), 3H (third hGH selection), 3* (third selection, not binding to hPRLbp, but binding to hGHbp). The number of times each mutant occurred among all sequenced clones is shown ( ).

| Mutant | Kd (nM) | Kd(mut)/Kd(hGH) | Pool |
|---|---|---|---|
| KSYR (6) | 0.06 + 0.01 | 0.18 | 1G,3G |
| RSFR | 0.10 + 0.05 | 0.30 | 3G |
| RAYR | 0.13 + 0.04 | 0.37 | 3* |
| KTYK (2) | 0.16 + 0.04 | 0.47 | H,3G |
| RSYR (3) | 0.20 + 0.07 | 0.58 | 1G,3H,3G |
| KAYR (3) | 0.22 + 0.03 | 0.66 | 3G |
| RFFR (2) | 0.26 + 0.05 | 0.76 | 3H |
| KQYR | 0.33 + 0.03 | 1.0 | 3G |
| KEFR = wt (9) | 0.34 + 0.05 | 1.0 | 3H,3G,3* |
| RTYH | 0.68 + 0.17 | 2.0 | 3H |
| QRYR | 0.83 + 0.14 | 2.5 | 3* |
| KKYK | 1.1 + 0.4 | 3.2 | 3* |
| RSFS (2) | 1.1 + 0.2 | 3.3 | 3G,* |
| KSNR | 3.1 + 0.4 | 9.2 | 3* |

Additive and non-additive effects on binding

At some residues, substitution of a particular amino acid has essentially the same effect independent of surrounding residues. For example, substitution of F176Y in the background of 172R/174S reduces binding affinity by 2.0-fold (RSFR vs. RSYR). Similarly, in the background of 172K/174A the binding affinity of the F176Y mutant (KAYR) is 2.9-fold weaker than the corresponding 176F mutant (KAFR; Cunningham and Wells, 1989).

On the other hand, the binding constants determined for several selected mutants of hGH demonstrate non-additive effects of some amino acid substitutions at residues 172, 174, 176, and 178. For example, in the background of 172K/176Y, the substitution E174S results in a mutant (KSYR) which binds hGHbp 3.7-fold tighter than the corresponding mutant containing E174A (KAYR). However, in the background of 172R/176Y, the effects of these E174 substitutions are reversed. Here, the E174A mutant (RAYR) binds 1.5-fold tighter than the E174S mutant (RSYR).

Such non-additive effects on binding for substitutions at proximal residues illustrate the utility of protein-phage binding selection as a means of selecting optimized mutants from a library randomized at several positions. In the absence of detailed structural information, without such a selection process, many combinations of substitutions might be tried before finding the optimum mutant.

EXAMPLE IX

SELECTION OF hGH VARIANTS FROM A HELIX-1 RANDOM CASSETTE LIBRARY OF HORMONE-PHAGE

Using the methods described in Example VIII, we targeted another region of hGH involved in binding to the hGHbp and/or hPRLbp, helix 1 residues 10, 14, 18, 21, for random mutagenesis in the phGHam-g3p vector (also known as pS0643; see Example VIII).

We chose to use the "amber" hGH-g3 construct (called phGHam-g3p) because it appears to make the target protein, hGH, more accessible for binding. This is supported by data from comparative ELISA assays of monoclonal antibody binding. Phage produced from both pS0132 (S. Bass, R. Greene, J. A. Wells, *Proteins* 8, 309 (1990).) and phGHam-g3 were tested with three antibodies (Medix 2, 1B5.G2, and 5 B7.C10) that are known to have binding determinants near the carboxy-terminus of hGH [B. C. Cunningham, P. Jhurani, P. Ng, J. A. Wells, *Science* 243, 1330 (1989); B. C. Cunningham and J. A. Wells, *Science* 244, 1081 (1989); L. Jin and J. Wells. unpublished results], and one antibody (Medix 1) that recognizes determinants in helices 1 and 3 ([B. C. Cunningham, P. Jhurani, P. Ng, J. A. Wells, *Science* 243, 1330 (1989); B. C. Cunningham and J. A. Wells, *Science* 244, 1081 (1989)]). Phagemid particles from phGHam-g3 reacted much more strongly with antibodies Medix 2, 1B5.G2, and 5B7.C10 than did phagemid particles from pS0132. In particular, binding of pS0132 particles was reduced by >2000-fold for both Medix 2 and 5B7.C10 and reduced by >25-fold for 1B5.G2 compared to binding to Medix 1. On the other hand, binding of phGHam-g3 phage was weaker by only about 1.5-fold, 1.2-fold, and 2.3-fold for the Medix 2, 1B5.G2, and 5B7.C10 antibodies, respectively, compared with binding to MEDIX 1.

Construction of the helix 1 library by cassette mutagenesis

We mutated residues in helix 1 that were previously identified by alanine-scanning mutagenesis [B. C. Cunningham, P. Jhurani, P. Ng, J. A. Wells, *Science* 243, 1330 (1989); B. C. Cunningham and J. A. Wells, *Science* 244, 1081 (1989), 15, 16) to modulate the binding of the extracellular domains of the hGH and/or hPRL receptors (called hGHbp and hPRLbp, respectively). Cassette mutagenesis was carried out essentially as described [J. A. Wells, M. Vasser, D. B. Powers, *Gene* 34, 315 (1985)]. This library was constructed by cassette mutagenesis that fully mutated four residues at a time (see Example VIII) which utilized a mutated version of phGHam-g3 into which unique KpnI (at hGH codon 27) and XHoI (at hGH codon 6) restriction sites (underlined below) had been inserted by mutagenesis [T. A. Kunkel, J. D. Roberts, R. A. Zakour, *Methods Enzymol.* 154, 367–382] with the oligonucleotides 5'-GCC TTT GAC A<u>GG TAC C</u>AG GAG TTT G-3' (SEQ ID NO:19) and 5'-CCA ACT ATA CCA CT<u>C TCG AGG</u> TCT ATT CGA TAA C-3' (SEQ ID NO:20) respectively. The later oligo also introduced a +1 frameshift (italicized) to terminate translation from the starting vector and minimize wild-type background in the phagemid library. This strating vector was designated pH0508B. The helix 1 library, which mutated hGH residues 10, 14, 18, 21, was constructed by ligating to the large XhoI-KpnI fragment of pH0508B a cassette made from the complementary oligonucleotides 5'-pTCG AGG CTC NNS GAC AAC GCG NNS CTG CGT GCT NNS CGT CTT NNS CAG CTG GCC TTT GAC ACG TAC-3' (SEQ ID NO:21) and 5'-pGT GTC AAA GGC CAG CTG SNN AAG ACG SNN AGC ACG CAG SNN CGC GTT GTC SNN GAG CC-3' (SEQ ID NO:22). The KpnI site was destroyed in the junction of the ligation product so that restriction enzyme digestion could be used for analysis of non-mutated background.

The library contained at least $10^7$ independent transformants so that if the library were absolutely random ($10^6$ different combinations of codons) we would have an average of about 10 copies of each possible mutated hGH gene.

Restriction analysis using KpnI indicated that at least 80% of helix 1 library constructs contained the inserted cassette.

Binding enrichments of hGH-phage from the libraries was carried out using hGHbp immobilized on oxirane-polyacrylamide beads (Sigma Chemical Co.) as described (Example VIII). Four residues in helix 1 (F10, M14, H18, and H21) were similarly mutated and after 4 and 6 cycles a non-wild-type consensus developed (Table VIII). Position 10 on the hydrophobic face of helix 1 tended to be hydrophobic whereas positions 21 and 18 on the hydrophilic face tended were dominated by Asn; no obvious consensus was evident for position 14 (Table IX).

The binding constants for these mutants of hGH to hGHbp was determined by expressing the free hormone variants in the non-suppressor *E. coli* strain 16C9, purifying the protein, and assaying by competitive displacement of labelled wt-hGH from hGHbp (see Example VIII). As indicated, several mutants bind tighter to hGHbp than does wt-hGH.

TABLE VIII

Selection of hGH helix 1 mutants
Variants of hGH (randomly mutated at residues F10, M14, H18, H21) expressed on phagemid particles were selected by binding to hGHbp-beads and eluting with hGH (0.4 mM) buffer followed by glycine (0.2M, pH 2) buffer (see Example VIII).

| | Gly elution | | |
|---|---|---|---|
| F10 | M14 | H18 | H21 |
| 4 Cycles | | | |
| H | G | N | N |
| A | W | D | N (2) |
| Y | T | V | N |
| I | N | I | N |
| L | N | S | H |
| F | S | F | G |
| 6 Cycles | | | |
| H | G | N | N (6) |
| F | S | F | L |
| Consensus: | | | |
| H | G | N | N |

TABLE IX

Consensus sequences from the selected helix 1 library
Observed frequency is fraction of all clones sequenced with the indicated amino acid. The nominal frequency is calculated on the basis of NNS 32 codon degeneracy. The maximal enrichment factor varies from 11 to 32 depending upon the nominal freuency value for a given residue. Values of [$K_d$(Ala mut)/$K_d$ (wt hGH)] for single alanine mutations were taken from B. C. Cunningham and J. A. Wells, Science 244, 1081 (1989); B. C. Cunningham, D. J. Henner, J. A. Wells, Science 247, 1461 (1990); B. C. Cunningham and J. A. Wells, Proc. Natl. Acad. Sci. USA 88, 3407 (1991).

| Wild type residue | $\frac{K_d(\text{Ala mut})}{K_d(\text{wt hGH})}$ | Selected residue | Frequency observed | nominal | Enrichment |
|---|---|---|---|---|---|
| F10 | 5.9 | H | 0.50 | 0.031 | 17 |
| | | F | 0.14 | 0.031 | 5 |
| | | A | 0.14 | 0.062 | 2 |
| M14 | 2.2 | G | 0.50 | 0.062 | 8 |
| | | W | 0.14 | 0.031 | 5 |
| | | N | 0.14 | 0.031 | 5 |
| | | S | 0.14 | 0.093 | 2 |

TABLE IX-continued

Consensus sequences from the selected helix 1 library
Observed frequency is fraction of all clones sequenced with the indicated amino acid. The nominal frequency is calculated on the basis of NNS 32 codon degeneracy. The maximal enrichment factor varies from 11 to 32 depending upon the nominal freuency value for a given residue. Values of [$K_d$(Ala mut)/$K_d$ (wt hGH)] for single alanine mutations were taken from B. C. Cunningham and J. A. Wells, Science 244, 1081 (1989); B. C. Cunningham, D. J. Henner, J. A. Wells, Science 247, 1461 (1990); B. C. Cunningham and J. A. Wells, Proc. Natl. Acad. Sci. USA 88, 3407 (1991).

| Wild type residue | $\frac{K_d(\text{Ala mut})}{K_d(\text{wt hGH})}$ | Selected residue | Frequency observed | nominal | Enrichment |
|---|---|---|---|---|---|
| H18 | 1.6 | N | 0.50 | 0.031 | 17 |
|  |  | D | 0.14 | 0.031 | 5 |
|  |  | F | 0.14 | 0.031 | 5 |
| H21 | 0.33 | N | 0.79 | 0.031 | 26 |
|  |  | H | 0.07 | 0.031 | 2 |

TABLE X

Binding of purified hGH helix 1 mutants to hGHbp
Competition binding experiments were performed using [$^{125}$I] hGH (wild-type), hGHbp (containing the extracellular receptor domain, residues 1–238), and Mab263 [B. C. Cunningham, P. Jhurani, P. Ng, J. A. Wells, Science 243, 1330 (1989)]. The number P indicates the fractional occurrence of each mutant among all the clones sequences after one or more rounds of selection.

| Sequence position | | | | P | $K_d$ (nM) | f ($K_d$ mut) | $K_d$ (wt hGH)) |
|---|---|---|---|---|---|---|---|
| 10 | 14 | 18 | 21 | | | | |
| H | G | N | N | 0.50 | 0.14 ± 0.04 | | 0.42 |
| A | W | D | N | 0.14 | 0.10 ± 0.03 | | 0.30 |
| wtz F | M | H | H | 0 | 0.34 ± 0.05 | | (1) |
| F | S | F | L | 0.07 | 0.68 ± 0.19 | | 2.0 |
| Y | T | V | N | 0.07 | 0.75 ± 0.19 | | 2.2 |
| L | N | S | H | 0.07 | 0.82 ± 0.20 | | 2.4 |
| I | N | I | N | 0.07 | 1.2 ± 0.31 | | 3.4 |

EXAMPLE X

SELECTION OF hGH VARIANTS FROM A HELIX-4 RANDOM CASSETTE LIBRARY CONTAINING PREVIOUSLY FOUND MUTATIONS BY ENRICHMENT OF HORMONE-PHAGE

Design of mutant proteins with Improved binding properties by Iterative selection using hormone-phage Our experience with recruiting non-binding homologs of hGH evolutionary variants suggests that many individual amino acid substitutions can be combined to yield cumulatively improved mutants of hGH with respect to binding a particular receptor [B. C. Cunningham, D. J. Henner, J. A. Wells, Science 247, 1461 (1990); B. C. Cunningham and J. A. Wells, Proc. Natl. Acad. Sci. USA 88, 3407 (1991); H. B. Lowman, B. C. Cunningham, J. A. Wells, J. Biol. Chem. 266, (1991).

The helix 4b library was constructed in an attempt to further improve the helix 4 double mutant (E174S/F176Y) selected from the helix 4a library that we found bound tighter to the hGH receptor (see Example VIII). With the E174S/F176Y hGH mutant as the background starting hormone, residues were mutated that surrounded positions 174 and 176 on the hydrophilic face of helix 4 (R167, D171, T175 and I179).

Construction of the helix 4b library by cassette mutagenesis

Cassette mutagenesis was carried out essentially as described [J. A. Wells, M. Vasser, D. B. Powers, Gene 34, 315 (1985)]. The helix 4b library, which mutated residues 167, 171, 175 and 179 within the E174S/F176Y background, was constructed using cassette mutagenesis that fully mutated four residues at a time (see Example VIII) and which utilized a mutated version of phGHam-g3 into which unique BstEII and BglII restriction sites had been inserted previously (Example VIII). Into the BstEII-BGIII sites of the vector was inserted a cassette made from the complementary oligonucleotides 5'-pG TTA CTC TAC TGC TTC NNS AAG GAC ATG NNS AAG GTC AGC NNS TAC CTG CGC NNS GTG CAG TGC A-3' (SEQ ID NO:23) and 5'-pGA TCT GCA CTG CAC SNN GCG CAG GTA SNN GCT GAC CTT SNN CAT GTC CTT SNN GAA GCA GTA GA-3' (SEQ ID NO:24). The BstEII site was eliminated in the ligated cassette. From the helix 4b library, 15 unselected clones were sequenced. Of these, none lacked a cassette insert, 20% were frame-shifted, and 7% had a non-silent mutation.

Results of hGHbp enrichment

Binding enrichments of hGH-phage from the libraries was carried out using hGHbp immobilized on oxirane-polyacrylamide beads (Sigma Chemical Co.) as described (Example VIII). After 6 cycles of binding a reasonably clear consensus developed (Table XI). Interestingly, all positions tended to contain polar residues, notably Ser, Thr and Asn (XII).

Assay of hGH mutants

The binding constants for some of these mutants of hGH to hGHbp was determined by expressing the free hormone variants in the non-suppressor E. coli strain 16C9, purifying the protein, and assaying by competitive displacement of labelled wt-hGH from hGHbp (see Example VIII). As indicated, the binding affinities of several helix-4b mutants for hGHbp were tighter than that of wt-hGH (Table XIII).

Receptor-selectivity of hGH variants

Finally, we have begun to analyze the binding affinity of several of the tighter hGHbp binding mutants for their ability to bind to the hPRLbp. The E174S/F176Y mutant binds 200-fold weaker to the hPRLbp than hGH. The E174T/F176Y/R178K and R167N/D171S/E174S/F176Y/I179T mutants each bind >500-fold weaker to the hPRLbp than hGH. Thus, it is possible to use the produce new receptor selective mutants of hGH by phage display technology.

Hormone-phagemid selection identifies the information-content of particular residues Of the 12 residues mutated in three hGH-phagemid libraries (Examples VIII, IX, X), 4 showed a strong, although not exclusive, conservation of the wild-type residues (K172, T175, F176, and R178). Not surprisingly, these were residues that when converted to Ala caused the largest disruptions (4- to 60-fold) in binding affinity to the hGHbp. There was a class of 4 other residues (F10, M14, D171, and I179) where Ala substitutions caused weaker effects on binding (2- to 7-fold) and these positions exhibited little wild-type consensus. Finally the other 4 residues (H18, H21, R167, and E174), that promote binding to the hPRLbp but not the hGHbp, did not exhibit any consensus for the wild-type hGH sequence by selection on hGHbp-beads. In fact two residues (E174 and H21), where Ala substitutions enhance binding affinity to the hGHbp by 2- to 4-fold [B. C. Cunningham, P. Jhurani, P. Ng, J. A. Wells, Science 243, 1330 (1989); B. C.

Cunningham and J. A. Wells, *Science* 244, 1081 (1989); B. C. Cunningham, D. J. Henner, J. A. Wells, *Science* 247, 1461 (1990); B. C. Cunningham and J. A. Wells, *Proc. Natl. Acad. Sci. USA* 88, 3407 (1991)]. Thus, the alanine-scanning mutagenesis data correlates reasonably well with the flexibility to substitute each position. In fact, the reduction in binding affinity caused by alanine substitutions [B. C. Cunningham, P. Jhurani, P. Ng, J. A. Wells, *Science* 243, 1330 (1989); B. C. Cunningham and J. A. Wells, *Science* 244, 1081 (1989)], B. C. Cunningham, D. J. Henner, J. A. Wells, *Science* 247, 1461 (1990); B. C. Cunningham and J. A. Wells, *Proc. Natl. Acad. Sci. USA* 88, 3407 (1991)] is a reasonable predictor of the percentage that the wild-type residue is found in the phagemid pool after 3–6 rounds of selection. The alanine-scanning information is useful for targeting side-chains that module binding, and the phage selection is appropriate for optimizing them and defining the flexibility of each site (and/or combinations of sites) for substitution. The combination of scanning mutational methods [B. C. Cunningham, P. Jhurani, P. Ng, J. A. Wells, *Science* 243, 1330 (1989); B. C. Cunningham and J. A. Wells, *Science* 244, 1081 (1989)] and phage display is a powerful approach to designing receptor-ligand interfaces and studying molecular evolution in vitro.

Variations on iterative enrichment of hormone-phagemid libraries

In cases where combined mutations in hGH have additive effects on binding affinity to receptor, mutations learned through hormone-phagemid enrichment to improve binding can be combined by simple cutting and ligation of restriction fragments or mutagenesis to yield cumulatively optimized mutants of hGH.

On the other hand, mutations in one region of hGH which optimize receptor binding may be structurally or functionally incompatible with mutations in an overlapping or another region of the molecule. In these cases, hormone phagemid enrichment can be carried out by one of several variations on the iterative enrichment approach: (1) random DNA libraries can be generated in each of two (or perhaps more) regions of the molecule by cassette or another mutagenesis method. Thereafter, a combined library can be created by ligation of restriction fragments from the two DNA libraries; (2) an hGH variant, optimized for binding by mutation in one region of the molecule, can be randomly mutated in a second region of the molecule as in the helix-4b library example; (3) two or more random libraries can be partially selected for improved binding by hormone-phagemid enrichment; after this "roughing-in" of the optimized binding site, the still-partially-diverse libraries can be recombined by ligation of restriction fragments to generate a single library, partially diverse in two or more regions of the molecules, which in turn can be further selected for optimized binding using hormone-phagemid enrichment.

TABLE XI

Mutant phagemids of hGH selected from helix 4b library after 4 and 6 cycles of enrichment.
Selection of hGH helix 4b mutants (randomly mutated at residues 167, 171, 175, 179), each containing the E174S/F176Y double mutant, by binding to hGHbp-beads and eluting with hGH (0.4 mM) buffer followed by glycine (0.2M, pH 2) buffer. One mutant (+) contained the spurious mutation R178H.

| R167 | D171 | T175 | I179 |
|------|------|------|------|
| 4 Cycles | | | |
| N | S | T | T |
| K | S | T | T |
| S | N | T | T |
| D | S | T | T |
| D | S | T | T + |
| D | S | A | T |
| D | S | A | N |
| T | D | T | T |
| N | D | T | N |
| A | N | T | N |
| A | S | T | T |
| 6 Cycles | | | |
| N | S | T | T (2) |
| N | N | T | T |
| N | S | T | Q |
| D | S | S | T |
| E | S | T | I |
| K | S | T | L |
| Consensus: | | | |
| N | S | T | T |
|   | D |   | N |

TABLE XII

Consensus sequences from the selected library.
Observed frequency is fraction of all clones sequenced with the indicated amino acid. The nominal frequency is calculated on the basis of NNS 32 codon degeneracy. The maximal enrichment factor varies from 11 to 16 to 32 depending upon the nominal frequency value for a given residue. Values of [$K_d$ (Ala mut)/$K_d$ (wt hGH)] for single alanine mutatins were taken from refs. below; for position 175 we only have a value for the T175S mutant [B. C. Cunningham, P. Jhurani, P. Ng, J. A. Wells, Science 243, 1330 (1989); B. C. Cunningham and J. A. Wells, Science 244, 1081 (1989); B. C. Cunningham, D. J. Henner, J. A. Wells, Science 247, 1461 (1990); B. C. Cunningham and J. A. Wells, Proc. Natl. Acad. Sci. USA 88, 3407 (1991).]

| Wild type residue | $K_d$(Ala mut)/$K_d$(wt hGH) | Selected residue | Frequency observed | nominal | Enrichment |
|------|------|------|------|------|------|
| R167 | 0.75 | N | 0.35 | 0.031 | 11 |
|      |      | D | 0.24 | 0.031 | 8 |
|      |      | K | 0.12 | 0.031 | 4 |
|      |      | A | 0.12 | 0.062 | 2 |
| D171 | 7.1  | S | 0.76 | 0.093 | 8 |
|      |      | N | 0.18 | 0.031 | 6 |
|      |      | D | 0.12 | 0.031 | 4 |
| T175 | 3.5  | T | 0.88 | 0.062 | 14 |
|      |      | A | 0.12 | 0.031 | 4 |
| I179 | 2.7  | T | 0.71 | 0.062 | 11 |
|      |      | N | 0.18 | 0.031 | 6 |

TABLE XIII

Binding of purified hGH mutants to hGHbp.
Competition binding experiments were performed using [$^{125}$I]hGH (wild-type), hGHbp (containing the extracellular receptor domain, residues 1–238), and Mab263 (11). The number P indicates the fractional occurrence of each mutant among all the clones sequenced after one or more rounds of selection. Note that the helix 5b mutations (*) are in the background of hGH (E174S/F176Y). In the list of helix 4b mutants, the E174S/F176Y mutant (*), with wt residues at 167, 171, 175, 179, is shown in bold.

| Sequence position | | | | P | $K_d$ (nM) | $\frac{K_d(\text{Ala mut})}{K_d(\text{wt hGH})}$ |
|---|---|---|---|---|---|---|
| * 167 | * 171 | * 175 | * 179 | | | |
| N | S | T | T | 0.18 | 0.04 ± 0.02 | 0.12 |
| E | S | T | I | 0.06 | 0.04 ± 0.02 | 0.12 |
| K | S | T | L | 0.06 | 0.05 ± 0.03 | 0.16 |
| N | N | T | T | 0.06 | 0.06 ± 0.03 | 0.17 |
| R | D | T | I | 0 | 0.06 ± 0.01 | (0.18) |
| N | S | T | Q | 0.06 | 0.26 ± 0.11 | 0.77 |

EXAMPLE XI

Assembly of F$_{ab}$ Molecule on the Phagemid Surface

Construction of plasmids

Plasmid pDH 188 contains the DNA encoding the F$_{ab}$ portion of a humanized IgG antibody, called 4D5, that recognizes the HER-2 receptor. This plasmid is contained in E. coli strain SR 101, and has been deposited with the ATCC in Rockville, Md.

Briefly, the plasmid was prepared as follows: the starting plasmid was pS0132, containing the alkaline phosphatase promoter as described above. The DNA encoding human growth hormone was excised and, after a series of manipulations to make the ends of the plasmid compatible for ligation, the DNA encoding 4D5 was inserted. The 4D5 DNA contains two genes. The first gene encodes the variable and constant regions of the light chain, and contains at its 5' end the DNA encoding the st II signal sequence. The second gene contains four portions: first, at its 5' end is the DNA encoding the st II signal sequence. This is followed by the DNA encoding the variable domain of the heavy chain, which is followed by the DNA encoding the first domain of the heavy chain constant region, which in turn is followed by the DNA encoding the M13 gene III. The salient features of this construct are shown in FIG. 10. The sequence of the DNA encoding 4D5 is shown in FIG. 11.

E. coli transformation and phage production

Both polyethylene glycol (PEG) and electroporation were used to transform plasmids into SR101 cells. (PEG competent cells were prepared and transformed according to the method of Chung and Miller (Nucleic Acids Res. 16:3580 [1988]). Cells that were competent for electroporation were prepared, and subsequently transformed via electroporation according to the method of Zabarovsky and Winberg (Nucleic Acids Res. 18:5912 [1990]). After placing the cells in 1 ml of the SOC media (described in Sambrook et al., supra), they were grown for 1 hour at 37° C. with shaking. At this time, the concentration of the cells was determined using light scattering at OD$_{600}$. A titered K07 phage stock was added to achieve an multiplicity of infection (MOI) of 100, and the phage were allowed to adhere to the cells for 20 minutes at room temperature. This mixture was then diluted into 25 mls of 2YT broth (described in Sambrook et al., supra) and incubated with shaking at 37° C. overnight. The next day, cells were pelleted by centrifugation at 5000×g for 10 minutes, the supernatant was collected, and the phage particles were precipitated with 0.5M NaCl and 4% PEG (final concentration) at room temperature for 10 minutes. Phage particles were pelleted by centrifugation at 10,000×g for 10 minutes, resuspended in 1 ml of TEN (10 mM Tris, pH 7.6, 1 mM EDTA, and 150 mM NaCl), and stored at 4° C.

Production of antigen coated plates

Aliquots of 0.5 ml from a solution of 0.1 mg/ml of the extra-cellular domain of the HER-2 antigen (ECD) or a solution of 0.5 mg/ml of BSA (control antigen) in 0.1M sodium bicarbonate, pH 8.5 were used to coat one well of a Falcon 12 well tissue culture plate. Once the solution was applied to the wells, the plates were incubated at 4° C. on a rocking platform overnight. The plates were then blocked by removing the initial solution, applying 0.5 ml of blocking buffer (30 mg/ml BSA in 0.1M sodium bicarbonate), and incubating at room temperature for one hour. Finally, the blocking buffer was removed, 1 ml of buffer A (PBS, 0.5% BSA, and 0.05% Tween-20) was added, and the plates were stored up to 10 days at 4° C. before being used for phage selection.

Phage selection process

Approximately 10$^9$ phage particles were mixed with a 100-fold excess of K07 helper phage and 1 ml of buffer A. This mixture was divided into two 0.5 ml aliquots; one of which was applied to ECD coated wells, and the other was applied to BSA coated wells. The plates were incubated at room temperature while shaking for one to three hours, and were then washed three times over a period of 30 minutes with 1 ml aliquots of buffer A. Elution of the phage from the plates was done at room temperature by one of the two methods: 1) an initial overnight incubation of 0.025 mg/ml purified Mu4D5 antibody (murine) followed by a 30 minute incubation with 0.4 ml of the acid elution buffer (0.2M glycine, pH 2.1, 0.5% BSA, and 0.05% Tween-20), or 2) an incubation with the acid elution buffer alone. Eluates were then neutralized with 1M Tris base, and a 0.5 ml aliquot of TEN was added. These samples were then propagated, titered, and stored at 4° C.

Phage propagation

Aliquots of eluted phage were added to 0.4 ml of 2YT broth and mixed with approximately 10$^8$ mid-log phase male E. coli strain SR101. Phage were allowed to adhere to the cells for 20 minutes at room temperature and then added to 5 ml of 2YT broth that contained 50 µg/ml of carbenicillin and 5 µg/ml of tetracycline. These cells were grown at 37° C. for 4 to 8 hours until they reached mid-log phase. The OD$_{600}$ was determined, and the cells were superinfected with K07 helper phage for phage production. Once phage particles were obtained, they were titered in order to determine the number of colony forming units (cfu). This was done by taking aliquots of serial dilutions of a given phage stock, allowing them to infect mid-log phase SR101, and plating on LB plates containing 50 µg/ml carbenicillin.

RIA affinity determination

Figure 13:
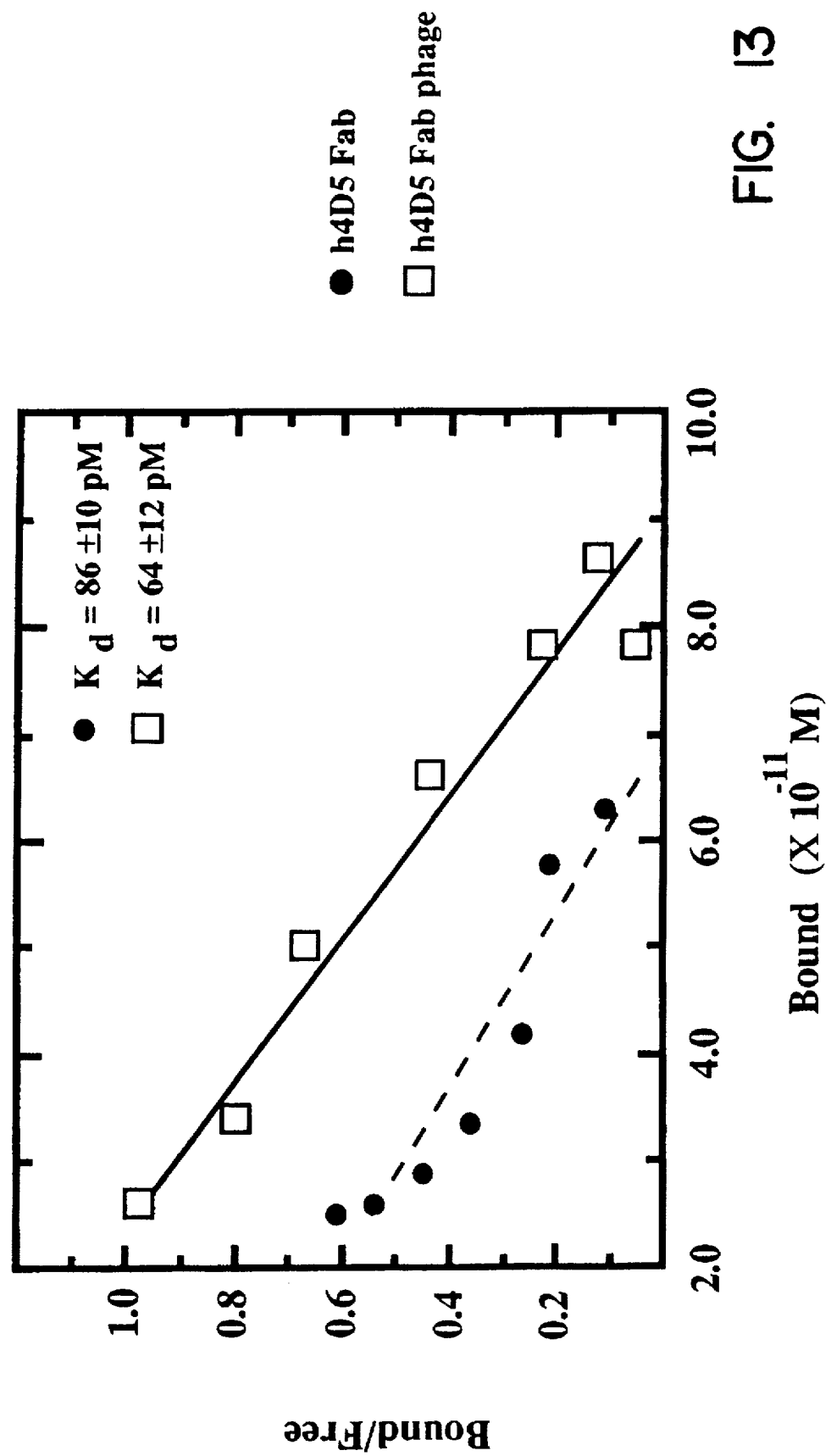
FIG. 13. The Scatchard analysis of the RIA affinity determination described in Experimental Protocols is shown here. The amount of labeled ECD antigen that is bound is shown on the x-axis while the amount that is bound divided by the amount that is free is shown on the y-axis. The slope of the line indicates the $K_a$; the calculated $K_d$ is $1/K_a$.

The affinity of h4D5 F$_{ab}$ fragments and F$_{ab}$ phage for the ECD antigen was determined using a competitive receptor binding RIA (Burt, D. R., Receptor Binding in Drug Research. O'Brien, R. A. (Ed.), pp. 3–29, Dekker, N.Y. [1986]). The ECD antigen was labeled with $^{125}$-Iodine using the sequential chloramine-T method (De Larco, J. E. et al., J. Cell. Physiol. 109:143–152 [1981]) which produced a radioactive tracer with a specific activity of 14 µCi/µg and incorporation of 0.47 moles of Iodine per mole of receptor. A series of 0.2 ml solutions containing 0.5 ng (by ELISA) of $F_{ab}$ or $F_{ab}$ phage, 50 nCi of $^{125}I$ ECD tracer, and a range of unlabeled ECD amounts (6.4 ng to 3277 ng) were prepared and incubated at room temperature overnight. The labeled ECD-$F_{ab}$ or ECD-$F_{ab}$ phage complex was separated from the unbound labeled antigen by forming an aggregate complex induced by the addition of an anti-human IgG (Fitzgerald 40-GH23) and 6% PEG 8000. The complex was pelleted by centrifugation (15,000×g for 20 minutes) and the amount of labeled ECD (in cpm) was determined by a gamma counter. The dissociation constant ($K_d$) was calculated by employing a modified version of the program LIGAND (Munson, P. and Rothbard, D., *Anal. Biochem.* 107:220–239 [1980]) which utilizes Scatchard analysis (Scatchard, G., *Ann. N.Y. Acad. Sci.* 51:660–672 [1949]). The Kd values are shown in FIG. 13.

Competitive cell binding assay

Murine 4D5 antibody was labeled with 125-I to a specific activity of 40–50 µCi/µg using the Iodogen procedure. Solutions containing a constant amount of labeled antibody and increasing amounts of unlabeled variant Fab were prepared and added to near confluent cultures of Sk-BR-3 cells grown in 96-well microtiter dishes (final concentration of labeled antibody was 0.1 nM). After an overnight incubation at 4° C., the supernatant was removed, the cells were washed and the cell associated radioactivity was determined in a gamma counter. $K_d$ values were determined by analyzing the data using a modified version of the program LIGAND (Munson, P. and Rothbard, D., supra).

EXAMPLE XII

SELECTION OF hGH VARIANTS FROM COMBINATIONS OF HELIX-1 AND HELIX-4 HORMONE-PHAGE VARIANTS

Construction of additive variants of hGH

According to additivity principles [J. A. Wells, *Biochemistry* 29, 8509 (1990)], mutations in different parts of a protein, if they are not mutually interacting, are expected to combine to produce additive changes in the free energy of binding to another molecule (changes are additive in terms of $\Delta\Delta G_{binding}$, or multiplicative in terms of $K_d$=exp(–$\Delta G$/RT]). Thus a mutation producing a 2-fold increase in binding affinity, when combined with a second mutation causing a 3-fold increase, would be predicted to yield a double mutant with a 6-fold increased affinity over the starting variant.

To test whether multiple mutations obtained from hGH-phage selections would produce cumulatively favorable effects on hGHbp (hGH-binding protein; the extracellular domain of the hGH receptor) binding, we combined mutations found in the three tightest-binding variants of hGH from the helix-1 library (Example IX: F10A/M14W/H18D/H21N, F10H/M14G/H18N/H21N, and F10F/M14S/H18F/H21L) with those found in the three tightest binding variants found in the helix-4b library (Example X: R167N/D171S/T175/I179T, R167E/D171S/T175/I179, and R167N/D171N/T175/I179T).

hGH-phagemid double-stranded DNA (dsDNA) from each of the one-helix variants was isolated and digested with the restriction enzymes EcoRI and BstXI. The large fragment from each helix-4b variant was then isolated and ligated with the small fragment from each helix-1 variant to yield the new two-helix variants shown in Table XIII. All of these variants also contained the mutations E174S/F176Y obtained in earlier hGH-phage binding selections (see Example X for details).

Construction of selective combinatorial libraries of hGH

Although additivity principles appear to hold for a number of combinations of mutations, some combinations (e.g. E174S with F176Y) are clearly non-additive (see Examples VIII and X). In order to identify with certainty the tightest binding variant with, for example, 4 mutations in helix-1 and 4 mutations in helix-4, one would ideally mutate all 8 residues at once and then sort the pool for the globally tightest binding variant. However, such a pool would consist of $1.1 \times 10^{12}$ DNA sequences (utilizing NNS codon degeneracy) encoding $2.6 \times 10^{10}$ different polypeptides. Obtaining a random phagemid library large enough to assure representation of all variants (perhaps $10^{13}$ transformants) is not practical using current transformation technology.

We have addressed this difficulty first by utilizing successive rounds of mutagenesis, taking the tightest binding variant from one library, then mutating other residues to further improve binding (Example X). In a second method, we have utilized the principle of additivity to combine the best mutations from two independently sorted libraries to create multiple mutants with improved binding (described above). Here, we further searched through the possible combinations of mutations at positions 10, 14, 18, 21, 167, 171, 175, and 179 in hGH, by creating combinatorial libraries of random or partially-random mutants. We constructed three different combinatorial libraries of hGH-phagemids, using the pooled phagemids from the helix 1 library (independently sorted for 0, 2, or 4 cycles; Example IX) and the pool from the helix-4b library (independently sorted for 0, 2, or 4 cycles; Example X) and sorted the combined variant pool for hGHbp binding. Since some amount of sequence diversity exists in each of these pools, the resulting combinatorial library can explore more sequence combinations than what we might construct manually (e.g. Table XIII).

hGH-phagemid double-stranded DNA (dsDNA) from each of the one-helix library pools (selected for 0, 2, or 4 rounds) was isolated and digested with the restriction enzymes AccI and BstXI. The large fragment from each helix-1 variant pool was then isolated and ligated with the small fragment from each helix-4b variant pool to yield the three combinatorial libraries pH0707A (unselected helix 1 and helix 4b pools, as described in examples IX and X), pH0707B (twice-selected helix-1 pool with twice-selected helix-4b pool), and pH0707C (4-times selected helix-1 pool with 4-times selected helix-4b pool). Duplicate ligations were also set up with less DNA and designated as pH0707D, pH0707E, and pH0707F, corresponding to the 0-, 2-, and 4-round starting libraries respectively. All of these variant pools also contained the mutations E174S/F176Y obtained in earlier hGH-phage binding selections (see Example X for details).

Sorting combinatorial libraries of hGH-phage variants

The ligation products pH0707A–F were processed and electro-transformed in XL1-Blue cells as described (Example VIII). Based on colony-forming units (CFU), the number of transformants obtained from each pool was as follows: $2.4 \times 10^6$ from pH0707A, $1.8 \times 10^6$ from pH0707B, $1.6 \times 10^6$ from pH0707C, $8 \times 10^5$ from pH0707D, $3 \times 10^5$ from pH0707E, and $4 \times 10^5$ from pH0707F. hGH-phagemid particles were prepared and selected for hGHbp-binding over 2 to 7 cycles as described in Example VIII.

Rapid sorting of hGH-phagemid libraries

In addition to sorting phagemid libraries for tight-binding protein variants, as measured by equilibrium binding affinity, it is of interest to sort for variants which are altered in either the on-rate ($k_{on}$) or the off-rate ($k_{off}$) of binding to a receptor or other molecule. From thermodynamics, these rates are related to the equilibrium dissociation constant, $K_d=(k_{off}/k_{on})$. We envision that certain variants of a particular protein have similar $K_d$'s for binding while having very different $k_{on}$'s and $k_{off}$'s. Conversely, changes in $K_d$ from one variant to another may be due to effects on $k_{on}$, effects on $k_{off}$, or both. The pharmacological properties of a protein may be dependent on binding affinity or on $k_{on}$ or $k_{off}$, depending on the detailed mechanism of action. Here, we sought to identify hGH variants with higher on-rates to investigate the effects of changes in $k_{on}$. We envision that the selection could alternatively be weighted toward $k_{off}$ by increasing the binding time and increasing the wash time and/or concentration with cognate ligand (hGH).

From time-course analysis of wild-type hGH-phagemid binding to immobilized hGHbp, it appears that, of the total hGH-phagemid particles that can be eluted in the final pH 2 wash (see Example VIII for the complete binding and elution protocol), less than 10% are bound after 1 minute of incubation, while greater than 90% are bound after 15 minutes of incubation.

For "rapid-binding selection," phagemid particles from the pH0707B pool (twice-selected for helices 1 and 4 independently) were incubated with immobilized hGHbp for only 1 minute, then washed six times with 1 mL of binding buffer; the hGH-wash step was omitted; and the remaining hGH-phagemid particles were eluted with a pH2 (0.2M glycine in binding buffer) wash. Enrichment of hGH-phagemid particles over non-displaying particles indicated that even with a short binding period and no cognate-ligand (hGH) challenge, hGH-phagemid binding selection sorts tight-binding variants out of a randomized pool.

Assay of hGH mutants

The binding constants for some of these mutants of hGH to hGHbp was determined by expressing the free hormone variants in the non-suppressor *E. coli* strain 16C9 or 34B8, purifying the protein, and assaying by competitive displacement of labelled wt-hGH from hGHbp (see Example VIII) in a radio-immunoprecipitation assay. In Table XIII-A below, all the variants have glutamate$_{174}$ replaced by serine$_{174}$ and phenylalanine$_{176}$ replaced by tyrosine$_{176}$ (E174S and F1176Y) plus the additional substitutions as indicated at hGH amino acid positions 10, 14, 18, 21, 167, 171, 175 and 179.

TABLE XIII-A

| hGH variants from addition of helix-1 and helix-4b mutations | | | | | | | | |
|---|---|---|---|---|---|---|---|---|
| wild-type | Helix 1 | | | | Helix 4 | | | |
| residue: | F10 | M14 | H18 | H21 | R167 | D171 | T175 | I179 |
| Variant | | | | | | | | |
| H0650AD | H | G | N | N | N | S | T | T |
| H0650AE | H | G | N | N | E | S | T | I |
| H0650AF | H | G | N | N | N | N | T | T |
| H0650BD | A | W | D | N | N | S | T | T |
| H0650BE | A | W | D | N | E | S | T | I |
| H0650BF | A | W | D | N | N | N | T | T |
| H0650CD | F | S | F | L | N | S | T | T |
| H0650CD | F | S | F | L | E | S | T | I |
| H0650CD | F | S | F | L | N | N | T | T |

In Table XIV below, hGH variants were selected from combinatorial libraries by the phagemid binding selection process. All hGH variants in Table XIV contain two background mutations (E174S/F176Y). hGH-phagemid pools from the libraries pH0707A (Part A), pH0707B and pH0707E (Part B), or pH0707C (Part C) were sorted for 2 to 7 cycles for binding to hGHbp. The number P indicates the fractional occurrence of each variant type among the set of clones sequenced from each pool.

TABLE XIV

| hGH variants from hormone-phagemid binding selection of combinatorial libraries. | | | | | | | | | |
|---|---|---|---|---|---|---|---|---|---|
| | wild-type residue: | F10 | M14 | H18 | H21 | R167 | D171 | T175 | I179 |
| | | | | Helix 1 | | | | Helix 4 | |
| P | Variant | | | | | | | | |
| Part A: | | | | | | | | | |
| | 4 cycles: | | | | | | | | |
| 0.60 | H0714A.1 | H | G | N | N | N | S | T | N |
| 0.40 | H0714A.4 | A | N | D | A | N | N | T | N* |
| Part B: | | | | | | | | | |
| | 2 cycles: | | | | | | | | |
| 0.13 | H0712B.1 | F | S | F | G | H | S | T | T |
| 0.13 | H0712B.2 | H | Q | T | S | A | D | N | S |
| 0.13 | H0712B.4 | H | G | N | N | N | A | T | T |
| 0.13 | H0712B.5 | F | S | F | L | S | D | T | T |
| 0.13 | H0712B.6 | A | S | T | N | R | D | T | I |
| 0.13 | H0712B.7 | Q | Y | N | N | H | S | T | T |
| 0.13 | H0712B.8 | W | G | S | S | R | D | T | I |
| 0.13 | H0712E.1 | F | L | S | S | K | N | T | V |
| 0.13 | H0712E.2 | W | N | N | S | H | S | T | T |
| 0.13 | H0712E.3 | A | N | A | S | N | S | T | T |
| 0.13 | H0712E.4 | P | S | D | N | R | D | T | I |
| 0.13 | H0712E.5 | H | G | N | N | N | N | T | S |
| 0.13 | H0712E.6 | F | S | T | G | R | D | T | I |

TABLE XIV-continued hGH variants from hormone-phagemid binding selection of combinatorial libraries.

| | | Helix 1 | | | | Helix 4 | | | |
|---|---|---|---|---|---|---|---|---|---|
| | wild-type residue: | F10 | M14 | H18 | H21 | R167 | D171 | T175 | I179 |
| 0.13 | H0712E.7 | M | T | S | N | Q | S | T | T |
| 0.13 | H0712E.8 | F | S | F | L | T | S | T | S |
| 4 cycles: | | | | | | | | | |
| 0.17 | H0714B.1 | A | W | D | N | R | D | T | I |
| 0.17 | H0714B.2 | A | W | D | N | H | S | T | N |
| 0.17 | H0714B.3 | M | Q | M | N | N | S | T | T |
| 0.17 | H0714B.4 | H | Y | D | H | R | D | T | T |
| 0.17 | H0714B.5 | L | N | S | H | R | D | T | I |
| 0.17 | H0714B.6 | L | N | S | H | T | S | T | T |
| 7 cycles: | | | | | | | | | |
| 0.57 | H0717B.1 | A | W | D | N | N | A | T | T |
| 0.14 | H0717B.2 | F | S | T | G | R | D | T | I |
| 0.14 | H0717B.6 | A | W | D | N | R | D | T | I |
| 0.14 | H0717B.7 | I | Q | E | H | N | S | T | T |
| 0.50 | H0717E.1 | F | S | L | A | N | S | T | V |
| Part C: | | | | | | | | | |
| 4 cycles: | | | | | | | | | |
| 0.67 | H0714C.2 | F | S | F | L | K | D | T | T |

* = also contained the mutations L15R, K168R.

In Table XV below, hGH variants were selected from combinatorial libraries by the phagemid binding selection process. All hGH variants in Table XV contain two background mutations (E174S/F176Y). The number P is the fractional occurrence of a given variant among all clones sequenced after 4 cycles of rapid-binding selection.

TABLE XV hGH variants from RAPID hGHbp binding selection of an hGH-phagemid combinatorial library

| | | Helix 1 | | | | Helix 4 | | | |
|---|---|---|---|---|---|---|---|---|---|
| wild-type | residue: | F10 | M14 | H18 | H21 | R167 | D171 | T175 | I179 |
| P | Variant | | | | | | | | |
| 0.14 | H07BF4.2 | W | G | S | S | R | D | T | I |
| 0.57 | H07BF4.3 | M | A | D | N | N | S | T | T |
| 0.14 | H07BF4.6 | A | W | D | N | S | S | V | T‡ |
| 0.14 | H07BF4.7 | H | Q | T | S | R | D | T | I |

‡= also contained the mutation Y176F (wild-type hGH also contains F176).

In Table XVI below, binding constants were measured by competitive displacement of $^{125}$I-labelled hormone H0650BD or labelled hGH using hGHbp (1–238) and either Mab5 or Mab263. The variant H0650BD appears bind more than 30-fold tighter than wild-type hGH.

TABLE XVI

Equilibrium binding constants of selected hGH variants.

| hGH Variant | $\frac{Kd(variant)}{Kd(H0650BD)}$ | $\frac{Kd(variant)}{Kd(hGH)}$ | Kd (pM) |
|---|---|---|---|
| hGH | 32 | 1 | 340 ± 50 |
| H0650BD | 1 | 0.031 | 10 ± 3 |
| H0650BF | 1.5 | 0.045 | 15 ± 5 |
| H0714B.6 | 3.4 | 0.099 | 34 ± 19 |

TABLE XVI-continued

Equilibrium binding constants of selected hGH variants.

| hGH Variant | $\frac{Kd(variant)}{Kd(H0650BD)}$ | $\frac{Kd(variant)}{Kd(hGH)}$ | Kd (pM) |
|---|---|---|---|
| H0712B.7 | 7.4 | 0.22 | 74 ± 30 |
| H0712E.2 | 16 | 0.48 | 60 ± 70 |

EXAMPLE XIII

Selective enrichment of hGH-phage containing a protease substrate sequence versus non-substrate phage As described in Example I, the plasmid pS0132 contains the gene for hGH fused to the residue Pro198 of the gene III protein with the insertion of an extra glycine residue. This plasmid may be used to produce hGH-phage particles in which the hGH-gene III fusion product is displayed monovalently on the phage surface (Example IV). The fusion protein comprises the entire hGH protein fused to the carboxy terminal domain of gene III via a flexible linker sequence.

To investigate the feasibility of using phage display technology to select favorable substrate sequences for a given proteolytic enzyme, a genetically engineered variant of subtilisin BPN' was used. (Carter, P. et al., Proteins: Structure, function and genetics 6:240–248 (1989)). This variant (hereafter referred to as A64SAL subtilisin) contains the following mutations: Ser24Cys, His64Ala, Glu156Ser, Gly169Ala and Tyr217Leu. Since this enzyme lacks the essential catalytic residue His64, its substrate specificity is greatly restricted so that certain histidine-containing substrates are preferentially hydrolyzed (Carter et al., Science 237:394–399 (1987)).

Construction of a hGH-substrate-phage vector

The sequence of the linker region in pS0132 was mutated to create a substrate sequence for A64SAL subtilisin, using the oligonucleotide 5'-TTC-GGG-CCC-TTC-GCT-GCT-CAC-TAT-ACG-CGT-CAG-TCG-ACT-GAC-CTG-CCT-3' (SEQ ID NO:25). This resulted in the introduction of the protein sequence Phe-Gly-Pro-Phe-Ala-Ala-His-Tyr-Thr-Arg-Gin-Ser-Thr-Asp (SEQ ID NO:26) in the linker region between hGH and the carboxy terminal domain of gene III, where the first Phe residue in the above sequence is Phe191 of hGH. The sequence Ala-Ala-His-Tyr-Thr-Arg-Gin (SEQ ID NO:27) is known to be a good substrate for A64 SL subtilisin (Carter et al (1989), supra). The resulting plasmid was designated pS0640.

Selective enrichment of hGH-substrate-phage

Phagemid particles derived from pS0132 and pS0640 were constructed as described in Example I. In initial experiments, a 10 μl aliquot of each phage pool was separately mixed with 30 μl of oxirane beads (prepared as described in Example II) in 100 μl of buffer comprising 20 mM Tris-HCl pH 8.6 and 2.5M NaCl. The binding and washing steps were performed as described in Example VII. The beads were then resuspended in 400 μl of the same buffer, with or without 50 nM of A64SAL subtilisin. Following incubation for 10 minutes, the supernatants were collected and the phage titres (cfu) measured. Table XVII shows that approximately 10 times more substrate-containing phagemid particles (pS0640) were eluted in the presence of enzyme than in the absence of enzyme, or than in the case of the non-substrate phagemids (pS0132) in the presence or absence of enzyme. Increasing the enzyme, phagemid or bead concentrations did not improve this ratio.

Improvement of the selective enrichment procedure

In an attempt to decrease the non-specific elution of immobilized phagemids, a tight-binding variant of hGH was introduced in place of the wild-type hGH gene in pS0132 and pS0640. The hGH variant used was as described in Example XI (pH0650bd) and contains the mutations Phe10Ala, Met14Trp, His18Asp, His21Asn, Arg(167Asn, Asp171Ser, Glu174Ser, Phe176Tyr and Ile179Thr. This resulted in the construction of two new phagemids: pDM0390 (containing tight-binding hGH and no substrate sequence) and pDM0411 (containing tight-binding hGH and the substrate sequence Ala-Ala-His-Tyr-Thr-Arg-Gin) (SEQ ID NO:27). The binding washing and elution protocol was also changed as follows:

(i) Binding: COSTAR 12-well tissue culture plates were coated for 16 hours with 0.5 ml/well 2 ug/ml hGHbp in sodium carbonate buffer pH 10.0. The plates were then incubated with 1 ml/well of blocking buffer (phosphate buffered saline (PBS) containing 0.1% w/v bovine serum albumen) for 2 hours and washed in an assay buffer containing 10 mM Tris-HCl pH 7.5, 1 mM EDTA and 100 mM NaCl. Phagemids were again prepared as described in Example I: the phage pool was diluted 1:4 in the above assay buffer and 0.5 ml of phage incubated per well for 2 hours.

(ii) Washing: The plates were washed thoroughly with PBS+0.05% Tween 20 and incubated for 30 minuted with 1 ml of this wash buffer. This washing step was repeated three times.

(iii) Eution: The plates were incubated for 10 minutes in an elution buffer consisting of 20 mM Tris-HCl pH 8.6+100 mM NaCl, then the phage were eluted with 0.5 ml of the above buffer with or without 500 nM of A64SAL subtilisin.

Table XVII shows that there was a dramatic increase in the ratio of specifically eluted substrate-phagemid particles compared to the method previously described for pS0640 and pS0132. It is likely that this is due to the fact that the tight-binding hGH mutant has a significantly slower off-rate for binding to hGH binding protein compared to wild-type hGH.

TABLE XVII

Specific elution of substrate-phagemids by A64SAL subtilisin
Colony forming units (cfu) were estimated by plating out 10 μl of
10-fold dilutions of phage on 10 μl spots of XL-1 blue cells, on LB
agar plates containing 50 μg/ml carbenicillini

| phagemid | +50 nM A64SAL | no enzyme |
|---|---|---|
| (i) Wild-type hGH gene; binding to hGHbp-oxirane beads | | |
| pS0640 (substrate) | $9 \times 10^6$ cfu/10 μl | $1.5 \times 10^6$ cfu/10 μl |
| pS0132 (non-substrate) | $6 \times 10^5$ cfu/10 μl | $3 \times 10^5$ cfu/10 μl |
| (ii) pH0650bd mutant hGH gene: binding to hGHbp-coated plates | | |
| pDM0411 (substrate) | $1.7 \times 10^5$ cfu/10 μl | $2 \times 10^3$ cfu/10 μl |
| pDM0390 (non-substrate) | $2 \times 10^3$ cfu/10 μl | $1 \times 10^3$ cfu/10 μl |

EXAMPLE XIV

Identification of preferred substrates for A64SAL subtilisin using selective enrichment of a library of substrate sequences We sought to employ the selective enrichment procedure described in Example XIII to identify good substrate sequences from a library of random substrate sequences.

Construction of a vector for insertion of randomized substrate cassettes

We designed a vector suitable for introduction of randomized substrate cassettes and subsequent expression of a library of substrate sequences. The starting point was the vector pS0643, described in Example VIII. Site-directed mutagenesis was carried out using the oligonucleotide 5'-AGC-TGT-GGC-TTC-GGG-CCC-GCC-GCC-GC G-TCG-ACT-GGC-GGT-GGC-TCT-3' (SEQ ID NO:28), which introduces ApaI (GGGCCC) and SalII (GTCGAC) restriction sites between hGH and Gene III. This new construct was designated pDM0253 (The actual sequence of pDM0253 is 5'-AGC-TGT-GGC-TTC-GGG-CCC-GCC-CCC-GCG-TCG-ACT-GGC-GGT-GGC-TCT-3'(SEQ ID NO:29), where the underlined base substitution is due to a spurious error in the mutagenic oligonucleotide). In addition, the tight-binding hGH variant described in example was introduced by exchanging a fragment from pDM0411 (Example XIII). The resulting library vector was designated pDM0454.

Preparation of the library cassette vector and insertion of the mutagenic cassette To introduce a library cassette, pDM0454 was digested with ApaI followed by SalI, then precipitated with 13% PEG 8000+ 10 mM MgCl$_2$, washed twice in 70% ethanol and resuspended. This efficiently precipitates the vector but leaves the small Apa-SaI fragment in solution (Paithanikar, K. R. and Prasad, K. S. N., Nucleic Acids Research 19:1346). The product was run on a 1% agarose gel and the ApaI-SalI digested vector excised, purified using a Bandprep kit (Pharmacia) and resuspended for ligation with the mutagenic cassette.

The cassette to be inserted contained a DNA sequence similar to that in the linker region of pS0640 and pDM0411, but with the codons for the histidine and tyrosine residues in the substrate sequence replaced by randomized codons. We chose to substitute NNS (N=G/A/T/C; S=G/C) at each of the randomized positions as described in Example VIII. The oligonucleotides used in the mutagenic cassettes were 5'-C-TTC-GCT-GCT-NNS-NNS-ACC-CGG-CAA-3' (SEQ ID NO:30) (non-coding strand) and 5'-T-CGA-TTG-CCG-GGT-SNN-SNN-AGC-AGC-GAA-GGG-CC-3' (SEQ ID NO:31) (non-coding strand). This cassette also destroys the SalI site, so that digestion with SalI may be used to reduce the vector background. The olgonucleotides were not phosphorylated before insertion into the Apa-SaI cassette site, as it was feared that subsequent oligomerization of a small population of the cassettes may lead to spurious results with multiple cassette inserts. Following annealing and ligation, the reaction products were phenol:cholorform extracted, ethanol precipitated and resuspended in water. Initially, no digestion with SalI to reduce the background vector was performed. Approximately 200 ng was electroporated into XL-1 blue cells and a phagemid library was prepared as described in example VIII.

Selection of highly cleavable substrates from the substrate library

The selection procedure used was identical to that described for pDM0411 and pDM0390 in Example XIII. After each round of selection, the eluted phage were propagated by transducing a fresh culture of XL-1 blue cells and propagating a new phagemid library as described for hGH-phage in Example VIII. The progress of the selection procedure was monitored by measuring eluted phage titres and by sequencing individual clones after each round of selection.

Table A shows the successive phage titres for elution in the presence and absence of enzyme after 1, 2 and 3 rounds of selection. Clearly, the ratio of specifically eluted phage:non-specifically eluted phage (ie phage eluted with enzyme:phage eluted without enzyme) increases dramatically from round 1 to round 3, suggesting that the population of good substrates is increasing with each round of selection.

Sequencing of 10 isolates from the starting library showed them all to consist of the wild-type pDM0464 sequence. This is attributed to the fact that after digestion with ApaI, the SalI site is very close to the end of the DNA fragment, thus leading to low efficiency of digestion. Nevertheless, there are only 400 possible sequences in the library, so this population should still be well represented.

Tables B1 and B2 shows the sequences of isolates obtained after round 2 and round 3 of selection. After 2 rounds of selection, there is clearly a high incidence of histidine residues. This is exactly what is expected: as described in Example XIII, A64SAL subtilisin requires a histidine residue in the substrate as it employs a substrate-assisted catalytic mechanism. After 3 rounds of selection, each of the 10 clones sequenced has a histidine in the randomized cassette. Note, however, that 2 of the sequences are of pDM0411, which was not present in the starting library and is therefore a contaminant.

TABLE A

Titration of Initial phage pools and eluted phage from 3 rounds of selective enrichment Colony forming units (cfu) were estimated by plating out 10 μl of 10-fold dilutions of phage on 10 μl spots of XL-1 blue cells, on LB agar plates containing 50 μg/ml carbenicillin

| ROUND 1 | | |
|---|---|---|
| Starting library: | $3 \times 10^{12}$ cfu/ml | |
| LIBRARY: | +500 nM A64SAL | $4 \times 10^3$ cfu/10 μl |
| | no enzyme | $3 \times 10^3$ cfu/10 μl |
| pDM0411: | +500 nM A64SAL | $2 \times 10^6$ cfu/10 μl |
| (control) | no enzyme | $8 \times 10^3$ cfu/10 μl |
| ROUND 2 | | |
| Round 1 library: | $7 \times 10^{12}$ cfu/ml | |
| LIBRARY: | +500 nM A64SAL | $3 \times 10^4$ cfu/10 μl |
| | no enzyme | $6 \times 10^3$ cfu/10 μl |
| pDM0411: | +500 nM A64SAL | $3 \times 10^6$ cfu/10 μl |
| (control) | no enzyme | $1.6 \times 10^4$ cfu/10 μl |
| ROUND 3 | | |
| Round 2 library: | $7 \times 10^{11}$ cfu/ml | |
| LIBRARY: | +500 nM A64SAL | $1 \times 10^5$ cfu/10 μl |
| | no enzyme | $<10^3$ cfu/10 μl |
| pDM0411: | +500 nM A64SAL | $5 \times 10^6$ cfu/10 μl |
| (control) | no enzyme | $3 \times 10^4$ cfu/10 μl |

TABLE B1

Sequences of eluted phage after 2 rounds of selective enrichment. All protein sequences should be of the form AA**TRQ, where * represents a randomized codon. In the table below, the randomized codons and amino acids are underlined and in bold.

After round 2:

| Sequence | | No. of occurrences |
|---|---|---|
|           \*   \* | | |
| A  A  H  Y  T  R  Q | (SEQ ID NO:27) | |
| ... GCT GCT CAC TAC ACC CGG CAA ... | (SEQ ID NO:32) | 2 |
| A  A  H  M  T  R  Q | (SEQ ID NO:33) | |
| ... GCT GCT CAC ATG ACC CGG CAA ... | (SEQ ID NO:34) | 1 |
| A  A  L  H  T  R  Q | (SEQ ID NO:35) | |
| ... GCT GCT CTC CAC ACC CGG CAA ... | (SEQ ID NO:36) | 1 |
| A  A  L  H  T  R  Q | (SEQ ID NO:35) | |
| ... GCT GCT CTG CAC ACC CGG CAA ... | (SEQ ID NO:37) | 1 |
| A  A  H  T  R  Q | (SEQ ID NO:38) | |
| ... GCT GCT CAC ACC CGG CAA ... | (SEQ ID NO:39) | 1# |
| A  A  ?  H  T  R  Q | (SEQ ID NO:40) | |
| ... GCT GCT ? ? ? CAC ACC CGG CAA | (SEQ ID NO:41) | 1## |
| ... wild-type pDM0454 | | 3 | spurious deletion of 1 codon within the cassette
ambiguous sequence

This deposit of plasmid pd ATCC no. 68663 was made under the provisions of the Budapest Treaty on the international Recognition of the Deposit of Microorganisms for the Purpose of Patent Procedure and the Regulations thereunder (Budpest Treaty). This assures maintenance of a viable culture for 30 years from date of deposit. The organisms will be made available by ATCC under the terms of the Budapest Treaty, and subject to an agreement between Genentech, Inc. and ATCC, which assures permanent and unrestricted availablity of the progeny of the cultures to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 37 CFR §1.14 with particular reference to 886 OG 638).

The assignee of the present application has agreed that if the cultures on deposit should die or be lost or destroyed when cultivated under suitable conditions, they will be promptly replaced on notification with available specimen of the same culture. Availability of the deposited cultures is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the cultures deposited, since the deposited embodiments are intended as separate illustrations of certain aspects of the invention and any cultures that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustrations that it represents. Indeed, various modifications of the invention in addition to those shown and described herein will becomes apparent to those skilled in the art from the foregoing description and fall within the scope of the appended claims.

While the invention has necessarily been described in conjunction with preferred embodiments, one of ordinary skill, after reading the foregoing specification, will be able to effect various changes, substitutions of equivalents, and alterations to the subject matter set forth herein, without departing from the spirit and scope thereof. Hence, the invention can be practiced in ways other than those specifically described herein. It is therefore intended that the protection granted by Letters Patent hereon be limited only by the appended claims and equivalents thereof.

TABLE B2

Sequences of eluted phage after 3 rounds of selective enrichment.
All protein sequences should be of the form AA**TRQ, where *
represents a randomised codon. In the table below, the randomised
codons and amino acids are underlined and in bold.

After round 3:

| Sequence | | No. of occurrences |
|---|---|---|
| A A H Y T R Q | (SEQ ID NO:27) | |
| ... GCT GCT CAC TAT ACG CGT CAG ... | (SEQ ID NO:42) | 2# |
| A A L H T R Q | (SEQ ID NO:35) | |
| ... GCT GCT CTC CAC ACC CGG CAA ... | (SEQ ID NO:36) | 2 |
| A A Q H T R Q | (SEQ ID NO:43) | |
| ... GCT GCT CAG CAC ACC CGG CAA ... | (SEQ ID NO:44) | 1 |
| A A T H T R Q | (SEQ ID NO:45) | |
| ... GCT GCT ACG CAC ACC CGG CAA ... | (SEQ ID NO:46) | 1 |
| A A H S R Q | (SEQ ID NO:47) | |
| ... GCT GCT CAC TCC CGG CAA ... | (SEQ ID NO:48) | 1 |
| A A H H T R Q | (SEQ ID NO:49) | |
| ... GCT GCT CAT CAT ACC CGG CAA | (SEQ ID NO:50) | 1## |
| A A H F R Q | (SEQ ID NO:51) | |
| ... GCT GCT CAC TTC CGG CAA ... | (SEQ ID NO:52) | 1 |
| A A H T R Q | (SEQ ID NO:38) | |
| ... GCT GCT CAC ACC CGG CAA ... | (SEQ ID NO:39) | 1 | contaminating sequence from pDM0411
contains the "illegal" codon CAT - T should not appear in the 3rd position of a codon.

---

What is claimed is:

1. A method for selecting novel binding polypeptides comprising:
   (a) constructing a replicable expression vector comprising a transcription regulatory element operably linked to a gene fusion encoding a fusion protein wherein the gene fusion comprises
      a first gene encoding a polypeptide, and
      a second gene encoding at least a portion of a wild-type M13 phage gene III coat protein;
   (b) mutating the vector at one or more selected positions within the first gene thereby forming a family of related plasmids;
   (c) transforming suitable E. coli host cells with the plasmids;
   (d) infecting the transformed host cells with a M13K07 helper phage having a gene encoding the wild-type M13 phage gene III coat protein;
   (e) culturing the transformed infected E. coli host cells under conditions suitable for forming recombinant phagemid particles containing at least a portion of the plasmid and capable of infecting the E. coli host, the phagemid particles displaying a mixture of the wild-type M13 phage gene III coat protein and the fusion protein;
   (f) contacting the phagemid particles with a target molecule so that at least a portion of the phagemid particles bind to the target molecule; and
   (g) separating the phagemid particles that bind from those that do not.

2. The method of claim 1 further comprising infecting suitable E. coli host cells with the phagemid particles that bind to the target and repeating steps (d) through (g).

3. The method of claim 2 wherein the steps are repeated more than once and where the polypeptide is heterologous to the phagemid.

4. The method of claim 1 wherein the expression vector further comprises a secretory signal sequence.

5. The method of claim 4 wherein the expression vector further comprises a third gene encoding a polypeptide, the third gene operably linked to a second secretory signal sequence.

6. The method of claim 5 further compromising mutating the vector at one or more selected positions within the third gene.

7. The method of claim 6 wherein the first gene encodes the variable domain of an IgG antibody heavy chain and at least a portion of the heavy chain constant region of an IgG antibody.

8. The method of claim 7 wherein the thord gene encodes the variable and constant regions of an IgG antibody.

9. The method of claim 8 wherein the vector is mutated in one or more of the codons encoding amino acids corresponding to the complemetarity-determining regions (CDRs).

10. The method of claim 1 wherein the first gene encodes a mammalian polypeptide.

11. The method of claim 6 wherein the polypeptide is a protein selected from the group consisting of:
   growth hormone, human growth hormone (hGH), des-N-methionyl human growth hormone, bovine growth hormone, parathyroid hormone, thyroxine, insulin A-chain, insulin B-chain, proinsulin, relaxin A-chain, relaxin B-chain, prorelaxin, follicle stimulating hormone (FSH), thyroid stimulating hormone (TSH), leutinizing hormone (LH), glycoprotein hormone receptors, calcitonin, glucagon, factor VIII, an antibody, the Fab portion of an IgG antibody, a humanized IgG antibody, the variable domain and the first domain of the consistent region of the heavy chain of a humanized IgG antibody, lung surfactant, urokinase, streptokinase, human tissue-type plasminogen activator (t-PA), bombesin, factor IX, thrombin, hemopoietic growth factor, tumor necrosis factor-alpha and -beta, enkephalinase, human serum albumin, mullerian-inhibiting substance, mouse gonadotropin-associated peptide, β-lactamase, tissue factor protein, inhibin, activin, vascular endothelial growth factor, integrin receptors, thrombopoietin, protein A or D, rheumatoid factors, NGF-β, platelet-growth factor, transforming growth factor; TGF-alpha and TGF-beta, insulin-like growth factor-I and -II, insulin-like growth factor binding proteins, CD-4, DNase, latency associated peptide, erythropoietin, HER2 ligands, osteoinductive factors, interferon-alpha, -beta, and -gamma, colony stimulating factors (CSFs), M-CSF, GM-CSF, and G-CSF, interleukins (ILs), IL-1, IL-2, IL-3, IL-4, superoxide dismutase; decay accelerating factor, viral antigen, HIV envelope proteins GP120 and GP140, atrial natriuretic peptides A, B, or C, and immuno globulins.

12. The method of claim 10 wherein the polypeptide is a human protein.

13. The method of claim 12 wherein the protein comprises more than about 100 amino acid residues.

14. The method of claim 1 wherein the polypeptide comprises a plurality of rigid secondary structures displaying amino acids capable of interacting with the target, and the mutations are primarily produced at positions corresponding to codons encoding the amino acids.

15. The method of claim 14 wherein the rigid secondary structures comprise structures selected from the group consisting of; $\alpha\text{-}(3.6_{13})$helix, $3_{10}$helix, $\pi\text{-}(4.4_{16})$helix, parallel and anti-parallel $\beta$-pleated sheets, reverse turns, and non-ordered structures.

16. The method of claim 14 wherein the mutations are produced at more than one codon.

17. The method of claim 16 wherein the mutations are produced on more than one rigid secondary structure.

18. The method of claim 1 wherein the percentage of phagemid particles displaying more than a single copy of the fusion protein is less than about 1%.

19. The method of claim 1 wherein the percentage of phagemid particles displaying more than a single copy of the fusion protein is less than about 20%.

20. The method of claim 1 wherein the percentage of phagemid particles displaying more than a single copy of the fusion protein is less than about 10%.

21. The method of claim 1 further comprising in step (a), inserting a DNA triplet, encoding an mRNA suppressible terminator codon between said first gene encoding a polypeptide, and the second gene encoding a least a portion of a M13 phage gene III coat protein.

22. The method of claim 21 wherein the mRNA suppressible terminator codon is selected from the following: UAG (amber), UAA (ocher) and UGA (opel).

23. The method of claim 22 wherein the suppressible mutation results in the detectable production of a fusion polypeptide containing the polypeptide and the coat protein when the expression vector is grown in a suppressor host cell; and, when grown in a non-suppressor host cell the polypeptide is synthesized substantially without fusion to the phage coat protein.

24. A method for selecting noval binding polypeptides comprising (a) constructing a replicable expression vector comprising a transcription regulatory element operably linked to DNA encoding a polypeptide of interest containing one or more subunits, wherein the DNA encoding at least one of the subunits is fused to the DNA encoding at least a portion of a M13 phage gene III coat protein;

(b) mutating the DNA encoding the polypeptide of interest at one or more selected positions thereby forming a family of related vectors;

(c) transforming suitable *E. coli* host cells with the vectors;

(d) infecting the transformed host cells with a M13K07 helper phage having a gene encoding the gene III phage coat protein;

(e) culturing the transformed infected *E. coli* host cells under conditions suitable for forming recombinant phagemid particles containing at least a portion of the plasmid and capable of infecting the host, at least a portion of the phagemid particles displaying a mixture of the wild-type phage coat protein and the fusion containing the protein of interest;

(f) contacting the phagemid particles with a target molecule so that at least a portion of the phagemid particles bind to the target molecule; and (g) separating the phagemid particles that bind from those that do not.

25. The method of claim 24 wherein the expression vector further comprises a secretory signal sequence operably linked to the DNA encoding each subunit of the protein of interest.

26. The method of claim 25 wherein the protein of interest is a mammalian protein.

27. The method of claim 26 wherein the protein of interest is selected from the group; insulin, relaxin, follicle stimulating hormone (FSH), thyroid stimulating hormone (TSH), leutinizing hormone (LH), glycoprotein hormone receptors, monoclonal and polyclonal antibodies, lung surfactant, integrin receptors and insulin-like growth factor-I and -II.

28. The method of claim 27 wherein the protein of interest is a humanized antibody.

29. The method of claim 28 wherein the protein of interest is a humanized Fab fragment capable of binding to the HER-2 receptor (human epidermal growth factor receptor-2).

30. A method for selecting novel protease substrate polypeptides comprising:

(a) constructing a replicable expression vector comprising a transcription regulatory element operably linked to a gene fusion encoding a fusion protein wherein the gene fusion comprises
a first gene encoding a polypeptide operable connected to a linking amino acid sequence, and
a second gene encoding at least a portion of M13 phage gene III coat protein;

(b) mutating the vector at one or more selected positions within the amino acid linking sequence of the first gene thereby forming a family of related plasmids;

(c) transforming suitable *E. coli* host cells with the plasmids;

(d) infecting the transformed host cells with a M13K07 helper phage having a gene encoding the wild-type phage coat protein;

(e) culturing the transformed infected host cells under conditions suitable for forming recombinant phagemid particles containing at least a portion of the plasmid and capable of infecting the host, at least a portion of the phagemid particles displaying a mixture of the wild-type phage coat protein and the fusion protein;

(f) contacting the phagemid particles with a target molecule so that at least a portion of the phagemid particles bind to the target molecule; and (g) contacting the bound phagemid particles with a protease capable of hydrolyzing the linking a amino acid sequence of at least a portion of the bound phagemid particles, and (h) isolating the hydrolyzed phagemid particles.

31. The method of claim 30 further comprising infecting suitable *E. coli* host cells with the hydrolyzed phagemid particles and repeating steps (d) through (h).

32. An M13 phagemid capable of infecting an *E. coli* host comprising a replicable expression vector comprising a transcription regulatory element operably linked to a gene fusion encoding a fusion protein wherein the gene fusion comprises a first gene encoding a polypeptide, and a second gene encoding at least a portion of a M13 phage gene III coat protein, wherein a DNA triplet codon encoding an mRNA suppressible terminator codon selected from UAG, UAA and UGA is inserted between the fused ends of the first and second genes, or is substituted for an amino acid encoding triplet codon adjacent to the gene fusion junction.

33. The phagemid of claim 32 wherein the first gene encodes a mammalian polypeptide.

34. The phagemid of claim 33 wherein the polypeptide is a protein selected from the group consisting of: growth hormone, human growth hormone (hGH), des-N-methionyl human growth hormone, bovine growth hormone, parathyroid hormone, thyroxine, insulin A-chain, insulin B-chain, proinsulin, relaxin A-chain, relaxin B-chain, prorelaxin, follicle stimulating hormone (FSH), throid stimulating hormone (TSH), leutinizing hormone (LH), glycoprotein hormone receptors, calcitonin, glucagon, factor VIII, an antibody, the Fab portion of an IgG antibody, a humanized IgG antibody, the variable domain and the first domain of the consistent region of the heavy chain of a humanized IgG antibody, lung surfactant, urokinase, streptokinase, human tissue-type plasminogen activator (t-PA), bombesin, factor IX, thrombin, hemopoietic growth factor, tumor necrosis factor-alpha and -beta, enkephalinase, human serum albumin, mullerian-inhibiting substance, mouse gonadotropin-associated peptide, β-lactamase, tissue factor protein, inhibin, activin, vascular endothelial growth factor, integrin receptors, thrombopoietin, protein A or D, rheumatoid factors, NGF-β, platelet-growth factor, transforming growth factor; TGF-alpha and TGF-beta, insulin-like growth-1 and -II, insulin-like growth factor binding proteins, CD-4, DNase, latency associated peptide, erythropoietin, osteoinductive factors, interferon-alpha, -beta, and -gamma, colony stimulating factors (CSFs), M-CSF, GM-CSF, and G-CSF, interleukins (ILs), IL-1, IL-2, IL-3, IL-4, superoxide dismutase; decay accelerating factor, viral antigen, HIV envelope proteins GP120 and GP140, atrial natriuretic peptides A, B or C and immuno globulins.

35. The phagemid of claim 34 wherein the fusion protein comprises a human protein.

36. The phagemid of claim 35 wherein the protein comprises more than about 100 amino acid residues.

37. The phagemid of claim 32 wherein the fusion protein comprises a plurality of rigid secondary structures displaying amino acids capable of interacting with the target.

38. The phagemid of claim 37 wherein the rigid secondary structures comprises structures selected from the group consisting of; α-(3.6$_{13}$)helix, 3$_{10}$helix, π-(4.4$_{16}$)helix, parallel and anti-parallel β-pleated sheets, reverse turns and non-ordered structures.

39. The phagemid of claim 32 wherein the host is the *E. coli* wild type or suppressor type.

40. The phagemid of claim 39 wherein the plasmid is under tight control of the transcription regulatory element.

41. The phagemid of claim 40 wherein the number of phagemid displaying more than one copy of the fusion protein on the surface of the particles is less than 1%.

42. The phagemid of claim 40 wherein the percentage of phagemid displaying more than a single copy of the fusion protein is less than about 10%.

43. The phagemid of claim 40 wherein the percentage of phagemid particles displaying more than a single copy of the fusion protein is less than about 20%.

44. A human growth hormone variant wherein hGH amino acids 172, 174, 176 and 178 respectively are as a group sequentially selected from the group consisting of: (1)R,S,F,R; (2)R,A,Y,R; (3)K,T,Y,K; (4)R,S,Y,R; (5)K,A,Y,R; (6)R,F,F,R; (7)K,Q,Y,R; (8)R,T,Y,H; (9)Q,R,Y,R; (10)K,K,Y,K; (11)R,S,F,S and (12)K,S,N,R.

45. A human growth variant wherein hGH amino acids 10, 14, 18, and 21 respectively are as a group sequentially selected from the group consisting of: (1)H,G,N,N; (2)A,W,D,N; (3)F,S,F,L; (4)Y,T,V,N and (5)I,N,I,N.

46. A human growth variant wherein hGH amino acids 174 is serine and 176 is tyrosine and hGH amino acids 167, 171, 175 and 179 respectively are as a group sequentially selected from the group consisting of: (1)N,S,T,T; (2)E,S,T,I; (3)K,S,T,L; (4)N,N,T,T; (5)R,D,I,I and (6)N,S,T,Q.

47. A human growth hormone (hGH) variant wherein hGH amino acid glutamate$_{174}$ is replaced by serine$_{174}$ and phenylalanine$_{176}$ is replaced by tyrosine$_{176}$ and one or more of the eight naturally occurring hGH amino acids F10, M14, H18, H21, R167, D171, T175 and I179 are replaced by another natural amino acid.

48. The hGH variant of claim 47 wherein the eight naturally occurring hGH amino acids F10, M14, H18, H21, R167, D171, T175 and I179 respectively are as a group replaced with a corresponding amino acid sequentially selected from the group consisting of:

| (1) H, G, N, N, N, S, T, T;   | (2) H, G, N, N, E, S, T, I;   |
|---|---|
| (3) H, G, N, N, N, N, T, T;   | (4) A, W, D, N, N, S, T, T;   |
| (5) A, W, D, N, E, S, T, I;   | (6) A, W, D, N, N, N, T, T;   |
| (7) F, S, F, L, N, S, T, T;   | (8) F, S, F, L, E, S, T, I;   |
| (9) F, S, F, L, N, N, T, T;   | (10) H, G, N, N, N, S, T, N;  |
| (11) A, N, D, A, N, N, T, N;  | (12) F, S, F, G, H, S, T, T;  |
| (13) H, Q, T, S, A, D, N, S;  | (14) H, G, N, N, N, A, T, T;  |
| (15) F, S, F, L, S, D, T, T;  | (16) A, S, T, N, R, D, T, I;  |
| (17) Q, Y, N, N, H, S, T, T;  | (18) W, G, S, S, R, D, T, I;  |
| (19) F, L, S, S, K, N, T, V;  | (20) W, N, N, S, H, S, T, T;  |
| (21) A, N, A, S, N, S, T, T;  | (22) P, S, D, N, R, D, T, I;  |
| (23) H, G, N, N, N, N, T, S;  | (24) F, S, T, G, R, D, T, I;  |
| (25) M, T, S, N, Q, S, T, T;  | (26) F, S, F, L, T, S, T, S;  |
| (27) A, W, D, N, R, D, T, I;  | (28) A, W, D, N, H, S, T, N;  |
| (29) M, Q, M, N, N, S, T, T;  | (30) H, Y, D, H, R, D, T, T;  |
| (31) L, N, S, H, R, D, T, I;  | (32) L, N, S, H, T, S, T, T;  |
| (33) A, W, D, N, N, A, T, T;  | (34) F, S, T, G, R, D, T, I;  |
| (35) A, W, D, N, R, D, T, I;  | (36) I, Q, E, H, N, S, T, T;  |
| (37) F, S, L, A, N, S, T, V;  | (38) F, S, F, L, K, D, T, T;  |
| (39) M, A, D, N, N, S, T, T;  | (40) A, W, D, N, S, S, V, T; and |
| (41) H, Q, Y, S, R, D, T, I.  | |

49. The hGH variant of claim 48 wherein the human growth hormone variant further contains leucine$_{15}$ replaced by arginine$_{15}$ and lysine$_{168}$ replaced by arginine$_{168}$.

50. The hGH variant of claim 49 wherein the human growth hormone variant further contains phenylalamine$_{176}$.

* * * * *

SEQUENCE LISTING ( 1 ) GENERAL INFORMATION:

( i i i ) NUMBER OF SEQUENCES: 52

( 2 ) INFORMATION FOR SEQ ID NO:1:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

GGCAGCTGTG GCTTCTAGAG TGGCGGCGGC TCTGGT    36

( 2 ) INFORMATION FOR SEQ ID NO:2:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

AGCTGTGGCT TCGGGCCCTT AGCATTTAAT GCGGTA    36

( 2 ) INFORMATION FOR SEQ ID NO:3:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

TTCACAAACG AAGGGCCCCT AATTAAAGCC AGA 33

( 2 ) INFORMATION FOR SEQ ID NO:4:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

CAATAATAAC GGGCTAGCCA AAAGAACTGG 30

( 2 ) INFORMATION FOR SEQ ID NO:5:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

CACGACAGAA TTCCCGACTG GAAA 24

( 2 ) INFORMATION FOR SEQ ID NO:6:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

CTGTTTCTAG AGTGAAATTG TTA 23

( 2 ) INFORMATION FOR SEQ ID NO:7:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

GACATTCCTG GGTACCGTGC AGT 23

( 2 ) INFORMATION FOR SEQ ID NO:8:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

GCTTCAGGAA GGACATGGAC NNSGTCNNSA CANNSCTGNN SATCGTGCAG 50

( 2 ) INFORMATION FOR SEQ ID NO:9:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

AAGGTCTCCA CATACCTGAG GATC                                                                          24

( 2 ) INFORMATION FOR SEQ ID NO:10:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

ATGGACAAGG TGTCGACATA CCTGCGCATC GTG                                                                33

( 2 ) INFORMATION FOR SEQ ID NO:11:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

GGCAGCTGTG GCTTCTAGAG TGGCGGCGGC TCTGGT                                                             36

( 2 ) INFORMATION FOR SEQ ID NO:12:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

GGCAGCTGTG GATTCTAGAG TGGCGGTGGC TCTGGT                                                             36

( 2 ) INFORMATION FOR SEQ ID NO:13:

( i ) SEQUENCE CHARACTERISTICS:
        ( A ) LENGTH: 12 amino acids
        ( B ) TYPE: amino acid
        ( C ) STRANDEDNESS:
        ( D ) TOPOLOGY: linear ( x i ) SEQUENCE DESCRIPTION: SEQ ID NO:13:

Gly Ser Cys Gly Phe Glu Ser Gly Gly Gly Ser Gly
1               5                   10

( 2 ) INFORMATION FOR SEQ ID NO:14:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

CGGACTGGGC AGATATTCAA GCAGACC                                                                       27

( 2 ) INFORMATION FOR SEQ ID NO:15:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:15:

CTCAAGAACT ACGGGTTACC CTGACTGCTT CAGGAAGG                                                           38

( 2 ) INFORMATION FOR SEQ ID NO:16:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:16:

```
CGCATCGTGC AGTGCAGATC TGTGGAGGGC                                              30
```

( 2 ) INFORMATION FOR SEQ ID NO:17:

( i ) SEQUENCE CHARACTERISTICS:
        ( A ) LENGTH: 66 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:17:

```
GTTACTCTAC TGCTTTCAGG AAGGACATGG ACNNSGTCNN SACANNSCTG NNSATCGTGC              60
AGTGCA                                                                        66
```

( 2 ) INFORMATION FOR SEQ ID NO:18:

( i ) SEQUENCE CHARACTERISTICS:
        ( A ) LENGTH: 64 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:18:

```
GATCTGCACT GCACGATSNN CAGSNNTGTS NNGACSNNGT CCATGTCCTT CCTGAAGCAG              60
TAGA                                                                          64
```

( 2 ) INFORMATION FOR SEQ ID NO:19:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:19:

```
GCCTTTGACA GGTACCAGGA GTTTG                                                   25
```

( 2 ) INFORMATION FOR SEQ ID NO:20:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:20:

```
CCAACTATAC CACTCTCGAG GTCTATTCGA TAA                                          33
```

( 2 ) INFORMATION FOR SEQ ID NO:21:

( i ) SEQUENCE CHARACTERISTICS:
        ( A ) LENGTH: 66 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:21:

```
TCGAGGCTCN NSGACAACGC GNNSCTGCGT GCTNNSCGTC TTNNSCAGCT GGCCTTTGAC    60

ACGTAC                                                              66
```

( 2 ) INFORMATION FOR SEQ ID NO:22:

( i ) SEQUENCE CHARACTERISTICS:
        ( A ) LENGTH: 58 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:22:

```
GTGTCAAAGG CCAGCTGSNN AAGACGSNNA GCACGCAGSN NCGCGTTGTC SNNGAGCC     58
```

( 2 ) INFORMATION FOR SEQ ID NO:23:

( i ) SEQUENCE CHARACTERISTICS:
        ( A ) LENGTH: 65 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:23:

```
GTTACTCTAC TGCTTCNNSA AGGACATGNN SAAGGTCAGC NNSTACCTGC GCNNSGTGCA    60

GTGCA                                                               65
```

( 2 ) INFORMATION FOR SEQ ID NO:24:

( i ) SEQUENCE CHARACTERISTICS:
        ( A ) LENGTH: 64 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:24:

```
GATCTGCACT GCACSNNGCG CAGGTASNNG CTGACCTTSN NCATGTCCTT SNNGAAGCAG    60

TAGA                                                                64
```

( 2 ) INFORMATION FOR SEQ ID NO:25:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:25:

```
TTCGGGCCCT TCGCTGCTCA CTATACGCGT CAGTCGACTG ACCTGCCT                48
```

( 2 ) INFORMATION FOR SEQ ID NO:26:

( i ) SEQUENCE CHARACTERISTICS:
        ( A ) LENGTH: 14 amino acids
        ( B ) TYPE: amino acid
        ( C ) STRANDEDNESS:
        ( D ) TOPOLOGY: linear ( x i ) SEQUENCE DESCRIPTION: SEQ ID NO:26:

```
Phe Gly Pro Phe Ala Ala His Tyr Thr Arg Gln Ser Thr Asp
 1               5                  10
```

( 2 ) INFORMATION FOR SEQ ID NO:27:

( i ) SEQUENCE CHARACTERISTICS:
        ( A ) LENGTH: 7 amino acids ( B ) TYPE: amino acid
( C ) STRANDEDNESS:
( D ) TOPOLOGY: linear ( x i ) SEQUENCE DESCRIPTION: SEQ ID NO:27:

Ala Ala His Tyr Thr Arg Gln
1               5

( 2 ) INFORMATION FOR SEQ ID NO:28:

( i ) SEQUENCE CHARACTERISTICS:
( A ) LENGTH: 45 base pairs
( B ) TYPE: nucleic acid
( C ) STRANDEDNESS: single
( D ) TOPOLOGY: linear ( x i ) SEQUENCE DESCRIPTION: SEQ ID NO:28:

AGCTGTGGCT TCGGGCCCGC CGCCGCGTCG ACTGGCGGTG GCTCT     45

( 2 ) INFORMATION FOR SEQ ID NO:29:

( i ) SEQUENCE CHARACTERISTICS:
( A ) LENGTH: 45 base pairs
( B ) TYPE: nucleic acid
( C ) STRANDEDNESS: single
( D ) TOPOLOGY: linear ( x i ) SEQUENCE DESCRIPTION: SEQ ID NO:29:

AGCTGTGGCT TCGGGCCCGC CCCCGCGTCG ACTGGCGGTG GCTCT     45

( 2 ) INFORMATION FOR SEQ ID NO:30:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( x i ) SEQUENCE DESCRIPTION: SEQ ID NO:30:

CTTCGCTGCT NNSNNSACCC GGCAA     25

( 2 ) INFORMATION FOR SEQ ID NO:31:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( x i ) SEQUENCE DESCRIPTION: SEQ ID NO:31:

TCGATTGCCG GGTSNNSNNA GCAGCGAAGG GCC     33

( 2 ) INFORMATION FOR SEQ ID NO:32:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( x i ) SEQUENCE DESCRIPTION: SEQ ID NO:32:

GCTGCTCACT ACACCCGGCA A     21

( 2 ) INFORMATION FOR SEQ ID NO:33:

( i ) SEQUENCE CHARACTERISTICS:
( A ) LENGTH: 7 amino acids
( B ) TYPE: amino acid -continued (C) STRANDEDNESS:
(D) TOPOLOGY: linear (xi) SEQUENCE DESCRIPTION: SEQ ID NO:33:

Ala Ala His Met Thr Arg Gln
1               5

(2) INFORMATION FOR SEQ ID NO:34:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (xi) SEQUENCE DESCRIPTION: SEQ ID NO:34:

GCTGCTCACA TGACCCGGCA A                                    21

(2) INFORMATION FOR SEQ ID NO:35:

(i) SEQUENCE CHARACTERISTICS:
    (A) LENGTH: 7 amino acids
    (B) TYPE: amino acid
    (C) STRANDEDNESS:
    (D) TOPOLOGY: linear (xi) SEQUENCE DESCRIPTION: SEQ ID NO:35:

Ala Ala Leu His Thr Arg Gln
1               5

(2) INFORMATION FOR SEQ ID NO:36:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (xi) SEQUENCE DESCRIPTION: SEQ ID NO:36:

GCTGCTCTCC ACACCCGGCA A                                    21

(2) INFORMATION FOR SEQ ID NO:37:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (xi) SEQUENCE DESCRIPTION: SEQ ID NO:37:

GCTGCTCTGC ACACCCGGCA A                                    21

(2) INFORMATION FOR SEQ ID NO:38:

(i) SEQUENCE CHARACTERISTICS:
    (A) LENGTH: 6 amino acids
    (B) TYPE: amino acid
    (C) STRANDEDNESS:
    (D) TOPOLOGY: linear (xi) SEQUENCE DESCRIPTION: SEQ ID NO:38:

Ala Ala His Thr Arg Gln
1               5

(2) INFORMATION FOR SEQ ID NO:39:

(i) SEQUENCE CHARACTERISTICS:
    (A) LENGTH: 18 base pairs ( B ) TYPE: nucleic acid
       ( C ) STRANDEDNESS: single
       ( D ) TOPOLOGY: linear ( x i ) SEQUENCE DESCRIPTION: SEQ ID NO:39:

GCTGCTCACA CCCGGCAA                                                                                                18

( 2 ) INFORMATION FOR SEQ ID NO:40:

( i ) SEQUENCE CHARACTERISTICS:
       ( A ) LENGTH: 4 amino acids
       ( B ) TYPE: amino acid
       ( C ) STRANDEDNESS:
       ( D ) TOPOLOGY: linear ( x i ) SEQUENCE DESCRIPTION: SEQ ID NO:40:

His Thr Arg Gln
    1

( 2 ) INFORMATION FOR SEQ ID NO:41:

( i ) SEQUENCE CHARACTERISTICS:
       ( A ) LENGTH: 12 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:41:

CACACCCGGC AA                                                                                                      12

( 2 ) INFORMATION FOR SEQ ID NO:42:

( i ) SEQUENCE CHARACTERISTICS:
       ( A ) LENGTH: 21 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:42:

GCTGCTCACT ATACGCGTCA G                                                                                            21

( 2 ) INFORMATION FOR SEQ ID NO:43:

( i ) SEQUENCE CHARACTERISTICS:
       ( A ) LENGTH: 7 amino acids
       ( B ) TYPE: amino acid
       ( C ) STRANDEDNESS:
       ( D ) TOPOLOGY: linear ( x i ) SEQUENCE DESCRIPTION: SEQ ID NO:43:

Ala Ala Gln His Thr Arg Gln
    1               5

( 2 ) INFORMATION FOR SEQ ID NO:44:

( i ) SEQUENCE CHARACTERISTICS:
       ( A ) LENGTH: 21 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:44:

GCTGCTCAGC ACACCCGGCA A                                                                                            21

( 2 ) INFORMATION FOR SEQ ID NO:45:

( i ) SEQUENCE CHARACTERISTICS:
       ( A ) LENGTH: 7 amino acids (B) TYPE: amino acid
        (C) STRANDEDNESS:
        (D) TOPOLOGY: linear (xi) SEQUENCE DESCRIPTION: SEQ ID NO:45:

Ala Ala Thr His Thr Arg Gln
    1               5

(2) INFORMATION FOR SEQ ID NO:46:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:46:

GCTGCTACGC ACACCCGGCA A                                        21

(2) INFORMATION FOR SEQ ID NO:47:

(i) SEQUENCE CHARACTERISTICS:
        (A) LENGTH: 6 amino acids
        (B) TYPE: amino acid
        (C) STRANDEDNESS:
        (D) TOPOLOGY: linear (xi) SEQUENCE DESCRIPTION: SEQ ID NO:47:

Ala Ala His Ser Arg Gln
    1               5

(2) INFORMATION FOR SEQ ID NO:48:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:48:

GCTGCTCACT CCCGGCAA                                            18

(2) INFORMATION FOR SEQ ID NO:49:

(i) SEQUENCE CHARACTERISTICS:
        (A) LENGTH: 7 amino acids
        (B) TYPE: amino acid
        (C) STRANDEDNESS:
        (D) TOPOLOGY: linear (xi) SEQUENCE DESCRIPTION: SEQ ID NO:49:

Ala Ala His His Thr Arg Gln
    1               5

(2) INFORMATION FOR SEQ ID NO:50:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:50:

GCTGCTCATC ATACCCGGCA A                                        21

(2) INFORMATION FOR SEQ ID NO:51:

(i) SEQUENCE CHARACTERISTICS:

( A ) LENGTH: 6 amino acids
          ( B ) TYPE: amino acid
          ( C ) STRANDEDNESS:
          ( D ) TOPOLOGY: linear ( x i ) SEQUENCE DESCRIPTION: SEQ ID NO:51:

Ala  Ala  His  Phe  Arg  Gln
    1                        5

( 2 ) INFORMATION FOR SEQ ID NO:52:

( i ) SEQUENCE CHARACTERISTICS:
          ( A ) LENGTH: 18 base pairs
          ( B ) TYPE: nucleic acid
          ( C ) STRANDEDNESS: single
          ( D ) TOPOLOGY: linear ( x i ) SEQUENCE DESCRIPTION: SEQ ID NO:52:

GCTGCTCACT TCCGGCAA                                                         1 8